US009687545B2

(12) United States Patent
Choi et al.

(10) Patent No.: US 9,687,545 B2
(45) Date of Patent: Jun. 27, 2017

(54) NONSPECIFIC IMMUNOSTIMULATOR COMPOSITION, METHOD OF PREPARATION THE SAME, AND ITS USE

(71) Applicant: BARODON-S.F.CORP., Gyeonggi-do (KR)

(72) Inventors: Soo-il Choi, Gyeonggi-do (KR); Hyun Suk Choi, Gyeonggi-do (KR); Yun Jeong Choi, Gyeonggi-do (KR); Kyung Ae Hong, Gyeonggi-do (KR); Byung Woo Yoo, Gyeonggi-do (KR); Yong Ho Park, Gyeonggi-do (KR); Sun Young Hwang, Gyeonggi-do (KR); Jeong Hee Han, Gyeonggi-do (KR); Chang Hoon Shin, Gyeonggi-do (KR)

(73) Assignee: BARODON-S.F.CORP., Anseong-si, Gyeonggi-Do (KR)

( * ) Notice: Subject to any disclaimer, the term of this patent is extended or adjusted under 35 U.S.C. 154(b) by 0 days.

(21) Appl. No.: 14/627,235

(22) Filed: Feb. 20, 2015

(65) Prior Publication Data

US 2015/0238599 A1 Aug. 27, 2015

(30) Foreign Application Priority Data

Feb. 27, 2014 (KR) ........................ 10-2014-0023396

(51) Int. Cl.

| | |
|---|---|
| ***A61K 33/06*** | (2006.01) |
| ***A61K 33/10*** | (2006.01) |
| ***A61K 33/14*** | (2006.01) |
| ***A61K 39/39*** | (2006.01) |
| ***A23K 1/16*** | (2006.01) |
| ***A61K 39/12*** | (2006.01) |
| ***A61K 33/00*** | (2006.01) |
| ***A61K 31/695*** | (2006.01) |
| ***A61K 33/04*** | (2006.01) |
| ***A23K 20/22*** | (2016.01) |
| ***A23K 50/10*** | (2016.01) |
| ***A23K 50/30*** | (2016.01) |
| ***A23K 50/80*** | (2016.01) |
| *A61K 39/00* | (2006.01) |

(52) U.S. Cl.
CPC .............. *A61K 39/39* (2013.01); *A23K 20/22* (2016.05); *A23K 50/10* (2016.05); *A23K 50/30* (2016.05); *A23K 50/80* (2016.05); *A61K 31/695* (2013.01); *A61K 33/00* (2013.01); *A61K 33/04* (2013.01); *A61K 33/14* (2013.01); *A61K 39/12* (2013.01); *A61K 2039/55505* (2013.01); *C12N 2770/32134* (2013.01)

(58) Field of Classification Search
CPC ............ A61K 2300/00; A61K 31/5377; A61K 31/404; C07D 487/04; C07D 471/04
See application file for complete search history.

(56) References Cited

U.S. PATENT DOCUMENTS 6,899,900 B2 * 5/2005 Choi .................. A61K 31/7016
424/658

FOREIGN PATENT DOCUMENTS

WO WO2008000042 * 1/2008

OTHER PUBLICATIONS

Yoo et al., Journal of Veterinary Science, 2001, 2(1):15-24.*

* cited by examiner

*Primary Examiner* — Janet L Andres
*Assistant Examiner* — Barry A Chestnut
(74) *Attorney, Agent, or Firm* — Egbert Law Offices, PLLC

(57) ABSTRACT

Disclosed are a nonspecific immunostimulant composition, a preparation method thereof, and uses thereof. The composition includes 150 to 300 wt. parts of sodium silicate, 2~8 wt. parts of sodium thiosulfate, 0.5~2 wt. parts of sodium carbonate, 0.5~2 wt. parts of potassium chloride, 200~400 wt. parts of white sugar, and 300~400 wt. parts of water, based on 100 wt. parts of potassium carbonate. The composition exhibits excellent defense against the mortality caused by AIV H5N1, thus improving the survival of infected animals. As a supplement of a formulated feed mixture for farmed aquatic organisms, the composition provides excellent immunostimulation and disease resistance so as to decrease the mass mortality of aquatic organisms and to increase productivity. Particularly, when raised with a food in mixture with the composition, livestock and farmed aquatic organisms are immunologically improved so that they can endure and are protected against epidemic diseases caused by viruses and bacteria.

3 Claims, 36 Drawing Sheets

NONSPECIFIC IMMUNOSTIMULATOR COMPOSITION, METHOD OF PREPARATION THE SAME, AND ITS USE

BACKGROUND OF THE INVENTION

1. Field of the Invention

The present invention relates to a nonspecific immunostimulant composition, a method of preparing the same, and uses thereof. More particularly, the present invention relates to a potassium carbonate ($K_2CO_3$)-based multifunctional complex mineral composition, a preparation method thereof, and uses thereof as a nonspecific immunostimulant.

2. Description of the Related Art

Since the early 20$^{th}$ century, the function of alkali materials has been studied. Extensive studies have recently revealed that when its constitution turns alkaline, the body increases in the ionization rate of potassium and sodium, which results in improving the blood's purification ability, increasing fatigue recovery ability, and delaying senescence.

Since the disclosure of Korean Patent No. 128,110, issued to the present inventor, such alkaline solutions have been applied in various industrial fields. The composition disclosed in the patent contains sodium silicate, sodium peroxide, white sugar, and silver thiosulfate in water, with a weight ratio of 10~18 of sodium silicate, 0.1~0.5 of sodium peroxide, 5~10 of potassium carbonate, 10~18 of white sugar, and 0.1~3.0 of thiosulfate based on 1 of sodium carbonate. Superior in far-red emission, antibacterial activity, and deodorizing activity, the composition is widely used for the post-treatment of fabric products, the fermentation of diet, and in the agricultural field. However, the composition suffers from the disadvantage of being complicated in the preparation thereof, and being inconvenient for long-term storage. Further, the composition cannot be used as an antibacterial agent and nonspecific immunostimulant for general purposes.

To overcome these disadvantages, a solution was suggested in Korean Patent No. 10-0331952, issued to the present inventor. The composition comprises 1~15 weight parts of borax, $10^{-5}$~$10^{-4}$ weight parts of sodium thiosulfate, 30~150 weight parts of potassium carbonate, 30~200 weight parts of white sugar, 100~200 weight parts of water based on sodium meta silicate, and is found to perfectly overcome the problem of inconvenient long-term storage and incompetence as an immunostimulant for animals and plants.

However, this technique, in spite of high immunostimulatory effects on animals and plants, is limited in application because the effect (safety) of boron, contained in borax, on the body is not known.

SUMMARY OF THE INVENTION

Accordingly, the present invention has been made keeping in mind the above problems occurring in the prior art, and an object of the present invention is to provide an immunostimulant free of boron, which is suspected of being unsafe for the body.

It is another object of the present invention to provide a nonspecific immunostimulant that exhibits an excellent immunostimlatory effect on animals and plants.

It is a further object of the present invention to provide an immunostimulant that can provide livestock with resistance to diseases such as avian influenza, foot-and-mouth disease, etc.

It is a still further object of the present invention to provide an immunostimulant that can provide farmed aquatic organisms with disease resistance.

It is still another object of the present invention to provide an immunostimulant that can enhance human immunity to diseases.

In accordance with an aspect thereof, the present invention provides a composition comprising 150 to 300 parts by weight of sodium silicate, 2 to 8 parts by weight of sodium thiosulfate, 0.5 to 2 parts by weight of sodium carbonate, 0.5 to 2 parts by weight of potassium chloride, 200 to 400 parts by weight of white sugar and 300 to 400 parts by weight of water, based on 100 parts by weight of potassium carbonate.

As needed, the composition may further comprise 0.1 to 0.3 parts by weight of magnesium sulfate. In addition, optionally, the composition may further comprise $1\times10^{-3}$ to $8\times10^{-3}$ parts by weight of silver thiosulfate.

After undergoing fermentation and drying processes, the composition-supplemented diet can be converted into a functional fermented product.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
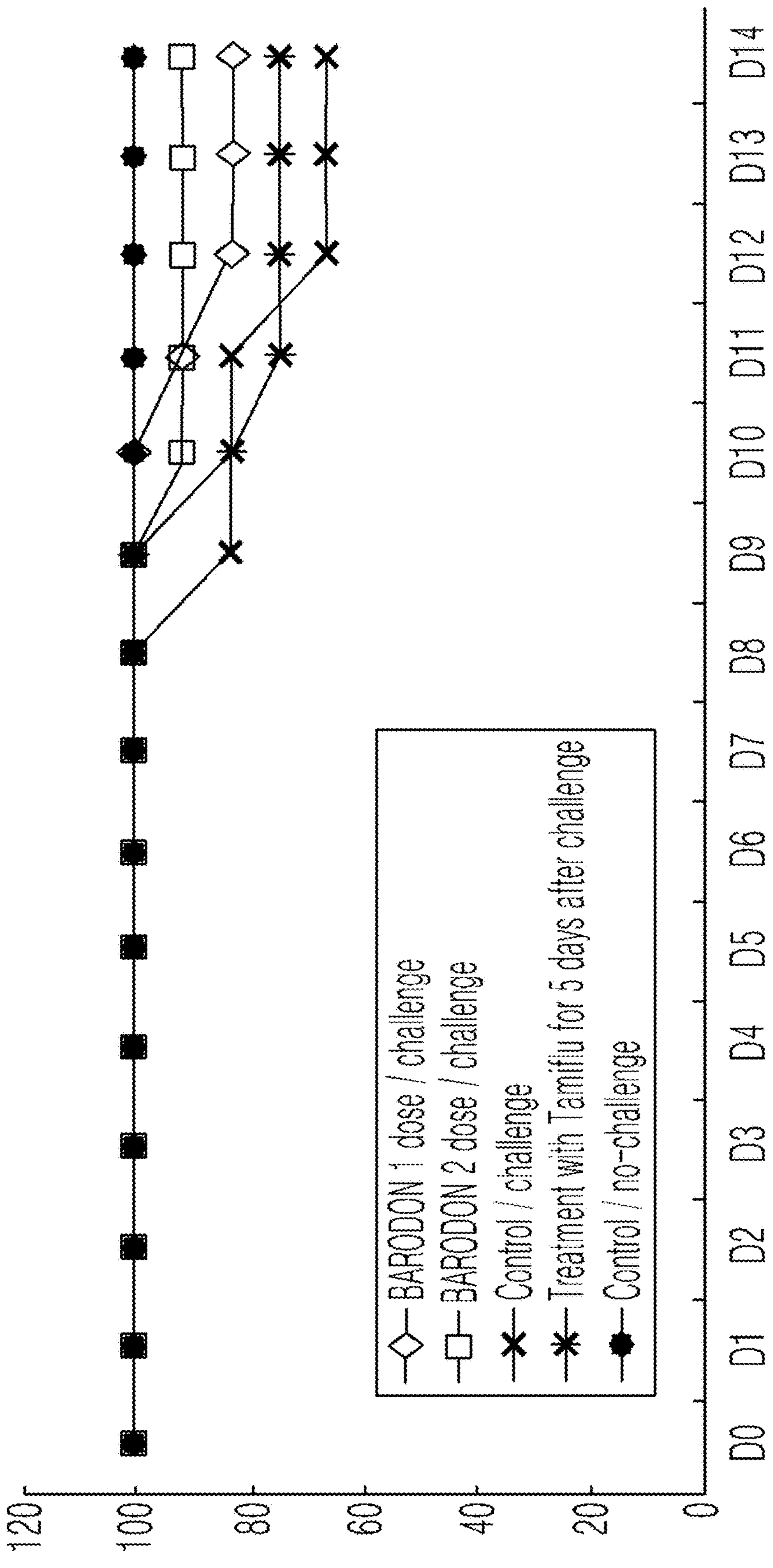
FIG. 1 is a graph showing the effect of BARODON Chois Gold on defense against highly pathogenic AIV H5N1-induced mortality.

Below, a detailed description will be given of the present invention.

Like proteins, carbohydrates, lipids, and vitamins, minerals (inorganic substances) are classified as one of the five nutrients required for cell constitution and growth, maintenance of life, and maintenance of health and normal physiological functions. Minerals cannot be synthesized in vivo. Approximately 42 minerals are found in the body, but only 25~30 minerals are known for their functions in the body. All of the 103 chemical elements existing on the earth, except for carbon, nitrogen, hydrogen and oxygen, are inorganic. Representative among the minerals useful in the body are calcium, magnesium, sodium, potassium, phosphorus, zinc, iron, copper, manganese, chrome, selenium, iodide, germanium, chlorine, sulfur, cobalt, silicon, boron, fluorine, and molybdenum. Four essential minerals include sodium, potassium, calcium, and magnesium.

These minerals are essential nutrients necessary for maintaining life and health, and are involved in the formation of hard structures such as bones and teeth, and soft structures such as muscles and organs. They are also involved in the acid-base balance and osmotic pressure control of body liquids, digestion, nerve stimulation, control, and enzymatic reactions. Minerals are important constituents of blood cells, hormones and are found in enzymes themselves. As much as 4% of the body consists of inorganic elements, with ¾ of the constitution being accounted for by calcium and phosphorus, and the balance by potassium, sodium, sulfur, chlorine, and magnesium. They are called major minerals (hereinafter referred to just as "minerals").

As various side effects have been generated due to the abuse and misuse of antibiotics, legislative systems that list and disclose in the press hospitals that have excessively prescribed antibiotics is in enforcement in order to reduce the use of antibiotics. In line with the European Union (EU)'s policy to ban the use of antibiotic growth promoters (AGPs) in food animal production, Korea introduced bans on the use of AGPs (7 antibiotics) in animal feed factories from Jul. 1, 2011.

In the United States, which is the largest livestock raising country in the world, as many as 30 antibiotics including penicillin and tetracycline as well as AGPs are used in feed. Of the 30 antibiotics added to feed, 18 may cause antibiotic-resistant bacterial infection in humans, as reported by the Food and Drug Administration (FDA) on Jan. 18, 2014. Antibiotic-resistant bacteria are generated in livestock fed antibiotics and may be introduced into the human body when the meat of the livestock is consumed. In this process, super bacteria, which are resistant to multiple drugs, are generated. Accordingly, products from agro-livestock fed antibiotics threaten human life.

Nevertheless, the misuse and abuse of antibiotics are very serious issues in animal feed factories and livestock farms.

Meanwhile, global pharmaceutical and biotech companies have competed with each other for the development of non-specific immunostimulants that can replace antibiotics as the use of antibiotic growth promoters (AGPs) in food animal production is banned or in order to cope with the infection of the multi-drug resistant bacteria [(methicillin-resistant *Staphylococcus aureus* (MRSA), vancomycin-resistant *Staphylococcus aureus* (VRSA)].

Scientifically proven immunostimulatory materials include minerals, live yeasts, probiotics, fungi, organic acids, herbs, and poly gamma glutamic acid. According to research results, such immunostimulatory materials generally enhance immunity, thereby helping vaccines effectively perform their functions, or effectively allowing the body to defend against the infection of pathogens such as highly pathogenic microorganisms, or to form antibodies against the pathogens.

Thus far, however, there have been no nonspecific immunostimulant complex mineral compositions that are provided with the following advantages: general applicability to farmed aquatic organisms, livestock, and humans; ability to enhance antibacterial activity, antiviral activity, immunity, and vaccine efficacy; productivity, storage and economic benefits; and mass productivity and wide applicability.

Potassium carbonate is used as a base material in the present invention. It is highly water soluble, and strongly alkaline with a pH of 11.6 in water. Potassium is an essential element in an animal body, and functions to contribute an acid-alkali balance in the body fluid. In addition, potassium plays an important role in converting blood sugar to glycogen and in storing proteins. Further, this element is involved in promoting metabolism and blood circulation, regulating the potassium sodium balance in the body, and preventing diseases that may be caused by excessive salt (NaCl) uptake, such as obesity, diabetes, hypertension, myocardial infarction, atherosclerosis, etc. Sodium may act as a cause of obesity and diabetes whereas potassium may be preventive of obesity and hypertension.

As an ingredient of the composition of the present invention, sodium silicate is a white powder or granule that is readily soluble in water, producing a strong alkaline solution. Sodium silicate is commonly manufactured using a reaction in liquid phase by dissolving 27.5~29.0% of silica ($SiO_2$) and 28.5~30.0% of sodium oxide ($Na_2O$) in water. Silicon is an element essential for the growth of animals and plants and is found as a constituent of teeth and bones. Like potassium, sodium is one of the most common elements constituting cells.

Sodium silicate may be used in an amount of 150 to 300 parts by weight based on 100 parts by weight of potassium carbonate. When sodium silicate is used in an amount below the lower limit, its effect is insufficient. On the other hand, if the amount of sodium silicate exceeds the upper limit, a problem with solubility arises.

Sodium thiosulfate useful in the present invention has 5 water molecules (pentahydrate), and is soluble in water, producing a characteristic salty taste, and its solubility in alcohol is negligible. It dissolves silver halides, such as silver chloride, and other silver salts. Sodium thiosulfate is generally used as a dechlorinating agent and a heavy metal chelator. In addition, it is used to neutralize the toxicity of major minerals, and to form multivalent cations, thus producing cationic alkaline minerals.

In the present invention, sodium silicate is used in an amount of 2 to 8 parts by weight based on 100 parts by weight of potassium carbonate. The effect of sodium silicate is insufficient at an amount below the lower limit while an amount exceeding the upper limit may cause a problem with equivalency.

Sodium carbonate functions to adjust potassium/sodium ratios in the composition, and makes a contribution to deodorization. Its amount is between 0.5 and 2 parts by weight, based on 100 parts by weight of potassium carbonate. If too small an amount is used, deodorization is problematic. On the other hand, an excessive amount of sodium carbonate is prone to breaking the balance between potassium and sodium.

As a source of sodium chloride useful in the present invention, solar salt is used. Solar salt is rich in various minerals. Solar salt is alkaline, with a salinity of about 88%. Abundant in calcium, magnesium, zinc, and iron, solar salt does not provide sodium alone, which may be prone to causing hypertension or obesity. In addition, solar salt acts as an antioxidant so as to increase immunity.

Suitable amounts of solar salt range 2 to 8 parts by weight, based on 100 parts by weight of potassium carbonate.

Potassium chloride is highly soluble in water to allow plants to readily absorb potassium. Hence, it helps soil maintain plant productivity. In addition, potassium chloride reduces the toxicity of toxic materials, aiding the growth of crops.

As needed, magnesium sulfate may be added to the composition. Magnesium is alkaline, with a bitter taste. In a human cell, the content of magnesium is ⅙ that of potassium. Like calcium and phosphorous, magnesium is a constituent of bones and teeth. Magnesium acts as a co-catalyst in cellular enzymatic reactions of carbohydrate metabolism.

Magnesium, together with calcium, can release sodium causative of hypertension or obesity, and acts as an antioxidant to enhance immunity. Further, it can act as a tranquilizer to calm intense emotions and to improve defense against stress. Deficiency of magnesium may cause muscular convulsions, depression, insomnia, tachycardia, arrhythmia, dyspepsia, hypertension, cardiac diseases, asthma, chronic fatigue, hypersensitive diseases, etc.

Potassium carbonate is suitably used in an amount of 0.1 to 0.3 parts by weight based on 100 parts by weight of potassium carbonate. The effect of potassium carbonate is not obtained at an amount less than the lower limit. Coagulation happens at an amount exceeding the upper limit.

White sugar ($C_{12}H_{22}O_{11}$) is degraded to neutralize toxicity and bitter tastes of ionic minerals and to prevent the ionic minerals from reverting to molecular states. Further, digests of white sugar converts inorganic materials into organic-like ionized materials, and converts inorganic minerals into organic minerals, like in the case of carbon dioxide assimilation, so that the organic minerals coexist in ionized states.

Thanks to white sugar, the anionic, alkaline complex mineral solution increases in viscosity, adsorptivity, preservability, and fermentability. Accordingly, when added to a formulated feed mixture or animal feed, the anionic, alkaline complex mineral solution adsorbs well into grain powder, composed of carbohydrates and vegetable proteins, or is well mixed therewith, thus preserving them and acting as a fermentation promoter. To effectively implement these functions, white sugar is used in an amount of 200 to 400 parts by weight, based on 100 parts by weight of potassium carbonate.

In an aqueous solution, silver thiosulfate ($Ag_2S_2O_3$), which is used as an option in the present invention, exists as $[Ag(S_2O_3^{2-})_2]^{3-}$ at a high concentration of $S_2O_3^{2-}$ and as $[Ag(S_2O_3^{2-})_6]^{10-}$ at a low concentration of $S_2O_3^{2-}$. In the present invention, silver thiosulfate, together with sodium thiosulfate ($Na_2S_2O_3$), forms a high concentration of multivalent anions, thus making the blood of animals alkaline and promoting the growth and activation of cells. For this, silver thiosulfate is used in an amount of $1\times10^{-3}$ to $8\times10^{-3}$ parts by weight, based on 100 parts by weight of potassium carbonate.

Embodiments of the present invention are described with reference to the accompanying drawings in order to describe the present invention in detail so that those having ordinary knowledge in the technical field to which the present invention pertains can easily practice the present invention. It should be noted that same reference numerals are used to designate the same or similar elements throughout the drawings. In the following description of the present invention, detailed descriptions of known functions and configurations which are deemed to make the gist of the present invention obscure will be omitted.

A better understanding of the present invention may be obtained through the following examples which are set forth to illustrate, but are not to be construed as limiting the present invention.

Preparation Example 1

In 500 L of pure water at 70~80° C., 5 kg of sodium thiosulfate, 1 kg of sodium carbonate 1 kg of potassium chloride, and 5 kg of sodium chloride (solar salt) were dissolved by stirring for 30 min. To this solution, 150 kg of potassium carbonate was added, and dissolved by stirring for 2 hrs. This process of addition and stirring for 2 hrs was also performed with 300 kg of sodium silicate and then with 450 kg of white sugar. As a result, 1412 kg of a complex mineral solution was obtained.

To this complex mineral solution was dropwise added a solution of silver thiosulfate in 1 L of water, followed by stirring for 30 min and fermentation for 12 hrs to obtain an immunostimulant complex solution (hereinafter referred to as "BARODON Chois Gold"). The silver thiosulfate was prepared by converting 5 g of silver nitrate into silver chloride, and reacting silver chloride with sodium thiosulfate.

A functional formulated feed mixture was obtained by adding BARODON Chois Gold at a rate in an amount of 0.005% (50 g), 0.01% (100 g), 0.02% (200 g), or 0.03% (300 g), based on 1,000 kg of a formulated feed mixture.

Preparation Example 2

112 kg of the nonspecific immunostimulant complex mineral solution BARODON Chois Gold prepared in Preparation Example 1 was mixed with 900 kg of a feed material (corn gemmule, soybean meal)) to give a solution for use as fermentation promoter and preserver. It was allowed to undergo a fermentation and drying process to give a functional fermented product in a powder form (hereinafter referred to as "BARODON-Ex") as a feed additive.

BARODON-EX may be added in an amount of 0.05% (500 g), 0.1% (1 kg) or 0.2% (2 kg) to 1,000 kg of a formulated feed mixture to give a functional formulated feed mixture that can be used as an additive for the following: defense against foot-and-mouth disease, vaccine potentiation, and productivity promotion in livestock raising farms.

Preparation Example 3

The same process as in Preparation Example 1 was repeated to afford a nonspecific immunostimulant solution (hereafter referred to "BARODON mineral solution"), except that 300 kg of potassium carbonate, 200 kg of white sugar, and 0.3 kg of magnesium sulfate were used and that a solution of silver thiosulfate in 2 L of water was dropwise added, and incubated for 12 hrs, the silver thiosulfate being prepared by converting 10 g of silver nitrate into silver chloride and dissolving the silver chloride in sodium thiosulfate. BARODON mineral solution may be used as an antibacterial agent substituting for an antibiotic, and as an additive for antibacterial products, antioxidant products, and functional cosmetics.

Example 1

Immunoassay Against Highly Pathogenic AIV

BARODON Chois Gold, prepared in Preparation Example 2, was diluted 1:1000 and 1:500, and used in challenge tests with highly pathogenic avian influenza virus AVI H5N1 in the Veterinary Medicine Institute, College of Veterinary Medicine, Seoul National University, and in the International Vaccine Institute (IVI).

Highly pathogenic AIV H5N1 as a test virus was obtained from the IVI, and inoculated into BALB/C mice 8 weeks old.

Test Method

1) Test for Defense From Highly Pathogenic AIV H5N1

(1) Test animals were grouped as follows.

Animals to be inoculated: 60 BALB/C mice 8 weeks old (see Table 1)

Test group and administration: 60 mice were divided into 5 groups of 12: two groups were provided with 1× (1:1000) and 2× solutions of BARODON Chois Gold (Preparation Example 1) in their daily water dosage, respectively. The 1× and 2× solutions were prepared by dissolving 1.45 g and 2.90 g of Barodon ChoiceGold in 1 L of water, respectively. The other 3 groups were allowed to drink water without BARODON (Table 1). Of these three groups, one was orally administered the antiviral agent TamiFlu (Roche) at a dose of 10 mg/kg/day for 5 days from 6 hours after challenge with AIV H5N1 (positive control) while another group was administered no therapeutic agents (negative control, no-administration-to-challenged-group). The other group was neither challenged with the virus nor administered therapeutics (no-administration-to-challenge-free-group.

Term of administration of BARODON Chois Gold: 4 weeks before challenge with virus to 7 days after challenge.

Considering natural death, 12 mice were allocated per group, with only 10 challenged with virus.

Administration of BARODON for a term ranging from 4 weeks before challenge to 1 week after challenge.

TABLE 1

Mouse Groups for Testing Immunostimulant Effect of Borodon ChoiceGold of Viral Challenge

| Test Group | No. of Mice | Description | Note |
|---|---|---|---|
| Viral Challenge after administration | 12 | Challenged with virus 4 weeks after administration at 1 dose/day | BARODON Chois Gold Solution |
| | 12 | Challenged with virus 4 weeks after administration at 2 doses/day | BARODON Chois Gold Solution |
| Control/Viral Challenge | 12 | Challenged with virus/no administration | |
| Treatment/ Viral Challenge | 12 | Treatment with TamiFlu for 5 days after viral challenge | |
| Control/no administration | 12 | No administration/no challenge | |

(2) Method of Challenge Inoculation

Mice administered test materials were intranasally challenged with 50 μl of highly pathogenic AIV H5N1 at a dose of 2 $LD_{50}$/head.

(3) Evaluation of Defense Efficacy

Evaluation was made of defense efficacy by measuring mortality and body weight for 2 weeks after challenge.

Test Result and Analysis

1. Test of BARODON Chois Gold for Defense Against Highly Pathogenic AIV H5N1 and Examination of Change in Immune Cells 1) Survival Rate of BARODON Chois Gold-Administered Groups After Challenge As described above, 50 BALB/C mice 8 weeks old were divided into 5 groups of 10, and two groups were administered 1× (1:1000 dilution) and 2× (1:500 dilution) of BARODON Chois Gold every day for 4 days, respectively. Subsequently, 50 μl of highly pathogenic H5N1 AIV(100 $MID_{50}$/head) was intranasally challenged to each of the mice that were then observed for 2 weeks. BARODON was administered by 1 week after the challenge. The other three groups were used as control groups without administration with BARODON. Of them, one was administered the antiviral agent TamiFlu for 5 days from immediately after the challenge while another was not treated with any therapeutic (no administration/challenge group). The other group was neither challenged with the virus nor administered therapeutics (no-administration/no challenge group, Table 1).

As can be seen in FIG. 1, the no administration/challenge group started to die from day 9 (D9) after challenge and survived at a rate of about 67% by D12 while the survival rate increased to 75% in the TamiFlu-treated group, to 83% in the 1× BARODON group, and to 91% in 2× BARODON group. For comparison, the no administration/challenge group was 100% alive (FIG. 1).

Figure 2:
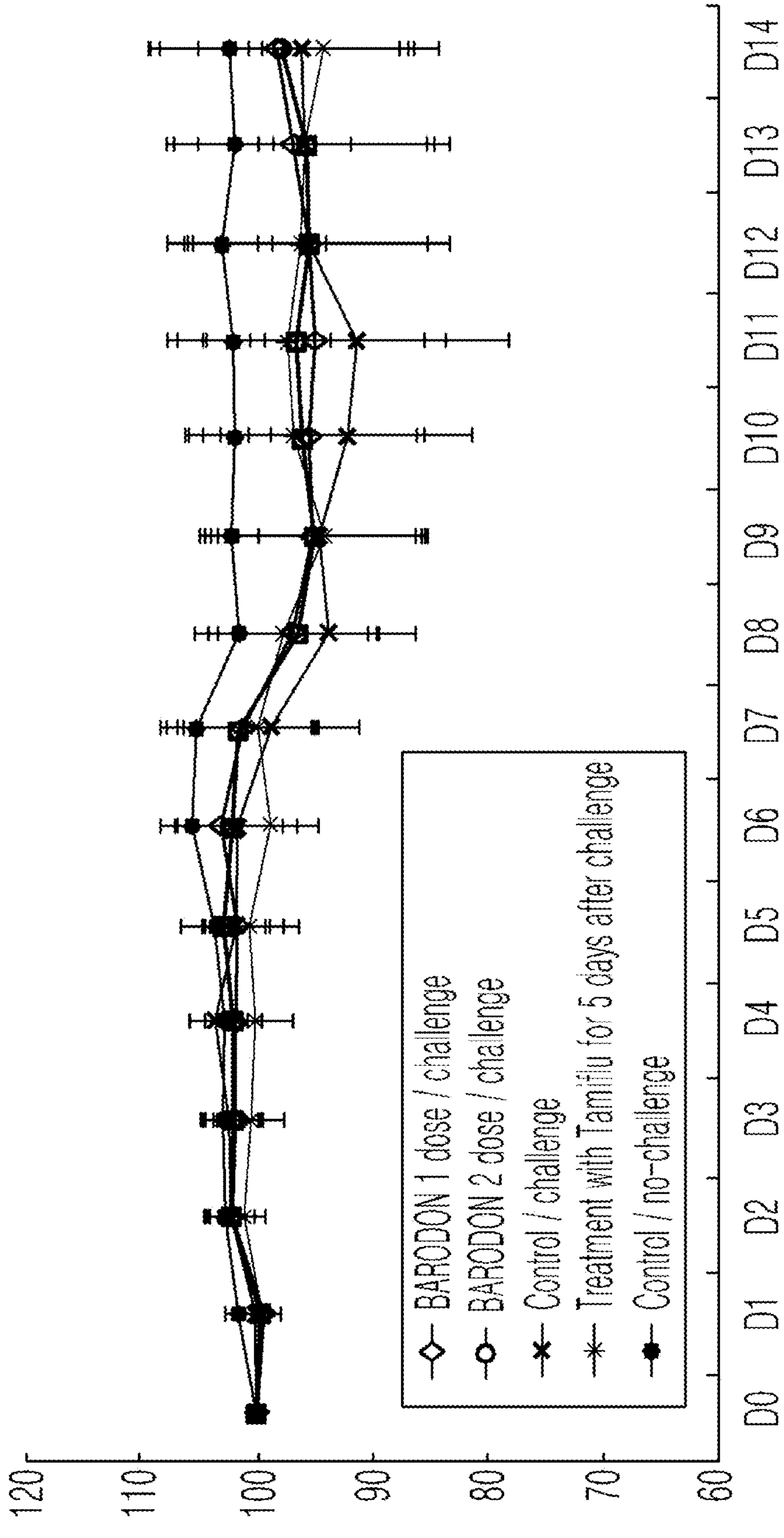
FIG. 2 is a graph showing the effect of BARODON Chois Gold on weight change with challenge with highly pathogenic AIV H5N1.

2) Change of Body Weight of BARODON Chois Gold-Administered Groups After Challenge Comparison was made of body weights of mice before and after challenge. The challenge group after treatment with BARODON or TamiFlue was lower in body weight over the overall period of time, compared to the no administration/no challenge group, with no difference in weight change between groups (FIG. 2). Hence, the effect of BARODON was not regarded significant in terms of weight change alone.

Figure 3:
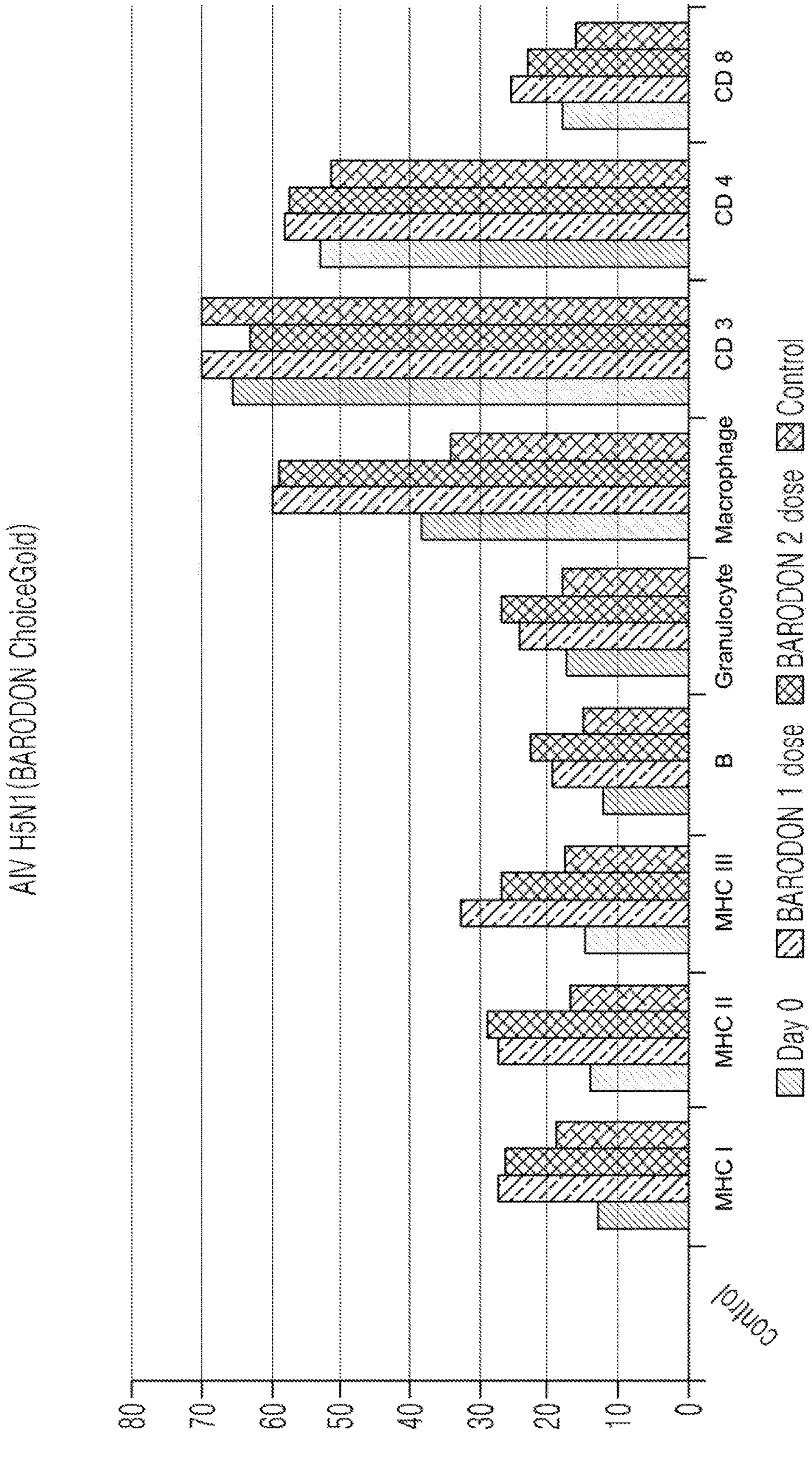
FIG. 3 is a graph showing the distribution and expression of immune cells in mice fed BARODON Chois Gold-supplemented diet (Day 0: measured immediately before administration with BARODON Chois Gold, and BARODON 1 dose, BARODON 2 dose, and no administration controls: measured 4 weeks after administration)

3) Analysis of Subpopulation of Leukocytes in BARODON Chois Gold-Administered Group Blood samples were taken from each mouse test group before BARODON administration and 4 weeks after BARODON administration (immediately before challenge with AIV), and examined for immune cell subpopulations. In this experiment, blood obtained from three mice was set as one sample because the amount of blood sampled from 8-week-old mice was too small to analyze for leukocyte subpopulations. Accordingly, the number of samples was insufficient for statistical confirmation, but tendency could be analyzed. As is apparent from data of Table 2 and FIG. 3, the groups administered BARODON Chois Gold 1× or 2× solution for 4 weeks tended to increase in the density of MHC class I, MHC class II, B cell, granulocyte, macrophage, CD4, and CD8, compared to the group before administration or no-administration controls, while there was no difference in CD3 between groups. In addition, there was a tendency toward greater populations of immune cells in the BARODON Chois Gold-administered groups, compared to the control group that was administered the drug.

Comparing between groups administered BARODON Chois Gold, B cells and granulocytes tended to increase in a dose-dependent manner whereas none of MHC class I, MHC class II, macrophages, CD4, and CD8 exhibited dose-dependent increase in population or expression level.

TABLE 2

Change in Immune Cell Population in Mice after intake of BARODON Chois Gold for 4 Weeks (%)

| | MHC class I | MHC class II | B cell | Granulocyte | Macrophage | CD3 | CD4 | CD8 |
|---|---|---|---|---|---|---|---|---|
| Day 0 | 12.42 | 13.93 | 11.93 | 17.20 | 37.99 | 65.69 | 52.69 | 17.74 |
| BARODON 1X | 26.92 | 26.52 | 19.52 | 23.72 | 59.92 | 70.02 | 57.92 | 25.32 |
| BARODON 2X | 26.20 | 28.50 | 22.50 | 26.70 | 58.20 | 63.00 | 57.30 | 22.50 |
| Control ingredient* | 24.74 | 23.44 | 16.24 | 21.34 | 54.64 | 66.64 | 58.44 | 18.04 |
| Control/No administration | 18.70 | 16.40 | 14.70 | 18.05 | 34.00 | 70.10 | 51.30 | 15.70 |

*Control ingredient: commercially available immunostimulant ($Al_2SiO_5$-based, granular immunostimulant, manufactured by S company)

2. Efficacy of Defense Against Highly Pathogenic AIV H5N1 and Examination of Immune Cell Population In a test for defense from highly pathogenic AIV, the survival rate of mice was measured to be 67% in the no-administration groups, 75% in the TamiFlu-treated group, 83% in the BARODON 1×-administered group, and 91% in the BARODON 2×-administered group, indicating the superiority of Borodon to TamiFlu in defense effect, but there was no significance. However, none of the groups treated with TamiFlu and BARODON exhibited weight gain after challenge, so that there was no significance for defense efficacy.

Turning now to a change in immune cell population, although the number of test mice and the amount of blood samples therefrom were insufficient for statistical significance, all of the mice treated with BARODON Chois Gold 1× and 2× solutions for 4 weeks were observed to increase in the density of the major immunological factors MHC class I, MHC class II, B cell, granulocyte, macrophage, CD4, and CD8, compared to the no-administration controls. In contrast, no differences in CD3 were found between groups. In addition, there was a tendency toward greater populations of immune cells in the BARODON Chois Gold-administered groups, compared to the control group that was administered the control drug. Comparing between groups administered BARODON Chois Gold, B cells and granulocytes tended to increase in a dose-dependent manner.

Example 2

Test for Disease Resistance of Farmed Fish (Fry)

Effects of diets supplemented with BARODON Chois Gold prepared in Preparation Example 1 on the growth, feeding efficiency, nonspecific immunity and disease resistance of juvenile olive flounder were examined in a laboratory of the College of Ocean Sciences, Jeju National University, Korea.

1. Material and Method 1.1. Experimental Diet

Figure 4:
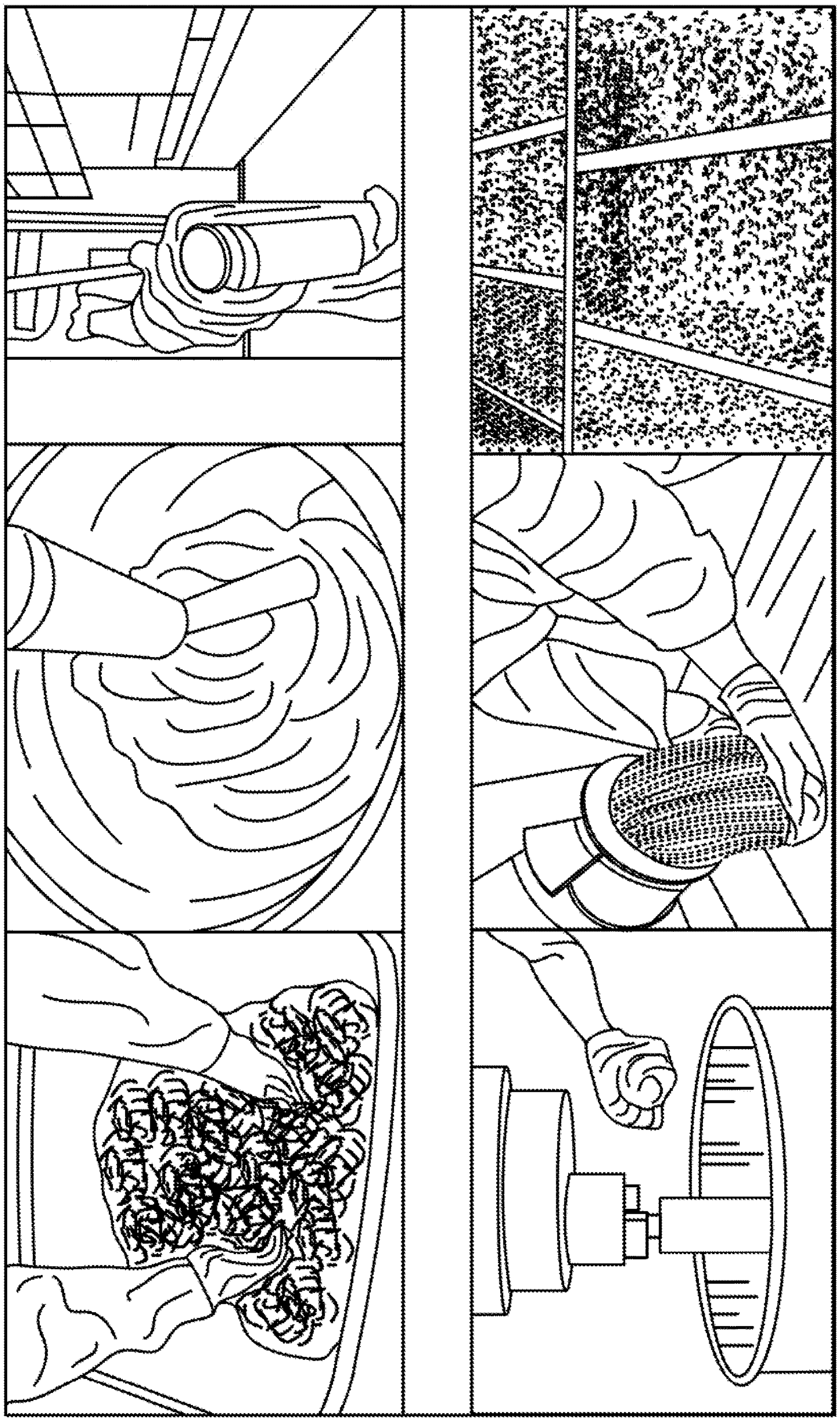
FIG. 4 shows photographs to illustrate preparation processes of the experimental diet.

A total of 7 diets were prepared with the same crude protein content (42%) and energy (17.7 MJ/kg diet). Compositions and ingredients of the basal diet are summarized in Tables 3 and 4. For experimental diets, the Barodon-free basal diet was used, or added with BARODON Chois Gold (BARODON-1× (0.01%), 2× (0.02%), 3× (0.03%), 4× (0.04%), and 5× (0.05%)), or with 200 ppm of a Rovithai product. For the preparation of experimental diets, all diet sources were pulverized into powders that were significantly homogeneous in size, and accurately weighed before being mixed together. The mixture was blended with predetermined amounts of the BARODON solutions, together with distilled water in an amount of 30% by weight based on the total weight of the mixture. The resulting blends were extruded into pellets 3-mm in diameter, using a chopper machine (SMC-12, Kuposlice, Busan, Korea) (see FIG. 4). The pellets were dried for 1-2 days with electric fans, and sieved to a suitable size, followed by storage at −20° C. in a refrigerator until use.

TABLE 3

Composition of the basal diet for juvenile olive flounder (% dry matter basis)

| ingredients | % |
|---|---|
| White fish meal | 50.0 |
| Soybean meal | 6.0 |
| Corn gluten meal | 6.0 |
| Wheat flour | 24.0 |
| Squid liver oil | 11.0 |
| CMC | 1.0 |
| Mineral mix[1] | 1.0 |
| Vitamin mix[2] | 1.0 |

[1]$MgSO_4 \cdot 7H_2O$, 80.0; $NaH_2PO_4 \cdot 2H_2O$ 370.0; KCl, 130.0; Ferric citrate, 40.0; $ZnSO_4 \cdot 7H_2O$ 20.0; Ca-lactate 365.5; CuCl 0.2; $AlCl_3 \cdot$6H2O 0.15; $Na_2Si_2O_3$ 0.01; $MnSO_4 \cdot H_2O$ 2.0; $CoCl_2 \cdot 6H_2O$ 1.0

[2]L-ascorbic acid 121.2; DL-α tocopheryl acetate 18.8; thiamin hydrochloride 2.7; riboflavin 9.1; pyridoxine hydrochloride 1.8; niacin 36.4; Ca-D-pantothenate 12.7; myo-inositol 181.8; D-biotin 0.27; folic acid 0.68; p-aminobenzoic acid 18.2; menadione 1.8; retinyl acetate 0.73; cholecalficerol 0.003; cyanocobalamin 0.003

TABLE 4

Proximate analysis of the seven experimental diets

| Diet | Dry Matter (%) | Protein (% DM) | Lipid (% DM) | Ash (% DM) |
|---|---|---|---|---|
| Control | 89. | 47.1 | 15.2 | 11.0 |
| BARODON-1X (BARODON 0.01%) | 89. | 46.5 | 15.2 | 11.0 |
| BARODON-2X (BARODON 0.02%) | 89. | 47.1 | 15.4 | 11.0 |
| BARODON-3X (BARODON 0.03%) | 89. | 47.1 | 15.5 | 11.0 |
| BARODON-4X (BARODON 0.04%) | 89.2 | 46.1 | 15.2 | 11.0 |
| BARODON-5X (BARODON 0.05%) | 89.1 | 46.9 | 15.0 | 11.0 |
| Rovithai | 89.2 | 46.8 | 15.2 | 11.0 |

1.2. Fish and Breeding

Figure 5:
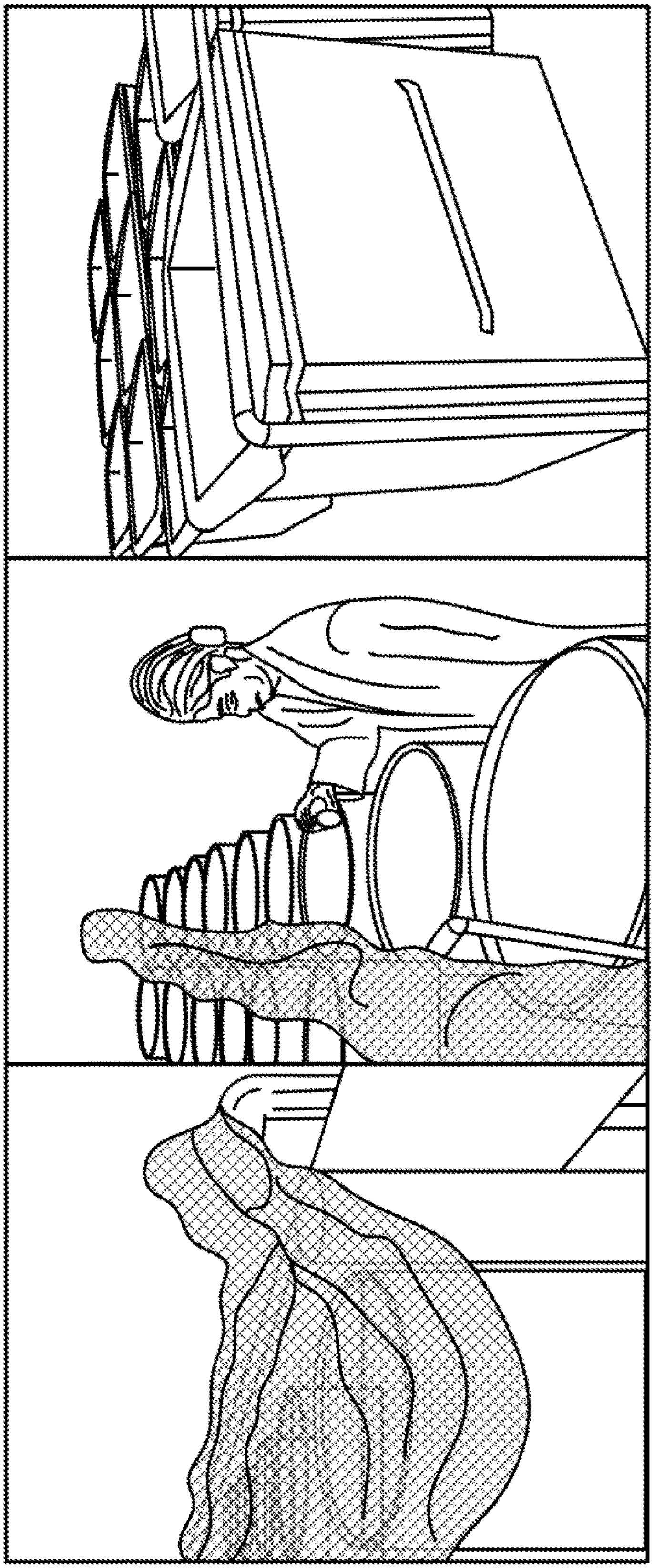
FIG. 5 shows photographs to illustrate tanks for raising aquatic organisms.

Juvenile olive flounder to be tested were transported from a private hatchery (Dong Won Fisheries Co., Jeju Island, Korea) to the Marine and Environmental Research Institute of Jeju National University. They were acclimated to the experimental conditions of 3-ton FRP water tanks for 2 weeks while being fed with a commercially available diet. The experimental water tanks used in this experiment are shown in FIG. 5. After pre-breeding, juvenile olive flounder (average weight: 26 g) were randomly introduced into a total of 21 200-L cylindrical tanks, with the allocation of 45 fishes to each tank. A flow-through system was used to provide sand-filtered seawater at a flow rate of 3 L/min for the tank. To maintain a predetermined level of dissolved oxygen in the tanks, aeration was provided by air stones. The photoperiod was maintained on a 12:12 light: dark schedule using a fluorescent lamp. The rearing water temperature was naturally maintained at 21° C. to 27° C. over the experiment period. The fishes were fed to satiety twice daily (09:00 and 18:00 o'clock) for 10 weeks. Fish growth was measured at 3-week intervals. All fishes were starved for 24 h prior to handling for weighing.

1.3. Sampling, Biochemical Analysis, and Challenge Inoculation

Figure 6:
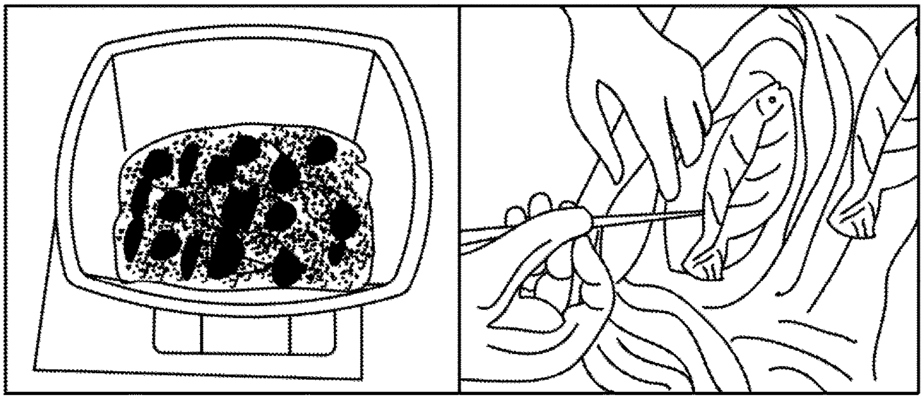
FIG. 6 shows photographs to illustrate the identification of aquatic organism growth, and the blood sampling.

After feeding for 10 weeks, the final weight of fish was measured to calculate weight gain, specific growth rate, feed conversion ratio, protein efficiency ratio, and survival. From each tank, 10 fishes were randomly selected, anesthetized with 2-phenoxyethanol (200 ppm), followed by sampling blood from the caudal vein with the aid of a disposable syringe (FIG. 6). Blood samples collected from 6 fishes (18 per test group) were heparinized for use in measuring hematocrit, hemoglobin and nitro blue tetrazolium (NBT) activity. Blood from 4 fishes (out of 12 per test group) was centrifuged to separate sera for use in analyzing lysozyme, myeloperoxidase, anti-protease, total immunoglobulin, glutathione peroxidase (GPx), and superoxide dismutase (SOD) activities. The fishes from which blood samples were taken were stored at −60° C. for other analysis.

The proximate composition of experimental diets was performed as described by AOAC (1995). Moisture content was determined by drying the samples in an oven (125° C. for 3 h). Crude ash was determined by burning the samples in the muffle furnace (550° C. for 12 h), and protein was calculated using the Kjeltec system (2300 Kjeltec Auto Distillation Unit, Foss Tecator, Sweden). Crude fat content was determined by ether extraction using Soxhlet system (Soxhlet Heater System C-SH6, Korea).

The hematocrit was determined by loading blood to heparinized micro-hematocrit capillary tubes and centrifuging them in Micro Hematocrit VS-12000 (Vision Scientific, Korea). Concentration of hemoglobin was determined by reacting with a commercially available kit reagent, and analyzing with a hemato-biochemical analyzer (Express plus system, Bayer, USA).

Oxidative radical production by neutrophils during respiratory burst was measured by the nitro-blue-tetrazolium (NBT) assay described by Kumari and Sahoo (2005). Briefly, blood (whole blood) and NBT (0.2%) were mixed in equal proportions (1:1) and incubated for 30 min at 25° C. Then, 50 μL was removed and dispensed into glass tubes. Next, 1 mL of dimethyl formamide was added to reduce the formation of formazan, and the tubes were centrifuged at 2,000×g for 5 min. Finally, the optical density of each supernatant was measured at 540 nm using a spectrophotometer (Genesys 10 UV, Rochester, N.Y., USA). Dimethylformamide was used as a blank.

Serum myeloperoxidase activity was measured as described by Kumari and Sahoo (2005). Briefly, 20 μL of serum was diluted with 80 μl of Hanks Balanced Salt Solution (HBSS, Sigma) in each well of 96-well plates. Then, 3,3',5,5'-tetramethylbenzidine hydrochloride (TMB, 20 mM) (Sigma) and $H_2O_2$ (5 mM) were added. After 2 min of the color change reaction, 35 μL of 4 M sulfuric acid was added to stop the reaction. Finally, optical density was read at 450 nm in a microplate reader.

A turbidometric assay was used to determine serum lysozyme activity using the method described by Yeh et al. (2008) with slight modifications. Briefly, lyophilized *Micrococcus lysodeikticus* (Sigma, USA) was suspended in sodium phosphate buffer (pH 6.2, 0.05 M) to give a 0.2 mg/ml suspension. Then, 200 μL of the suspension was placed in each well of 96-well plates, and 10 μL of serum isolated from the fishes was added. The reduction in absorbance of samples was determined at 570 nm in a microplate reader (UVM 340, Biochrom, Cambridge, UK) after a room temperature incubation for 1 and 6 min. One unit of lysozyme was defined as an amount of lysozme needed to catalyze a decrease in absorbance at 530 nm of 0.001/min.

Serum anti-protease activity was measured according to the method described by Ellis (1990) with slight modifications. Briefly, 20 μL of serum was incubated with 20 μL of standard trypsin solution (Type II-S, from porcine pancreas, 5 mg/mL, Sigma-Aldrich) for 10 min at 22° C. Then, 200 μL of phosphate buffer (0.1 M, pH 7.0) and 250 μL azocasein (2%) (Sigma) were added and incubated for 1 h at 22° C. Five hundred microliters of trichloro acetic acid (TCA, 10%) was added and incubated for 30 min at 22° C. The mixture was centrifuged at 6,000×g for 5 min, and 100 μL of the supernatant was transferred to 96-well microplates containing 100 μL of 1 N NaOH. Optical density was read at 430 nm.

Plasma total immunoglobulin (Ig) level was determined according to the method described by Siwicki and Anderson (1993). Briefly, plasma total protein content was measured using a micro protein determination method (C-690; Sigma) after immunoglobulin molecules were precipitated using a 12% polyethylene glycol solution (Sigma).

Serum glutathion peroxidase (GPx) levels were analyzed using GPx kit (Biovision, Inc. California, USA). Cumene hydroperoxide was used as a peroxide substrate (ROOH), and reacted with NADPH (b-Nicotinamide Adenine Denucleotide Phosphate, Reduced) in the presence of glutathione reductase (GSSG-R). To 50 μl of a sample was added 40 μl of the mixture, followed by incubation for 15 min. Again, 10 μl of cumene hydroperoxide was added before absorbance at 340 nm was read on a microplate reader.

Serum superoxide dismutase (SOD) activity was analyzed using an SOD kit (Fluka, 19160).

Streptoccosis, a general name for a variety of diseases caused by a group of bacteria called *Streptococcus*, is apt to break out in fishes in high-temperature seasons, e.g., summer to autumn, resulting in significant damage to juvenile to adult fishes. Infectious signs of *S. iniae* are reported to include prolapsed rectum, exophthalmos, corneal opacity, hyperemia of eye, focal hemorrhage below gills, and excessive secretion of mucus on gills and body surface. Streptococci infect olive flounder, tilapia, rainbow trout, and yellow tail, causing tremendous economic losses.

Figure 7:
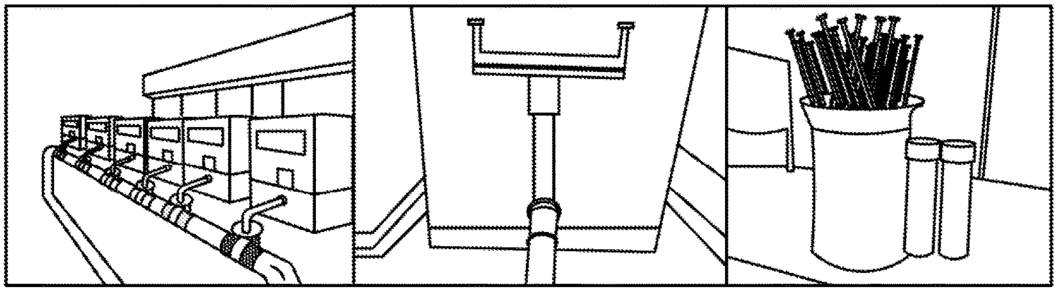
FIG. 7 shows photographs to illustrate a load test against streptococci (challenge test)
Figure 8:
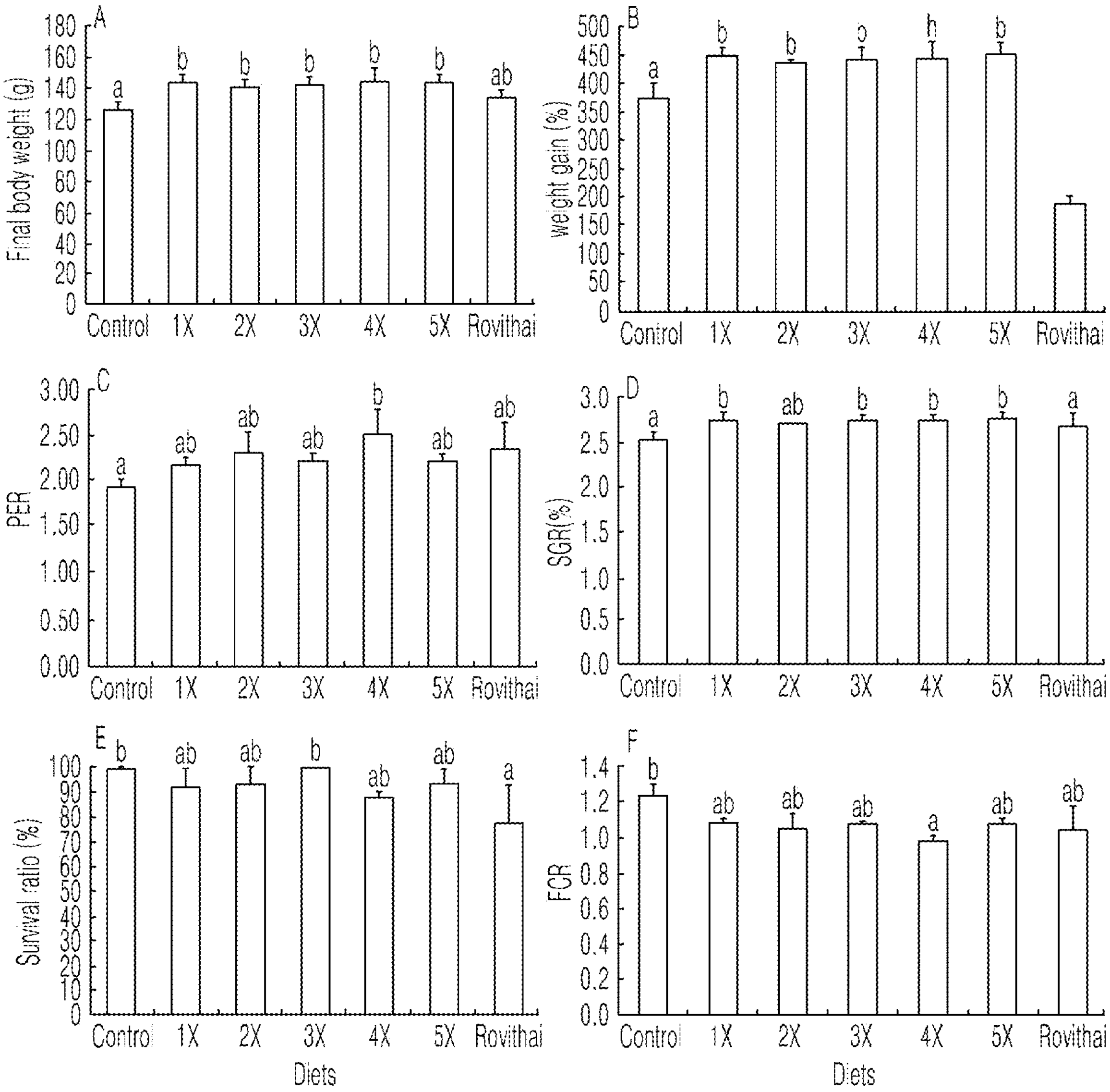
FIG. 8 shows graphs of the growth of juvenile olive flounder fed for 10 weeks with 7 experimental diets ((A) final weight, (B) weight gain, (C) protein efficiency ratio, (D) specific growth rate, (E) survival, (F) feed conversion rate)

After completion of the 10-week growth experiment, examination was made of the effect of BARODON on the resistance of olive flounder to Streptoccosis. The fishes left after blood sampling were intraperitoneally injected with a suspension of *S. iniae*. The pathogenic bacteria was collected after being cultured in a TSA medium at 25° C. for 24 hrs, and a suspension of *S. iniae* was intraperitoneally injected at a dose of 100 μl ($10^9$ CFU/ml) into olive flounder (FIG. 7). All groups were maintained in water of 22-25° C., with a dissolved oxygen level provided therefor, and 100% recovered every day. Over a total of 34 days, they were monitored for death.

1.4. Statistical Analysis

All the diets were assigned by a completely randomized design. Growth and analysis data were analyzed using One-way ANOVA in SPSS program (Version 12.0). Statistical significance was determined at 5% (p≤0.05) using Tukey's HSD. Data are expressed as mean±SD, and percentage data were arcsine transformed before analysis.

2. Result

Figure 9:
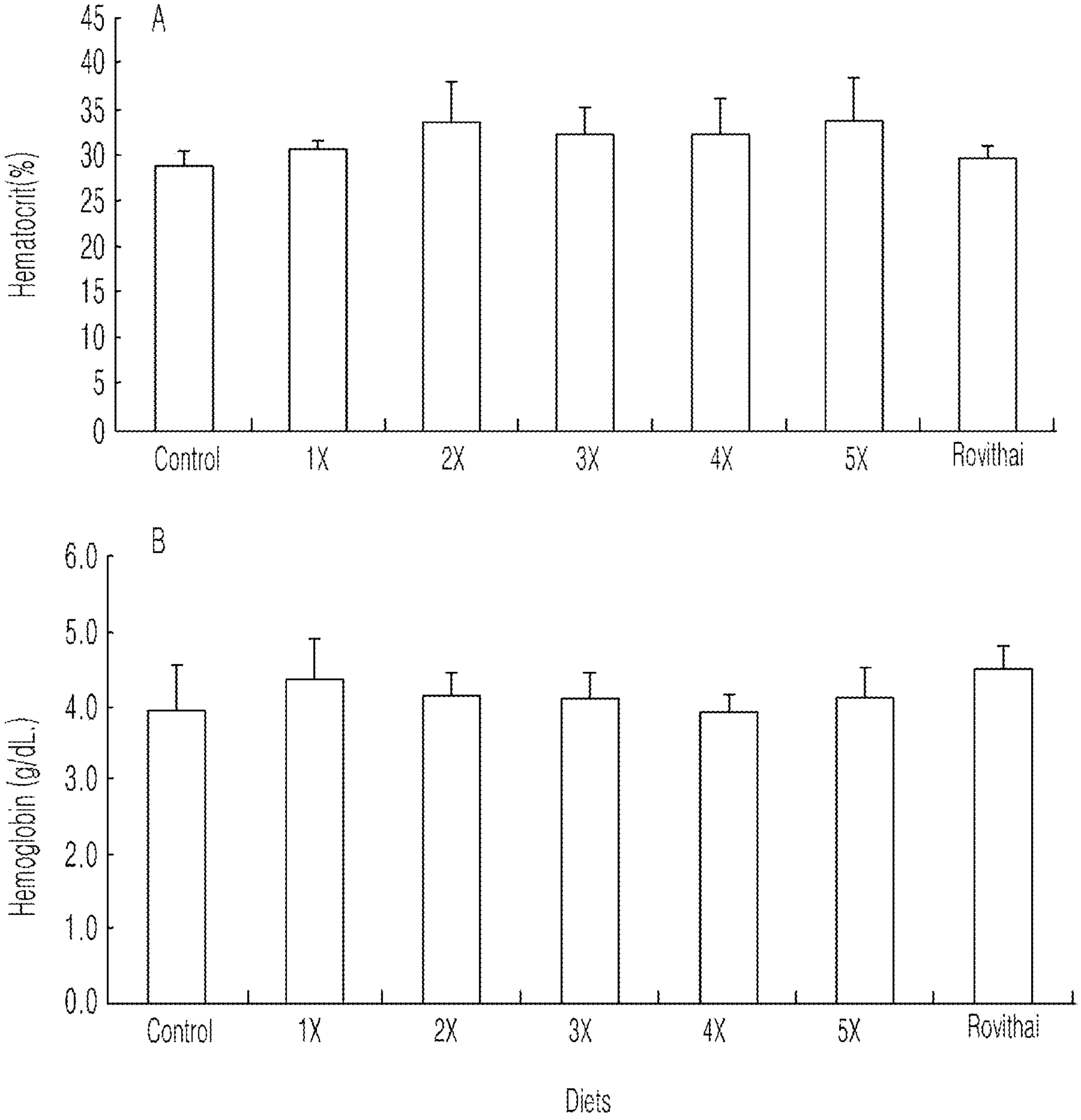
FIG. 9 shows graphs of blood indices in juvenile olive flounder fed for 10 weeks with 7 experimental diets ((A) hematocrit, (B) hemoglobin)
Figure 10:
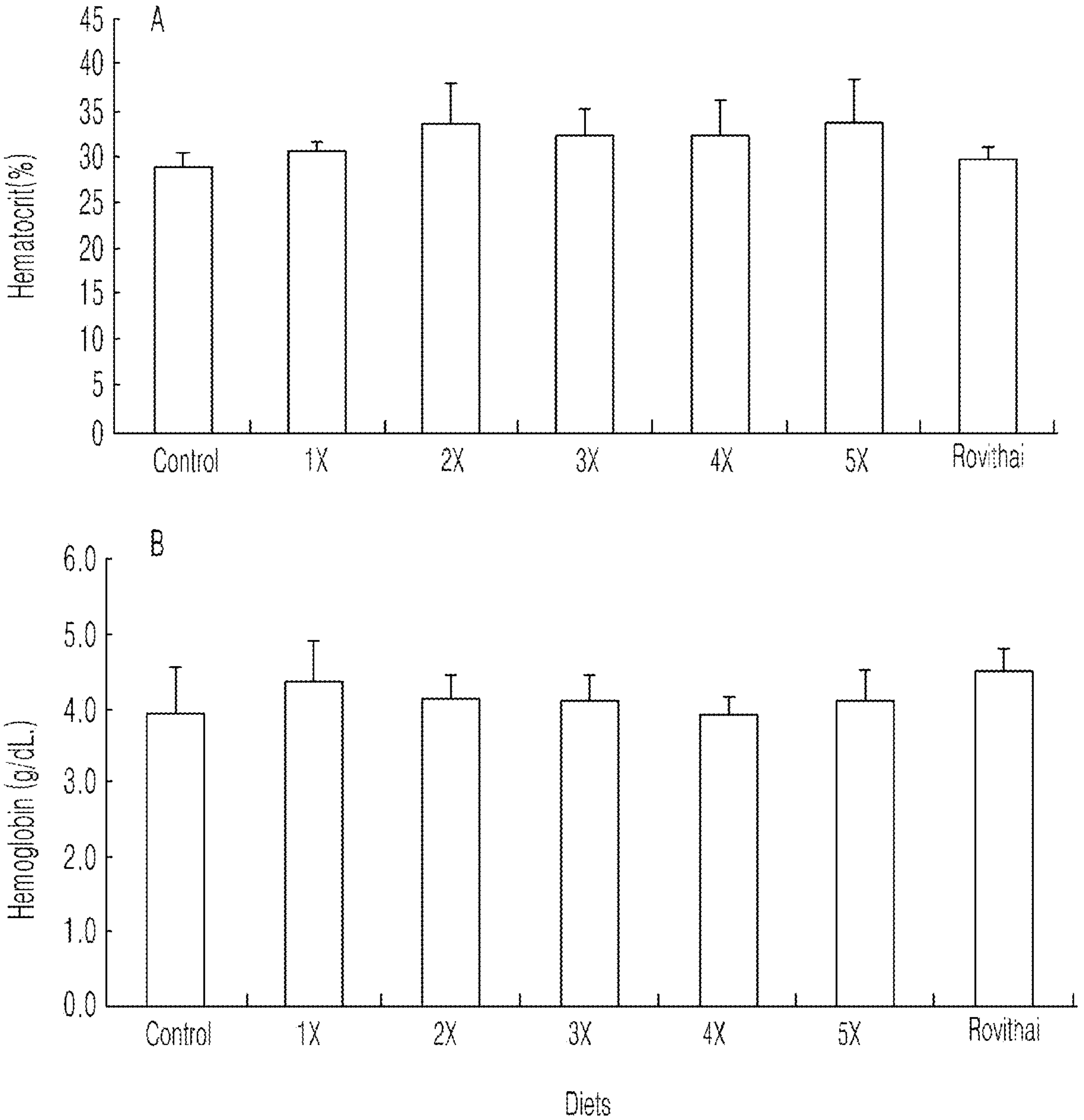
FIG. 10 shows graphs of blood analysis results in juvenile olive flounder fed for 10 weeks with experimental diets ((A) hematocrit, (B) hemoglobin)
Figure 11:
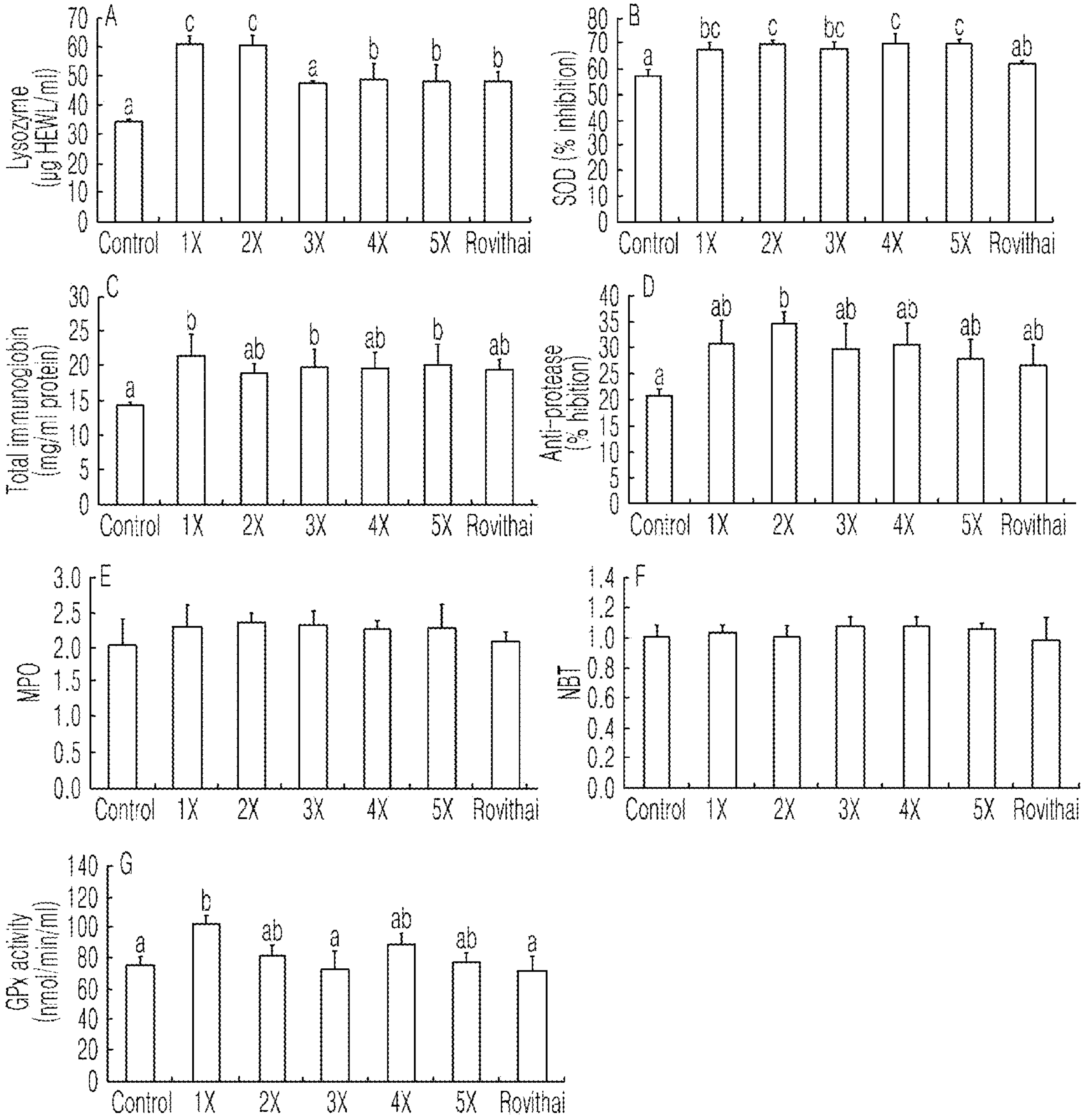
FIG. 11 shows graphs of nonspecific immune reactions in juvenile olive flounder fed for 10 weeks with 7 experimental diets ((A) lysozyme, (B) superoxide dismutase, (C) total immunoglobin, (D) antiprotease, (E) myeloperoxidase, (F) nitro blue tetrazolium (NBT), (G) glutathione peroxidase activity)

Results of the 10-week growth experiment are shown in Table 5 and FIG. 9. Weight gain and specific growth rate were increased by approximately 16% in the groups fed with diets supplemented with BARODON (BARODON 1× (0.01%), BARODON 2× (0.02%), BARODON 3× (0.03%), BARODON 4× (0.04%) or BARODON 5× (0.05%)), compared to the control, with significance. The group fed with BARODON 4× (0.04%) significantly increased in specific growth rate and protein efficiency ratio. A lower survival was observed in the Rovithai-fed group than the other group. Results of hematological assays of olive flounder after the 10-week feeding with experimental diets are summarized in Table 6 and FIG. 10. Hematocrit and hemoglobin, which are indices for general health, did not show a significant difference among dietary treatments. To examine effects of dietary supplementation of BARODON on nonspecific immunity, macrophage (NBT), myeloperoxidase (MPO), lysozyme, superoxide dismutase (SOD), anti-proteases, total immunoglobin, and gluthathione peroxidase (GPx) activities were analyzed (Table 7 and FIG. 11). These are representative analysis indices for nonspecific immunity in fishes. Significantly higher lysozyme activity was detected in BARODON-1× (0.01%) and 2× (0.02%) groups than in the other groups. SOD activity was observed to be high in BARODON-1× (0.01%), 2× (0.02%), 3× (0.03%), 4× (0.04%), and 5× (0.05%) groups, compared to the control, with significance. BARODON-1× (0.01%), 3× (0.03%), and 5× (0.05%) groups were significantly higher in total immunoglobulin activity than the control group. The BARODON-2× (0.02%) was higher in anti-protease activity than the control group, with significance. GPx activity was also significantly increased by BARODON-1× (0.01%) supplementation, compared to the control. However, no significant difference in MPO and NBT was found among dietary treatments.

Figure 12:
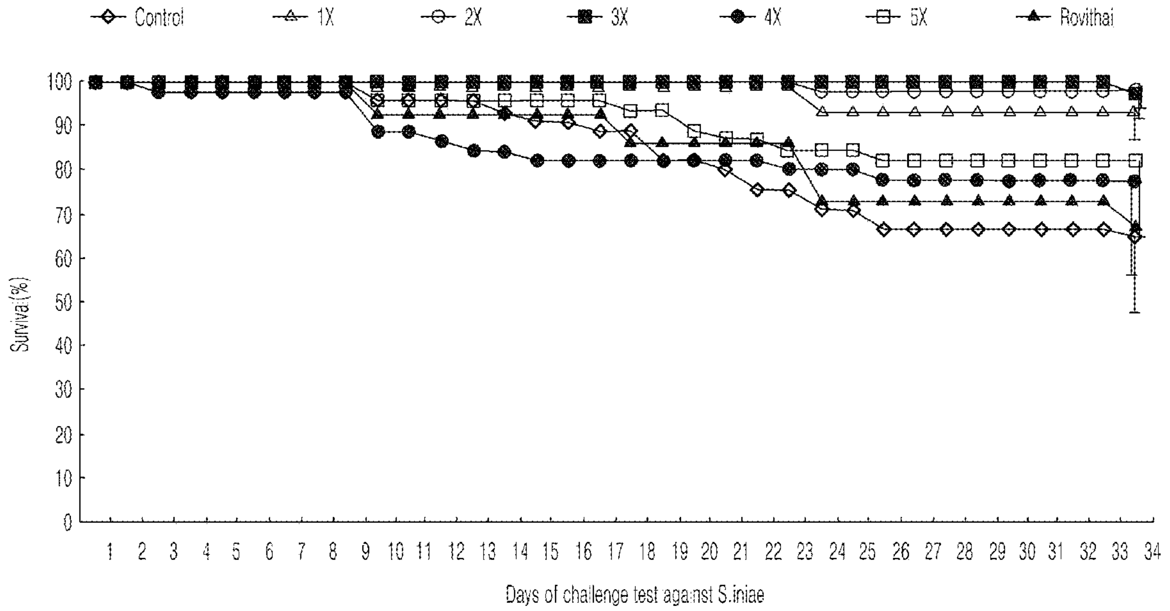
FIG. 12 is a graph showing the effect of BARODON on defense against *Streptococcus iniae*-induced mortality.

Results of challenge with streptococci are shown in FIG. 12. From 3 days post-infection, dead fishes started to appear. Since 20 days post-infection, the control groups of no administration were found to die at higher mortality than did the BARODON-treated groups. Mortality was measured to reach approximately 40% in the control groups, but to end up 10% or less in BARODON-1× (0.01%), 2× (0.02%), and 3× (0.03%) groups. As for the Rovithai group, its mortality was measured to be as high as that of the controls. These data, taken together, indicate that the dietary supplementation of BARODON at 1× (0.01%), 2× (0.02%), and 3× (0.03%) concentrations can increase the resistance of olive flounder to diseases caused by *S. iniae*.

TABLE 5

Growth performance of Juvenile olive flounder (initial BW: 26.5 g) fed seven experimental diets for 10 weeks

| | FBW[1] (g) | WG[2] (%) | SGR[3] (%) | Survival (%) | FCR[4] | F1[5] (g/fish) | PER[6] |
|---|---|---|---|---|---|---|---|
| Control | 125 ± 6.6$^{a}$ | 375 ± 28.4$^{a}$ | 2.32 ± 0.09$^{a}$ | 99.3 ± 1.3$^{b}$ | 1.23 ± 0.08$^{b}$ | 121.5 ± 1.9 | 1.94 ± 0.13$^{a}$ |
| BARODON-1X (BARODON 0.01%) | 145 ± 4.9$^{b}$ | 451 ± 14.9$^{b}$ | 2.55 ± 0.04$^{b}$ | 91.9 ± 1.5$^{ab}$ | 1.09 ± 0.02$^{ab}$ | 128.3 ± 6.0 | 2.21 ± 0.03$^{ab}$ |
| BARODON-2X (BARODON 0.02%) | 142 ± 2.1$^{b}$ | 436 ± 6.6$^{b}$ | 2.51 ± 0.02$^{ab}$ | 93.3 ± 8.0$^{ab}$ | 1.05 ± 0.10$^{ab}$ | 120.5 ± 13.4 | 2.29 ± 0.22$^{ab}$ |
| BARODON-3X (BARODON 0.03%) | 143 ± 4.5$^{b}$ | 445 ± 21.0$^{b}$ | 2.53 ± 0.06$^{b}$ | 100 ± 0.0$^{b}$ | 1.08 ± 0.01$^{ab}$ | 120.5 ± 5.8 | 2.21 ± 0.02$^{ab}$ |
| BARODON-4X (BARODON 0.04%) | 145 ± 7.7$^{b}$ | 447 ± 26.0$^{b}$ | 2.54 ± 0.07$^{b}$ | 87.4 ± 2.6$^{ab}$ | 0.99 ± 0.10$^{a}$ | 116.6 ± 7.4 | 2.48 ± 0.26$^{b}$ |
| BARODON-5X (BARODON 0.05%) | 145 ± 6.8$^{b}$ | 451 ± 23.0$^{b}$ | 2.55 ± 0.06$^{b}$ | 93.3 ± 5.9$^{ab}$ | 1.08 ± 0.03$^{ab}$ | 128.7 ± 10.7 | 2.21 ± 0.06$^{ab}$ |
| Rovithai | 134 ± 6.0$^{ab}$ | 191 ± 12.7* | 2.32 ± 0.09$^{a}$ | 77.2 ± 15.9$^{a}$ | 1.5 ± 0.14$^{ab}$ | 91.9 ± 10.7* | 2.33 ± 0.31$^{ab}$ |

Mean values of triplicate groups, values are presented as mean ± SD.
Values in the same column having different superscript letters are significantly different ($p < 0.05$).
[1]FBW: final body weight (g)
[2]Weight gain (%) = 100 × (final mean body weight − initial mean body weight)/initial mean body weight
[3]specific growth rate (%) = [(loge final body weight − loge initial body weight)/days] × 100
[4]Feed conversion ratio = dry feed fed/wet weight gain
[5]Feed intake = dry feed consumed (g)/fish
[6]Protein efficiency ratio = wet weight gain/total protein given
*Rovithai treatment was set up 3 weeks later than the others.

TABLE 6

Blood parameters of Juvenile olive flounder fed the seven experimental diets for 10 weeks. Mean values of triplicate groups are presented as mean ± SD. Values in the same column having different superscript letters are significantly different ($p < 0.05$)

| | Hematocrit (%) | Hemoglobin (g/dL) |
|---|---|---|
| Control | 28.8 ± 1.5 | 3.97 ± 0.6 |
| BARODON-1X (BARODON 0.01%) | 30.6 ± 1.0 | 4.37 ± 0.5 |
| BARODON-2X (BARODON 0.02%) | 33.6 ± 4.3 | 4.14 ± 0.3 |
| BARODON-3X (BARODON 0.03%) | 32.3 ± 3.0 | 4.11 ± 0.3 |
| BARODON-4X (BARODON 0.04%) | 32.1 ± 4.0 | 3.92 ± 0.2 |
| BARODON-5X (BARODON 0.05%) | 33.8 ± 4.4 | 4.10 ± 0.4 |
| Rovithai | 29.7 ± 1.3 | 4.49 ± 0.3 |

TABLE 7

Non-specific immune responses of Juvenile olive flounder fed the seven experimental diets for 10 weeks

| | Lysozyme (μg HEWL/ml) | SOD (% inhibition) | Total Immunoglobin (mg/ml protein) | Anti-protease (% inhibition) | MPO | NBT | GPx activity (nmol/min/ml) |
|---|---|---|---|---|---|---|---|
| Control | 34.1 ± 1.58$^{a}$ | 57.7 ± 2.9$^{a}$ | 15.3 ± 0.09$^{a}$ | 21.0 ± 1.35$^{a}$ | 2.04 ± 0.36 | 1.01 ± 0.07 | 75.0 ± 6.5$^{a}$ |
| BARODON-1X (BARODON 0.01%) | 61.2 ± 2.67$^{G}$ | 68.1 ± 2.39$^{b}$ | 21.4 ± 3.6$^{b}$ | 30.8 ± 4.57$^{ab}$ | 2.33 ± 0.30 | 1.03 ± 0.05 | 103 ± 1.9$^{b}$ |
| BARODON-2X (BARODON 0.02%) | 60.5 ± 3.39$^{G}$ | 70.7 ± 0.74$^{b}$ | 18.9 ± 1.2$^{ab}$ | 34.6 ± 2.20$^{b}$ | 2.36 ± 0.14 | 1.02 ± 0.07 | 81.9 ± 6.5$^{ab}$ |
| BARODON-3X (BARODON 0.03%) | 47.7 ± 0.85$^{b}$ | 68.4 ± 2.99$^{b}$ | 19.8 ± 2.9$^{b}$ | 29.7 ± 4.92$^{ab}$ | 2.34 ± 0.19 | 1.07 ± 0.04 | 73.4 ± 14.2$^{a}$ |
| BARODON-4X (BARODON 0.04%) | 49.0 ± 5.45$^{b}$ | 70.0 ± 4.36$^{b}$ | 19.6 ± 2.3$^{b}$ | 30.6 ± 4.37$^{ab}$ | 2.29 ± 0.08 | 1.09 ± 0.06 | 89.4 ± 6.7$^{ab}$ |
| BARODON-5X (BARODON 0.05%) | 48.1 ± 6.92$^{b}$ | 69.8 ± 2.66$^{b}$ | 20.0 ± 3.1$^{b}$ | 27.8 ± 3.90$^{ab}$ | 2.28 ± 0.35 | 1.06 ± 0.04 | 77.6 ± 6.2$^{ab}$ |
| Rovithai | 48.3 ± 3.4$^{b}$ | 62.3 ± 1.27$^{ab}$ | 19.2 ± 1.9$^{ab}$ | 27.0 ± 3.83$^{ab}$ | 2.09 ± 0.13 | 0.99 ± 0.15 | 72.0 ± 9.6$^{a}$ |

Mean values of triplicate groups are presented as mean ± SD.
Values in the same column having different superscript letters are significantly different ($p < 0.05$)

Example 3-1

Assay for Disease Resistance of Farmed Fish (Growth Period)

1. Material and Method 1.1. Experimental Diet

To examine the effect of dietary supplementation of BARODON on disease resistance, comparison was made between diets with BARODON Chois Gold and competitor's products (H diet, D diet). Experimental diets were prepared by spraying BARODON Chois Gold (Preparation Example 1) at 1× (0.01%) and 2× (0.02%) concentrations over Purina diet (control). For the same experiment condition, distilled water was sprayed at the same amount over the control, H diet, and D diet. Compositions of the basal diets are summarized in Table 8, below.

TABLE 8

Proximate analysis of five experimental diets

| Diets | Dry matter (%) | Protein (%, DM) | Lipid (%, DM) | Ash (%, DM) |
|---|---|---|---|---|
| Control | 90.3 | 58.3 | 10.7 | 14.0 |
| BARODON-1X (BARODON 0.01%) | 93.6 | 58.1 | 10.5 | 14.5 |
| BARODON-2X (BARODON 0.02%) | 93.8 | 57.9 | 10.4 | 14.5 |
| H Feed | 94.7 | 55.7 | 10.4 | 16.7 |
| D Feed | 79.4 | 58.8 | 13.0 | 9.1 |

1.2. Fish and Breeding

Figure 13:
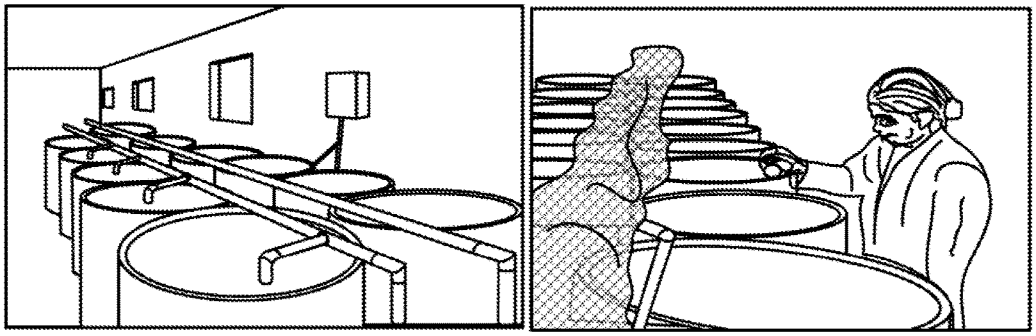
FIG. 13 shows photographs to illustrate tanks for raising aquatic organisms.
Figure 14:
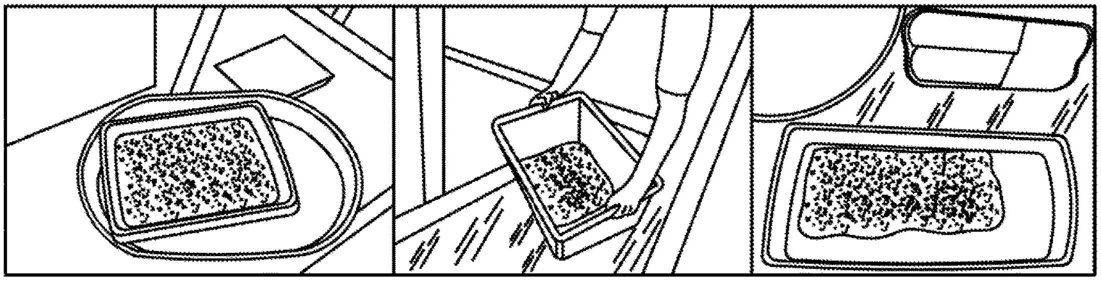
FIG. 14 shows photographs to illustrate the identification of aquatic organism growth.

Juvenile olive flounder to be tested were transported from a private hatchery (Dong Won Fisheries Co., Jeju Island, Korea) to the Marine and Environmental Research Institute of Jeju National University. They were acclimated to the experimental conditions of 8-ton FRP water tanks for 2 weeks while being fed with a commercially available diet. The experimental water tanks used in this experiment are shown in FIG. 13. After pre-breeding, olive flounder (average weight: 145 g) were randomly introduced into a total of 15 400-L cylindrical tanks, with the allocation of 25 fishes to each tank. A flow-through system was used to provide sand-filtered seawater at a flow rate of 4 L/min for the tank. To maintain a predetermined level of dissolved oxygen in the tanks, aeration was provided by air stones. The photoperiod was maintained on a 12:12 light:dark schedule using a fluorescent lamp. The rearing water temperature was naturally maintained at 21° C. to 27° C. over the experiment period. The fishes were fed to satiety twice daily (09:00 and 18:00 o'clock) for 15 weeks. Fish growth was measured at 3-week intervals. All fishes were starved for 24 h prior to handling for weighing.

1.3. Sampling, and Biochemical and Histopathological Analysis

Figure 15:
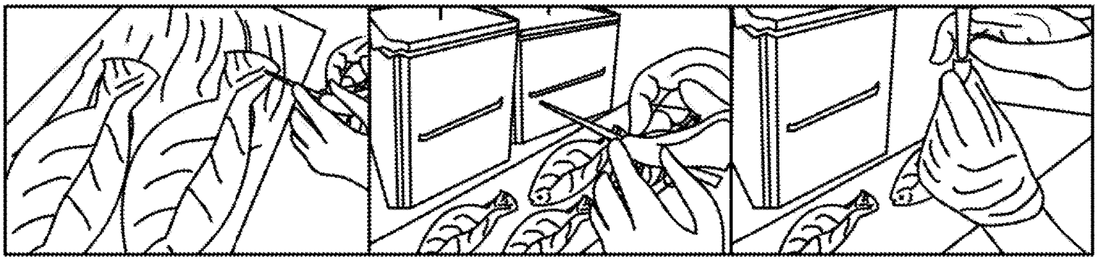
FIG. 15 shows photographs to illustrate blood sampling.

After feeding for 10 weeks, the final weight of fish was measured to calculate weight gain, specific growth rate, feed conversion ratio, protein efficiency ratio, and survival. From each tank, 3 fishes (9 per group) were randomly selected, anesthetized with 2-phenoxyethanol (200 ppm), followed by sampling blood from the caudal vein with the aid of a disposable syringe (FIG. 15). Blood samples were heparinized for use in measuring hematocrit, hemoglobin and nitro blue tetrazolium (NBT) activity. The fishes from which blood samples were taken were stored at −60° C. for other analysis. The proximate composition of experimental diets was performed as described by AOAC (1995). Moisture content was determined by drying the samples in the oven (125° C. for 3 h). Crude ash was determined by burning the samples in the muffle furnace (550° C. for 6 h), and protein was calculated using the Kjeltec system (2300 Kjeltec, Sweden). Crude fat content was determined by ether extraction using Soxhlet system (Soxhlet Heater System C-SH6, Korea) according to the method of Folch et al. (1959).

The hematocrit was determined by loading blood to heparinized micro-hematocrit capillary tubes and centrifuging them in Micro Hematocrit VS-12000 (Vision Scientific, Korea). Concentration of hemoglobin was determined by reacting with a commercially available kit reagent, and analyzing with a hemato-biochemical analyzer (Express plus system, Bayer, USA). Blood levels of hemoglobin, gluocose, total cholesterol, AST, and ALT were analyzed with respective commercially available kit reagents, using an automatic biochemistry analyzer (Express plus system, Bayer, USA).

Figure 16:
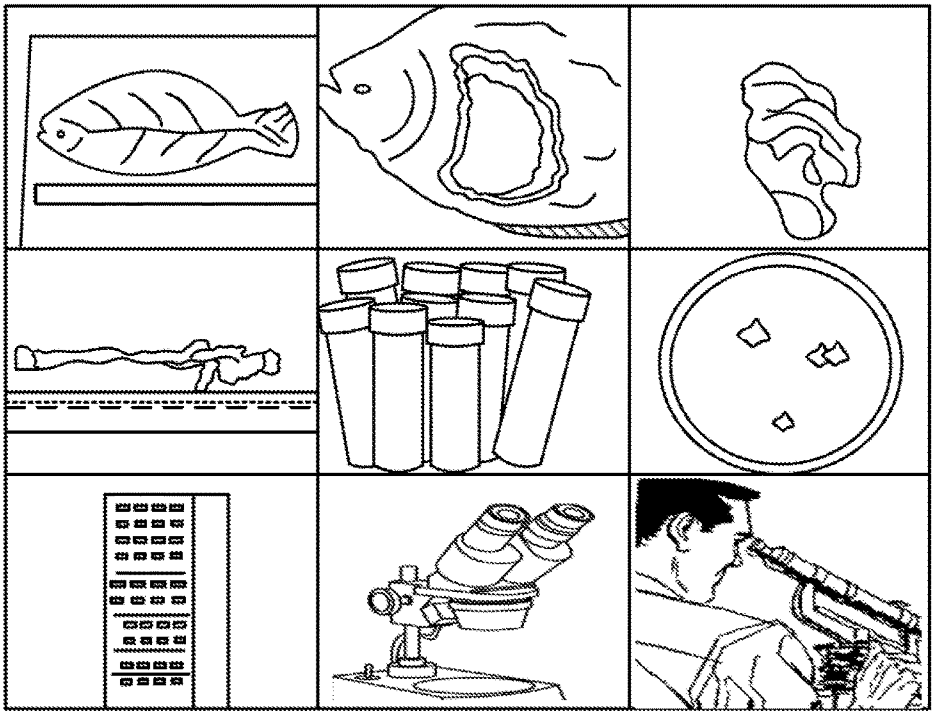
FIG. 16 shows photographs to illustrate histopathological analysis of olive flounder fed with 5 commercially available diets.
Figure 17:
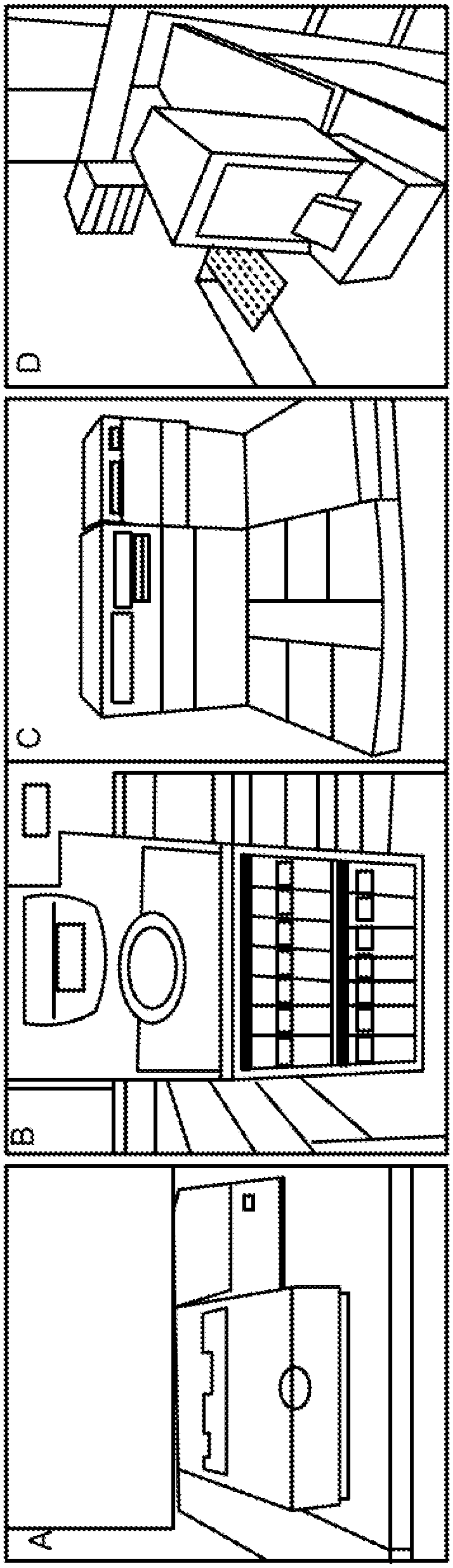
FIG. 17 shows photographs of tissue analyzing apparatuses ((A) side warmer, (B) tissue treatment apparatus, (C) tissue embedding device, (D) microtome 0.2)

After completion of the experiments, histological observation was made on the digestive organ. For this, 3 fishes per tank were randomly selected and anesthetized with 2-phenoxyethanol (200 mg/L), and dissected for measurement of hepatosomatic index (HIS) and relative length of gut (RLG). The intestine samples were fixed in Bouin's solution, embedded in paraffin, and cut into 3-4 mm-thick sections. The sections were stained with Alcian blue periodic acid-Schiff (AB-PAS), and 0.5% eosin before observation under an optical microscope. Histological observation was made on the intestine samples using a light microscope to examine the distribution and number of goblet cells found on the inner surface of the anterior intestine (FIGS. 16 and 17).

1.4. Statistical Analysis

All the diets were assigned by a completely randomized design. Growth and analysis data were analyzed using One-way ANOVA in SPSS program (Version 12.0). Statistical significance was determined at 5% ($p \leq 0.05$) using Tukey's HSD. Data are expressed as mean±SD, and percentage data were arcsine transformed before analysis.

2. Result

Figure 18:
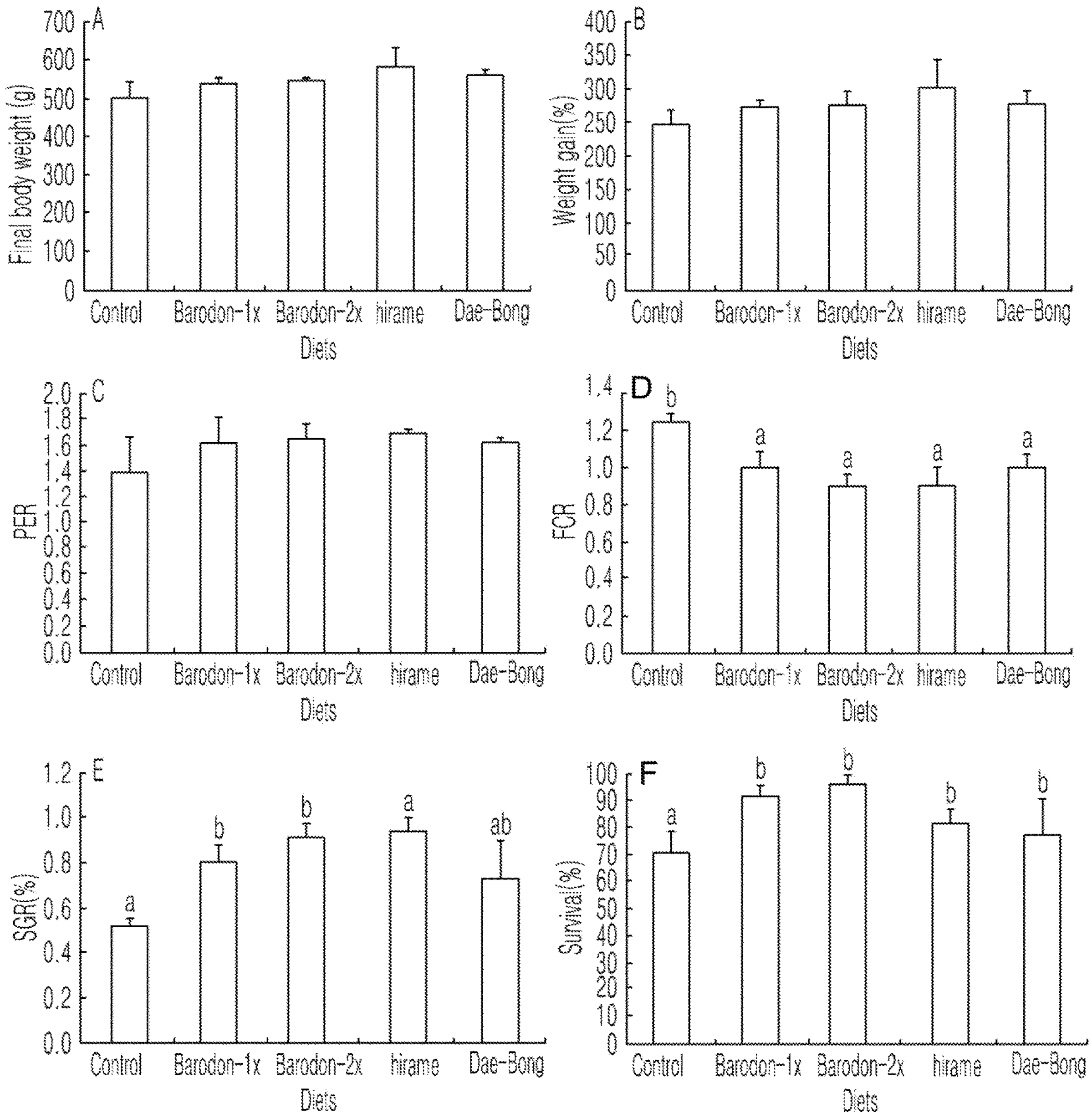
FIG. 18 shows photographs to illustrate growth rates of olive flounder fed for 15 weeks with 5 experimental diets ((A) final weight, (B) weight gain, (C) protein efficiency ratio, (D) feed conversion rate, (E) specific growth rate, (F) survival)
Figure 19:
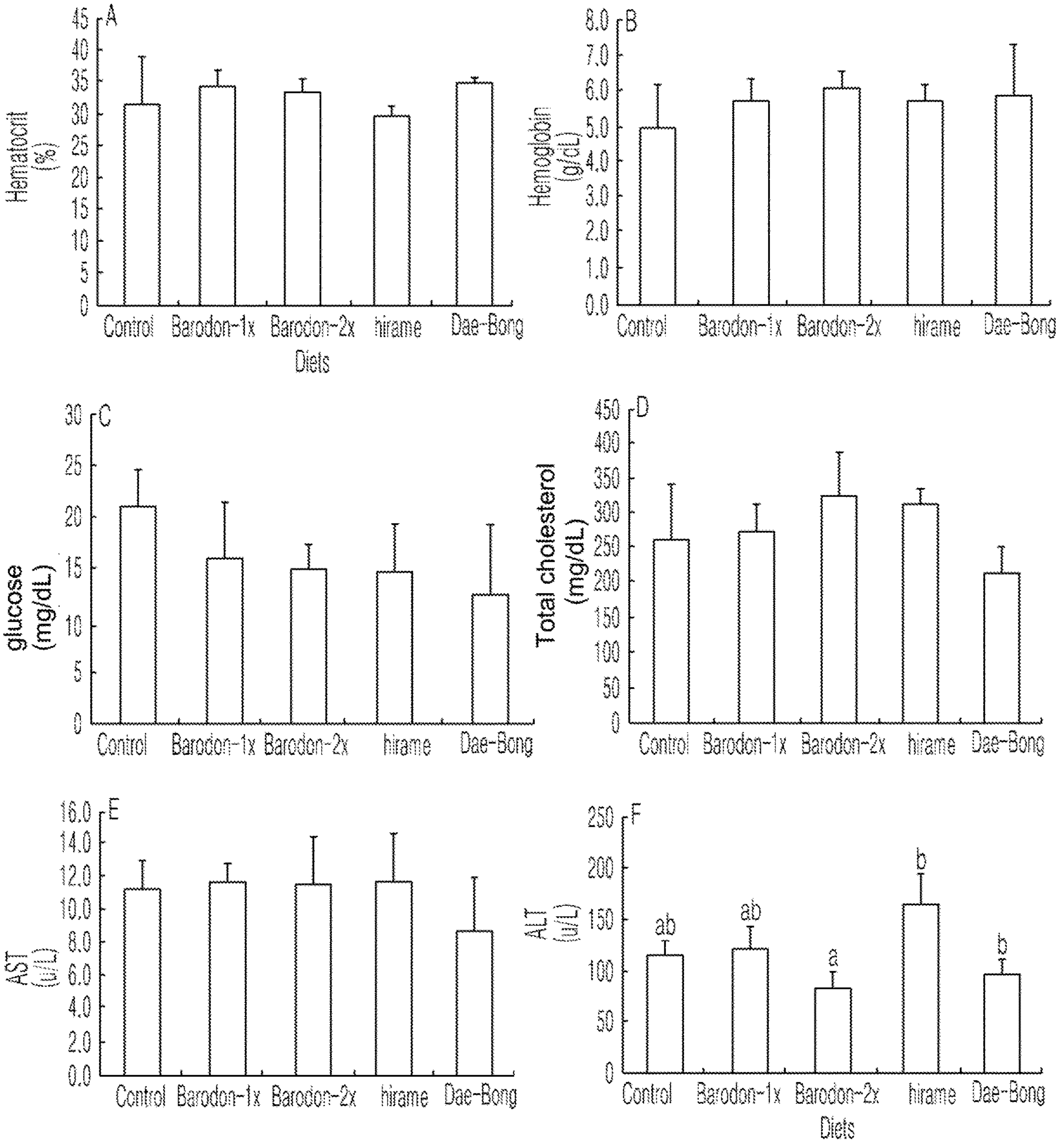
FIG. 19 shows graphs of blood indices in juvenile olive flounder fed for 15 weeks with 5 experimental diets ((A) hematocrit, (B) hemoglobin, (C) glucose, (D) total cholesterol, (E) ALT, (F) AST))

Results of the 15-week growth experiment are shown in Table 9 and FIG. 18. No significant differences in weight gain were observed among all the groups. However, the group fed with Hirame diet (H) tended to gain somewhat greater weights than the other groups, and BARODON-2× (0.02%) group increased in weight gain by 12%, compared to the control group. As for feed conversion rate, a significant increase was observed in all the groups except for the control group. The dietary supplementation of BARODON-1× (0.01%) and 2× (0.02%), and Hirame diet (H) significantly improved the specific growth rate, compared to the control. Groups fed with BARODON-supplemented diets significantly outlived the control group. Significant differences were neither found in protein efficiency ratio, nor in hematological analysis over the experimental range (Table 10 and FIG. 19).

Figure 20:
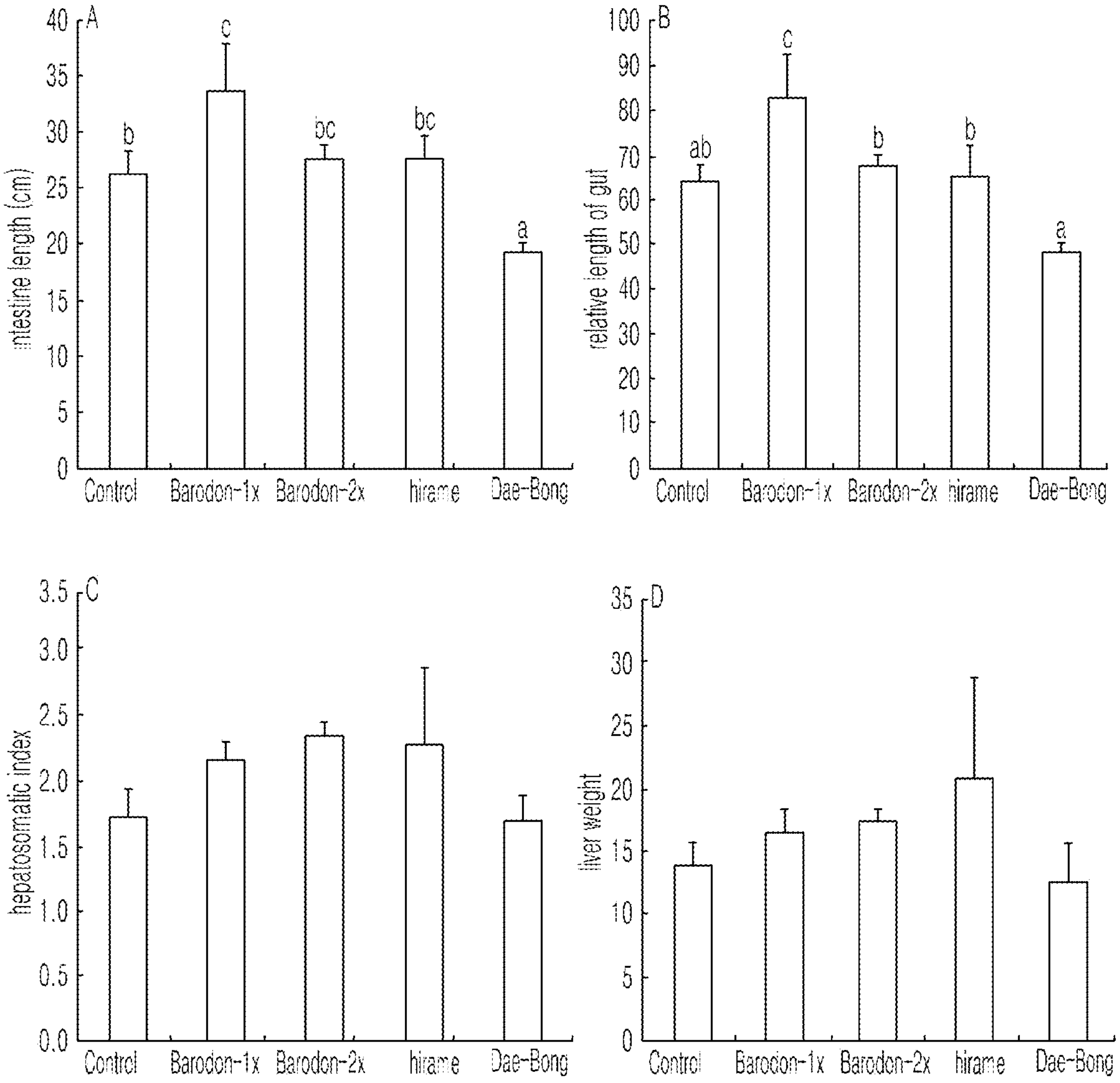
FIG. 20 shows graphs of morphological indices in juvenile olive flounder fed for 15 weeks with five experimental diets ((A) intestine length, (B) relative length of gut, (C) hepatosomatic index, (D) liver weight.
Figure 21:
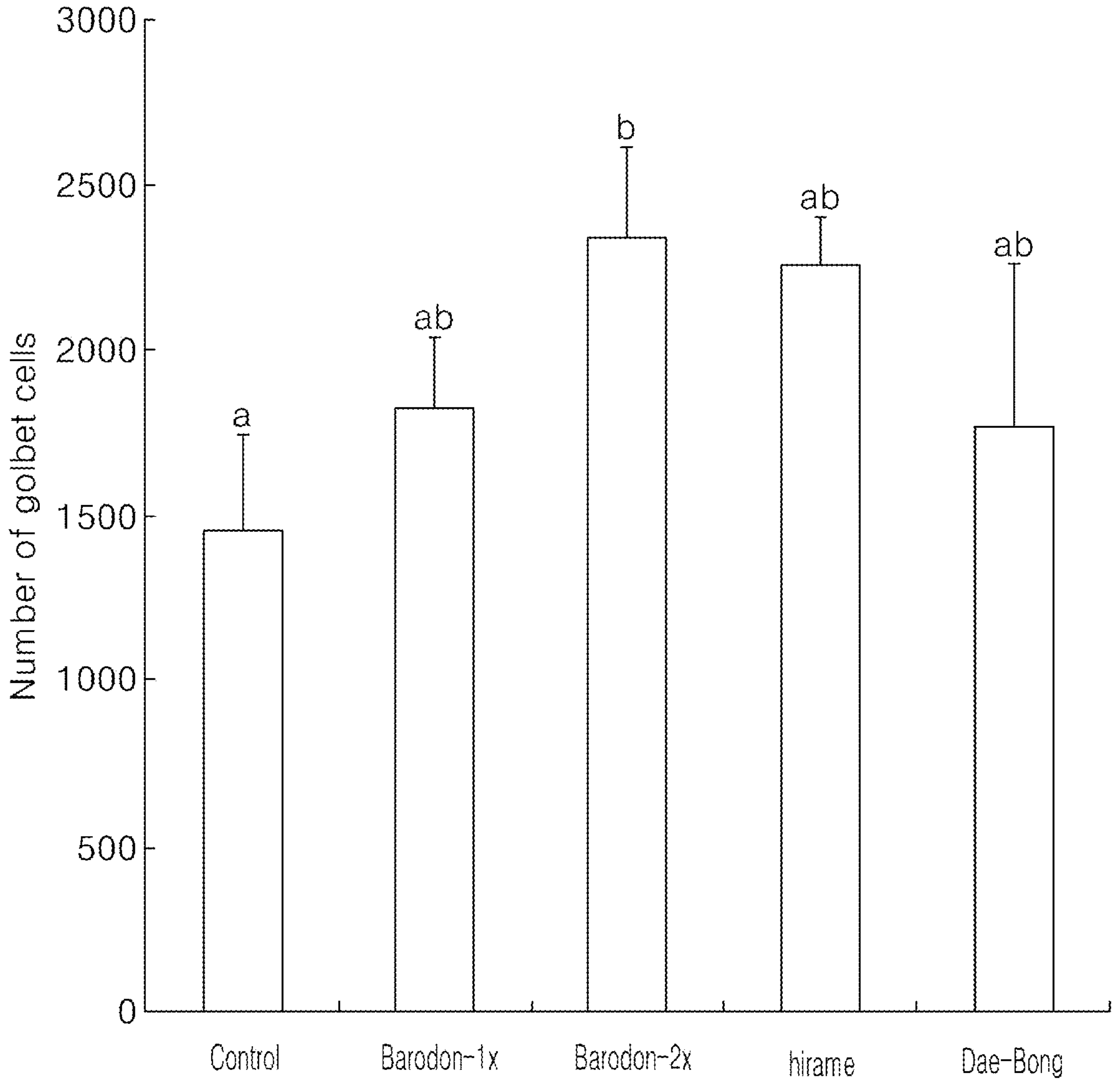
FIG. 21 is a graph of goblet cell counts in juvenile olive flounder fed for 15 weeks with five experimental diets.
Figure 22:
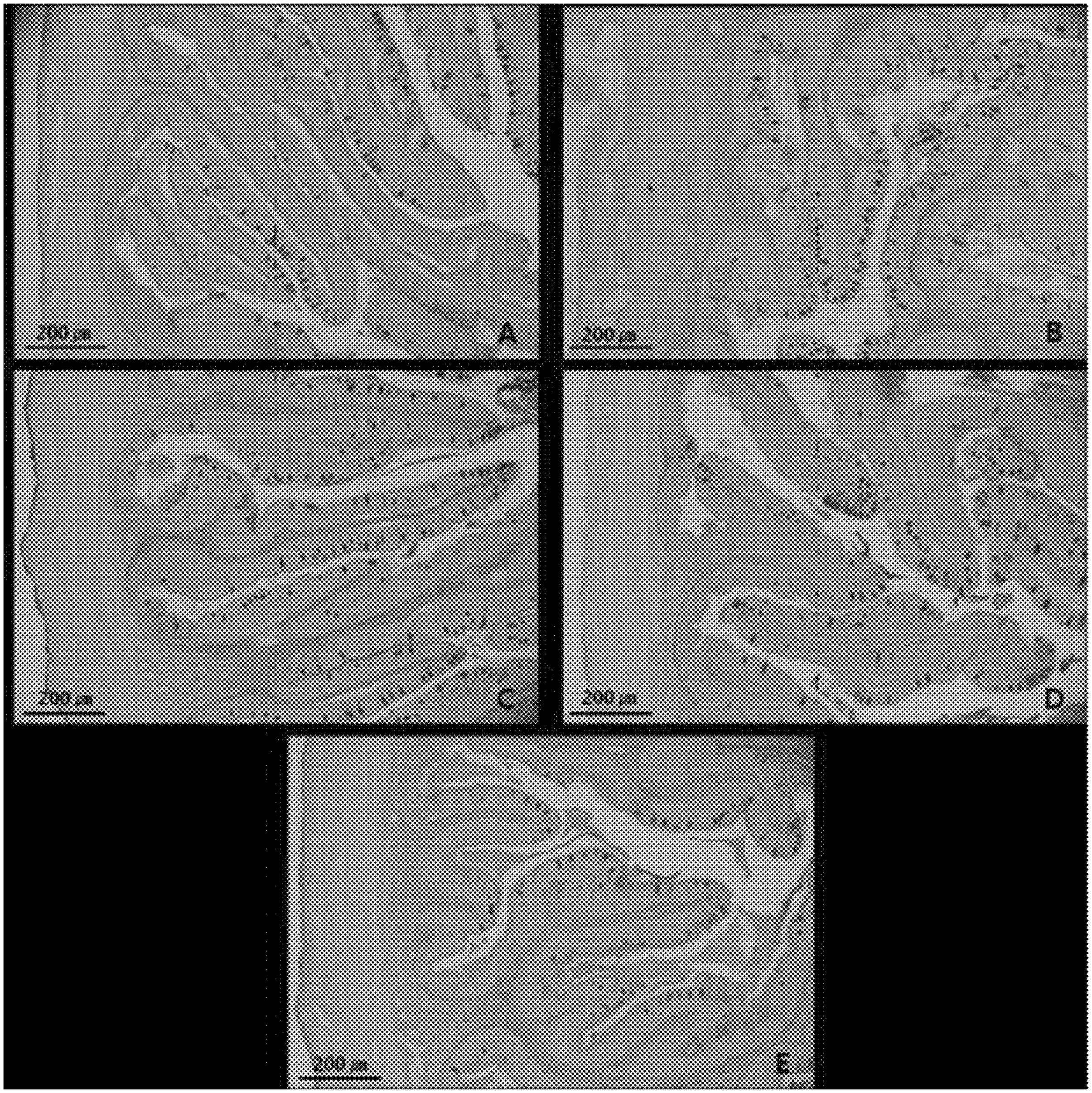
FIG. 22 shows photographs of intestinal goblet cells in olive flounder fed for 15 weeks with five extended granular diets ((A) control, (B) BARODON-1× (0.01%), (C) BARODON-2× (0.02%), (D) H Feed, and (E) D Feed)
Figure 23:
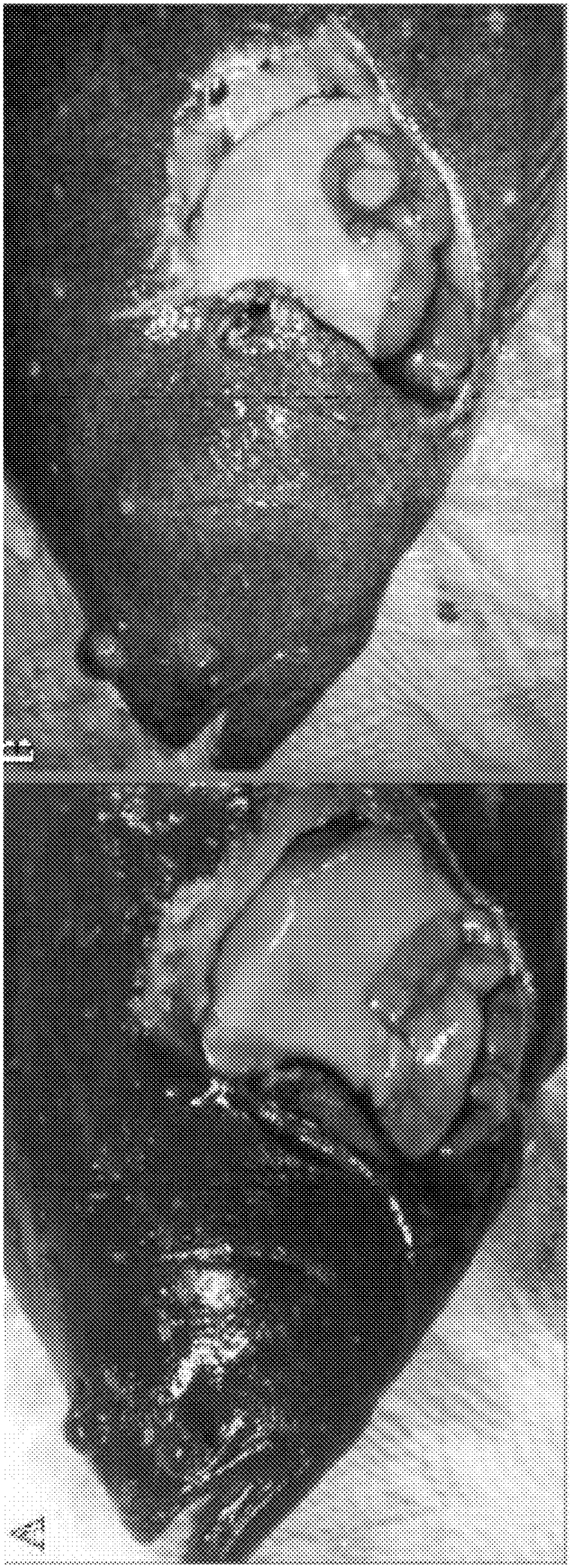
FIG. 23 shows photographs of liver morphologies in olive flounder fed for 15 weeks with five experimental diets ((A) Purina and H Feed commercial diets, (B) D Feed commercial diet)

Developmental traits of digestive organs were examined by analyzing hepatosomatic index, intestine length, relative length of gut, and goblet cells. Results showed that the BARODON-1× (0.01%) group had longer guts, compared to the control and the group of Dae Bong diet (D) (Table 11 and FIG. 20). Very interestingly, a greater number of goblet cells, which help digestive activity, was counted in the BARODON-2× (0.02%) than in the control, with significance (FIGS. 21 and 22). There was a great difference in liver color after the 15-week feeding. The liver of olive flounder appeared much redder fed when it was fed with BARODON-2× Purina EP diet or Hirame EP diet than with Dae Bong SLP. Hence, the use of BARODON-2× Purina EP may give a way to solve the liver color problem caused by EP diets (FIG. 23).

diet or Hirame EP diet. Hence, the dietary supplementation of BARODON may give a way to solve the liver color problem caused by EP diets.

TABLE 9

Growth performance of olive flounder (Initial BW: 145 g) fed the experimental diets for 15 weeks

| | FBW[1] (g) | WG[2] (%) | FCR[3] | SGR[4] (%) | PER[5] | Survival(%) |
|---|---|---|---|---|---|---|
| Control | 502 ± 43.6 | 246 ± 22.9 | 1.25 ± 0.04$^{a}$ | 0.53 ± 0.03$^{a}$ | 1.39 ± 0.26 | 70.7 ± 8.3$^{a}$ |
| BARODON-1X (BARODON 0.01%) | 541 ± 13.6 | 271 ± 13.3 | 1.01 ± 0.08$^{b}$ | 0.80 ± 0.07$^{b}$ | 1.62 ± 0.18 | 92.0 ± 4.0$^{b}$ |
| BARODON-2X (BARODON 0.02%) | 550 ± 4.6 | 275 ± 20.5 | 0.91 ± 0.05$^{b}$ | 0.92 ± 0.04$^{b}$ | 1.64 ± 0.12 | 96.0 ± 4.0$^{b}$ |
| H Feed | 582 ± 48.2 | 302 ± 44.3 | 0.91 ± 0.09$^{b}$ | 0.95 ± 0.06$^{b}$ | 1.69 ± 0.02 | 81.3 ± 6.1$^{ab}$ |
| D Feed | 558 ± 14.3 | 279 ± 20.2 | 1.00 ± 0.07$^{b}$ | 0.73 ± 0.17$^{ab}$ | 1.63 ± 0.02 | 77.3 ± 12.9$^{ab}$ |

Mean values of triplicate groups, values are presented as mean ± SD.
Values in the same column having different superscript letters are significantly different ($p < 0.05$).
[1]FBW: final body weight (g)
[2]Weight gain (%) = 100 × (final mean body weight − initial mean body weight)/initial mean body weight
[3]Feed conversion ratio = dry feed fed/wet weight gain
[4]specific growth rate (%) = [(loge final body weight − loge initial body weight)/days] × 100
[5]Protein efficiency ratio = wet weight gain/total protein given

TABLE 10

Blood parameters of olive flounder (initial BV: 145 g) fed the five experimental diets for 15 weeks

| | Hematocrit (%) | Hemoglobin (g/dL) | Total cholesterol (mg/dL) | Glucose (mg/dL) | AST (U/L) | ALT (U/L) |
|---|---|---|---|---|---|---|
| Control | 31.5 ± 7.6 | 5.00 ± 1.18 | 261 ± 81.0 | 21.0 ± 3.3 | 115 ± 13.8 | 11.2 ± 1.9 |
| BARODON-1X (BARODON0.01%) | 34.6 ± 2.3 | 5.74 ± 0.55 | 273 ± 41.3 | 15.8 ± 5.7 | 122 ± 22.1 | 11.7 ± 1.1 |
| BARODON-2X (BARODON0.02) | 33.6 ± 1.8 | 6.08 ± 0.38 | 325 ± 63.3 | 14.9 ± 2.3 | 81.9 ± 14.6 | 11.6 ± 2.7 |
| H Feed | 29.8 ± 1.5 | 5.75 ± 0.41 | 314 ± 22.3 | 14.7 ± 4.6 | 165 ± 29.1 | 11.7 ± 2.9 |
| D Feed | 35.3 ± 0.4 | 5.88 ± 1.39 | 215 ± 37.9 | 12.4 ± 6.7 | 96.7 ± 11.8 | 8.7 ± 3.1 |

Mean values of triplicate groups, values are presented as mean ± SD.
Values in the same column having different superscript letters are significantly different ($p < 0.05$).

TABLE 11

The morphological indices of olive flounder (initial BV: 145 g) fed the experimental diets for 15 weeks

| | Body Weight (g) | Body length (cm) | Liver Weight (g) | HS I[1] | Intestine length (cm) | RLG[2] | No. of Goblet cells |
|---|---|---|---|---|---|---|---|
| Control | 807 ± 107 | 41.4 ± 0.6 | 13.8 ± 1.9 | 1.72 ± 0.23 | 26.3 ± 1.9$^{b}$ | 63.4 ± 4.3$^{ab}$ | 1456 ± 28.7$^{a}$ |
| BARODON-1X (BARODON0.01%) | 764 ± 48 | 40.6 ± 0.7 | 16.5 ± 1.9 | 2.16 ± 0.15 | 33.7 ± 4.3$^{c}$ | 82.9 ± 9.3$^{c}$ | 1834 ± 203$^{ab}$ |
| BARODON-2X (BARODON0.02) | 739 ± 20 | 40.8 ± 0.8 | 17.4 ± 1.0 | 2.35 ± 0.08 | 25.7 ± 1.3$^{bc}$ | 67.3 ± 2.2$^{b}$ | 2342 ± 138$^{b}$ |
| H Feed | 890 ± 131 | 42.3 ± 1.4 | 20.7 ± 8.1 | 2.27 ± 0.61 | 27.5 ± 2.3$^{bc}$ | 65.1 ± 6.9$^{b}$ | 2264 ± 138$^{ab}$ |
| D Feed | 730 ± 107 | 39.9 ± 1.6 | 12.5 ± 3.2 | 1.69 ± 0.18 | 19.4 ± 0.6$^{a}$ | 48.5 ± 1.1$^{a}$ | 1775 ± 491$^{ab}$ |

Mean values of triplicate groups, values are presented as mean ± SD.
Values in the same column having different superscript letters are significantly different ($p < 0.05$).
[1]Hepatosomatic index = (liver weight/weight) × 100
[2]Relative length of gut = (intestine length/whole length) × 100

A greater number of goblet cells, which help digestion activity of olive flounder, was counted in the BARODON-2× (0.02%) group than in the control group, with significance (FIG. 22).

As can be seen in FIG. 23, a great difference in liver color was observed after the 15-week feeding. The liver of olive flounder appeared much redder fed when it was fed with BARODON-summplented EP diet than with Dae Bong SLP

Example 3-2

Assay for Disease Resistance of Juvenile Shrimp (*Litopenaeus vannamei*)

1. Experimental Diet

A total of 5 diets were prepared with the same crude protein content (39%) and energy (19.5 MJ/kg diet). Compositions and ingredients of the basal diet are summarized in Table 12. For experimental diets, the Barondon-free basal diet (control) was used, or added with BARODON Chois Gold (BARODON-0.5× (50 g), 1× (100 g), 2× (200 g), 3× (300 g), and 4× (400 g), based on a total of 1,000 kg of the diet. For the preparation of experimental diets, all diet sources were pulverized into powders that were significantly homogeneous in size, and accurately weighed before being mixed together. The mixture was blended with predetermined amounts of the BARODON solutions, together with distilled water in an amount of 30% by weight based on the total weight of the mixture. The resulting blends were extruded into pellets 3 mm in diameter, using a chopper machine (SMC-12, Kuposlice, Busan, Korea) (see FIG. 4). The pellets were dried for 1-2 days with electric fans, and sieved to a suitable size, followed by storage at −20° C. in a refrigerator until use.

[Composition of BARODON]

1. BARODON-0.5× (BARODON Chois Gold 50 g/0.005%)
2. BARODON-1× (BARODON Chois Gold 100 g/0.01%)
3. BARODON-2× (BARODON Chois Gold 200 g/0.02%)
4. BARODON-4× (BARODON Chois Gold 400 g/0.04%)

TABLE 12

Dietary formulation and proximate composition of the five experimental diets for *Litopenaeus vannamei* (% dry matter).

| | Experimental diets | | | | |
|---|---|---|---|---|---|
| Ingredients | Control | 0.5 X | 1 X | 2 X | 4 X |
| White fish meal | 35.0 | 35.0 | 35.0 | 35.0 | 35.0 |
| Soy bean meal | 22.0 | 22.0 | 22.0 | 22.0 | 22.0 |
| Squid liver meal | 4.0 | 4.0 | 4.0 | 4.0 | 4.0 |
| Wheat flour | 28.0 | 28.0 | 28.0 | 28.0 | 28.0 |
| Fish oil | 3.0 | 3.0 | 3.0 | 3.0 | 3.0 |
| Mineral mix[1] | 1.0 | 1.0 | 1.0 | 1.0 | 1.0 |
| Vitamin mix[2] | 1.0 | 1.0 | 1.0 | 1.0 | 1.0 |
| Choline chloride | 0.5 | 0.5 | 0.5 | 0.5 | 0.5 |
| Starch | 5.5 | 5.5 | 5.5 | 5.5 | 5.5 |
| BARODON[3] | 0 | 0.005 | 0.01 | 0.02 | 0.04 |
| Chemical composition (% dry mater) | | | | | |
| Dry matter | 86.4 | 86.9 | 86.5 | 86.0 | 86.1 |
| Protein | 39.0 | 39.0 | 38.7 | 38.4 | 38.7 |
| Lipid | 8.5 | 8.4 | 8.4 | 8.5 | 8.4 |
| Ash | 12.1 | 12.9 | 12.9 | 12.0 | 12.4 |
| Gross energy MJ/kg[4] | 19.6 | 19.4 | 19.4 | 19.6 | 19.5 |

TABLE 12-continued

[1]Mineral premix (g/kg mixture): L-ascorbic acid, 121.2; DL-α tocopheryl acetate. 18.8; thiamin hydrochloride, 2.7; riboflavin, 9.1; pyridoxine hydrochloride, 1.8; niacin, 36.4; Ca-$_D$-pantothenate, 12.7; myo-inositol, 181.8; $_D$-biotin, 0.27; folic acid, 0.68; p-aminobezoic acid, 18.2; menadione, 1.8; retinyl acetate, 0.73; cholecalficerol, 0.003; cyanocobalamin, 0.003

[2]Vitamin premix (g/kg mixture): $MgSO_4•7H_2O$, 80.0; $NaH_2PO_4•2H_2O$, 370.0; KCl, 130.0; Ferric citrate, 40.0; $ZnSO_4•7H_2O$, 20.0; Ca-lactate, 356.5; $CuCl_2$, 0.2; $AlCl_3•6H_2O$, 0.15; $Na_2Si_2O_3$, 0.01; $MnSO_4•H_2O$, 2.0; $CoCl_2•6H_2O$, 1.0

[3]BARODON was provided by BARODON -SF Corp, Ansung, Gyounggi, 456-880, Korea

[3]Gross energy of experimental diets was calculated according to gross energy values 5.64 kcal $g^{-1}$ crude protein, 4.11 kcal $g^{-1}$ carbohydrate, and 9.44 kcal $g^{-1}$ crude fat, respectively (NRC. 1993).

2. Productivity Analysis

After feeding for 6 weeks, the final weight of shrimp was measured to calculate weight gain, specific growth rate, feed conversion ratio, protein efficiency ratio, and survival, as in Table 13. The productivity of shrimps was significantly increased in terms of weight gain, specific growth rate and protein efficiency ratio when they were fed BARODON-supplemented diets than the control.

TABLE 13

Growth performance and feed utilization of *Litopenaeus vannamei* fed the five experimental diets for 6 weeks.

| | Control | 0.5X | 1X | 2X | 4X |
|---|---|---|---|---|---|
| IBW[1](g) | 3.99 ± 0.06 | 3.96 ± 0.04 | 3.99 ± 0.03 | 3.99 ± 0.04 | 3.99 ± 0.06 |
| FBW[2](g) | 9.43 ± 0.29[b] | 10.3 ± 0.14[ab] | 10.1 ± 0.38[ab] | 10.7 ± 0.75[a] | 10.6 ± 0.31[a] |
| WG[3](%) | 136 ± 7.6[b] | 159 ± 2.1[ab] | 153 ± 9.0[ab] | 168 ± 20.7[a] | 166 ± 7.5[a] |
| SGR[4] (%) | 2.21 ± 0.08[b] | 2.44 ± 0.02[a] | 2.38 ± 0.09[ab] | 2.52 ± 0.19[a] | 2.51 ± 0.07[a] |
| FCR[5] | 2.11 ± 0.15[a] | 1.92 ± 0.03[ab] | 1.96 ± 0.04[ab] | 1.81 ± 0.24[b] | 1.82 ± 0.10[b] |
| PER[6] | 1.22 ± 0.09[b] | 1.33 ± 0.02[ab] | 1.32 ± 0.03[ab] | 1.46 ± 0.21[a] | 1.42 ± 0.08[ab] |
| Feed intake[7] | 11.5 ± 0.51 | 12.1 ± 0.05 | 12.0 ± 0.58 | 12.0 ± 0.65 | 12.1 ± 0.65 |
| Survival (%) | 92.5 ± 6.9 | 94.2 ± 4.2 | 95.0 ± 4.3 | 94.2 ± 4.2 | 91.7 ± 4.3 |

Values are mean of quadruplicate groups and presented as mean ± S.D. Values with different superscripts in the same colume are significantly different ($P < 0.05$). The lack of superscript letter indicates no signficant differences among treatments:

[1]IBW: initial body weight (g)

[2]FBW: final body weight (g)

[3]Weight gain (%) = 100 × (final mean body weight − initial mean body weight)/initial mean body weight

[4]Specific growth ratio (% $day^{-1}$) = [(loge final body weight − loge initial body weight)/days] × 100

[5]Feed conversion ratio = dry feed fed (g)/wet weight gain (g)

[6]Protein efficiency ratio = wet weight gain/total protein given

[7]Feed intake = dry feed consumed (g)/fish

TABLE 14

Total haemocyte count and non-specific immune parameters of *Litopenaeus vannamei* fed the five experimental diets for 6 weeks.

| | Control | 0.5X | 1X | 2X | 4X |
|---|---|---|---|---|---|
| THC[1] | 259 ± 37.8[b] | 299 ± 47.4[ab] | 390 ± 91.1[a] | 410 ± 62.0[a] | 306 ± 45.9[ab] |
| Total protein[2] | 178 ± 17.6 | 189 ± 13.9 | 215 ± 8.4 | 208 ± 29.2 | 197 ± 32.7 |

TABLE 14-continued

Total haemocyte count and non-specific immune parameters of *Litopenaeus vannamei* fed the five experimental diets for 6 weeks.

| | Control | 0.5X | 1X | 2X | 4X |
|---|---|---|---|---|---|
| NBT[3] | 2.55 ± 0.10 | 2.95 ± 0.43 | 3.00 ± 0.28 | 2.85 ± 0.32 | 2.79 ± 0.24 |
| PO[4] | 0.15 ± 0.01$^b$ | 0.17 ± 0.02$^{ab}$ | 0.18 ± 0.03$^{ab}$ | 0.19 ± 0.02$^a$ | 0.17 ± 0.01$^{ab}$ |
| Lysozyme[5] | 3.16 ± 0.17$^b$ | 3.61 ± 0.12$^{ab}$ | 3.36 ± 0.40$^{ab}$ | 3.80 ± 0.30$^a$ | 3.35 ± 0.11$^{ab}$ |
| SOD[6] | 76.3 ± 8.7 | 79.8 ± 4.7 | 77.8 ± 5.4 | 79.6 ± 4.4 | 81.8 ± 4.3 |
| GPx[7] | 58.2 ± 9.9$^b$ | 69.6 ± 7.5$^{ab}$ | 75.1 ± 4.3$^a$ | 75.8 ± 5.9$^a$ | 72.1 ± 7.8$^{ab}$ |

Values are mean of quadruplicate groups and presented as mean ± S.D. Values with different superscripts in the same column are significantly different ($P < 0.05$). The lack of superscript

[1]Total haemocyte count ($10^5$ cells/ml)

[2]Total protein (mg/ml)

[3]Nitro blue tetrazolium activity (absorbance)

[4]Phenol oxidase activity (absorbance)

[5]Lysozyme activity (Units/ml)

[6]Superoxide dismutase (% inhibition)

[7]Glutathione peroxidase activity (nmol/min/ml)

3. Analysis for Immunity

The shrimps were analyzed for total blood cell count, total protein level, and immunity indices including NBT, PO, lysozyme, superoxide dismutase (SOD), and glutathione peroxidase (GPx) activities. As shown in Table 14, the number of total blood cells was significantly increased by the dietary supplementation of BARODON, and immunity was significantly improved in terms of PO and lysozyme activities in the 2× group and in terms of glutathione peroxidase (GPx) in both the 1× and the 2× group.

4. Result of Challenge Experiment

Figure 24:
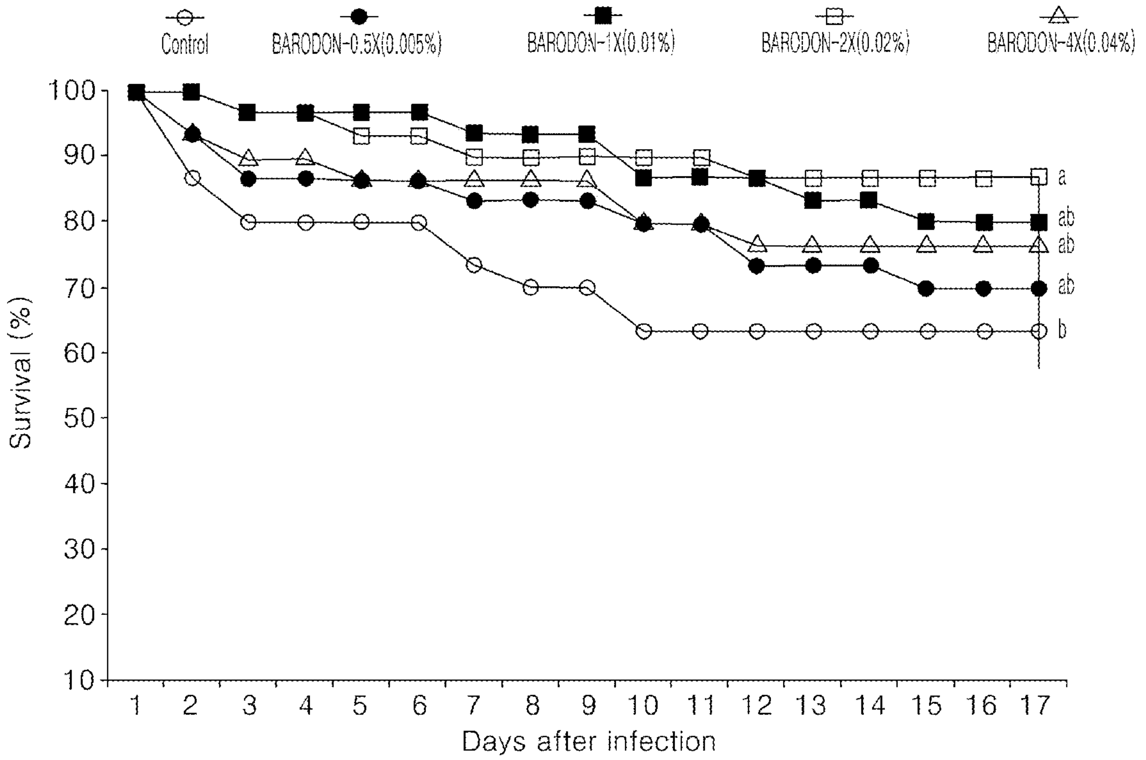
FIG. 24 is a graph of survival rates of shrimps fed with five experimental diets after challenge with *Vibrio harveyi;*

After completion of the 6-week growth experiment, examination was made of the effect of BARODON on the disease resistance of shrimps. To this end, the shrimps left after blood sampling were intraperitoneally injected with a suspension of *Vibrio harveyi*. The results of this challenge experiment are depicted in FIG. 24.

As can be seen, the control, not administered BARODON, died at a rate of 35%, which was higher than the mortality of the BARODON-administered groups. Particularly, the BARODON 2× (0.02%) group exhibited a mortality of 15% or less. The data, taken together, demonstrate that the dietary supplementation of BARODON improves shrimps in terms of resistance to diseases caused by *V. harveyi.*

Example 4

Assay for Immunostimulation in Swine

At the time of outbreak of foot-and-mouth in November, 2011 in Korea, the Clinical Pathology Lab. in College of Veterinary Medicine, Kangwon National University, the Microbiology Lab. in College of Veterinary Medicine, Seoul National University, and the Cargill Purina Research and Livestock Farm made research on the subject of "clinical application of the non-specific immunostimulator for prevention of FMD and enhancement of FMD vaccine efficacy" using the foot-and-mouth virus vaccine manufactured by the global pharmaceutical company (Merial, USA) under the bioindustrial technology development program supervised by the Korean Ministry of Agriculture, Food and Rural Affairs (Table 15).

For this, BARODON Chois Gold (Preparation Example 1) was added in an amount of 25 g (0.0025%), 50 g (0.005%), and 100 g (0.01%) to a 1 ton (1,000 kg) of a formulated feed mixture.

1. Material and Method

A. Test Design

For 9 weeks, an experiment was performed on 20 piglets 8 weeks old. Twenty 20 experimental pigs were divided into 4 groups including one control, and three test groups to which BARODON-supplemented diets were fed (Table 15). From 4 weeks after birth, BARODON-supplemented diets were fed. The experimental pigs were injected with FMD vaccine (Merial, USA) at 8 and 12 weeks after birth. From the start to the end of test, clinical symptoms and rectal temperatures were monitored every week. Growth rates were examined by measuring body weights at 8 and 16 weeks after birth. Blood samples were taken at post-birth 8, 10, 12, 13, 14, 15 and 16 weeks for antibody titer measurement and at post-birth 8, 10, 12, 14 and 16 weeks for flow cytometry.

TABLE 15

| Experimental groups | | | |
|---|---|---|---|
| Group | No. of pigs | Vaccine inoculation | Concentration of Barodon (%) |
| A | 5 | ○ | 0 |
| B | 5 | ○ | 0.0025 |
| C | 5 | ○ | 0.005 |
| D | 5 | ○ | 0.01 |

B. Antibody Titration

Serum was isolated by centrifugation, and inactivated at 56° C. for 30 min before use in examination. Antibody titers against FMD in the inactivated serum was analyzed by ELISA using an FMD antibody test ELISA kit (Prionics. USA) according to the instruction of manufacturer's. The serum was 1:10 diluted, and plated in an amount of 100 μl per well. After incubation for 30 min, the plates were washed three times with a washing solution. The swine IgG secondary antibody provided by the kit was added at a dose of 100 μl to each well, incubated for 30 min, and washed 6~7 times with a washing solution. Each well was visualized by incubation with 100 μl of TMB solution for 15 min in a dark chamber, followed by terminating the reaction with a stop solution. Optical density was measured at 650 nm, and calculated according to values for the positive control and the negative control. The wells with an S/P ratio of 40 or higher was determined as positive.

C. Flow Cytometry

After being separated from blood by centrifugation, a buffy coat layer was placed on a Ficoll layer (Sigma).

Following centrifugation at 1500 rpm for 20 min, white blood cells were taken from the interface between plasma and Ficoll, and washed with PBS. Viable cells were counted using a tryphan blue exclusion technique, and adjusted to a final density of $1\times10^7$ cells/ml. The analysis of subpopulations of leukocytes was performed using monoclonal antibodies specific for cell surface molecules.

2. Result

A. Clinical Symptom

No special clinical symptoms were observed in the test swine during the experiment period. In addition, none of side effects such as erythema, suppuration, hemorrhage, granuloma, and necrosis were found around the injection site.

Figure 25:
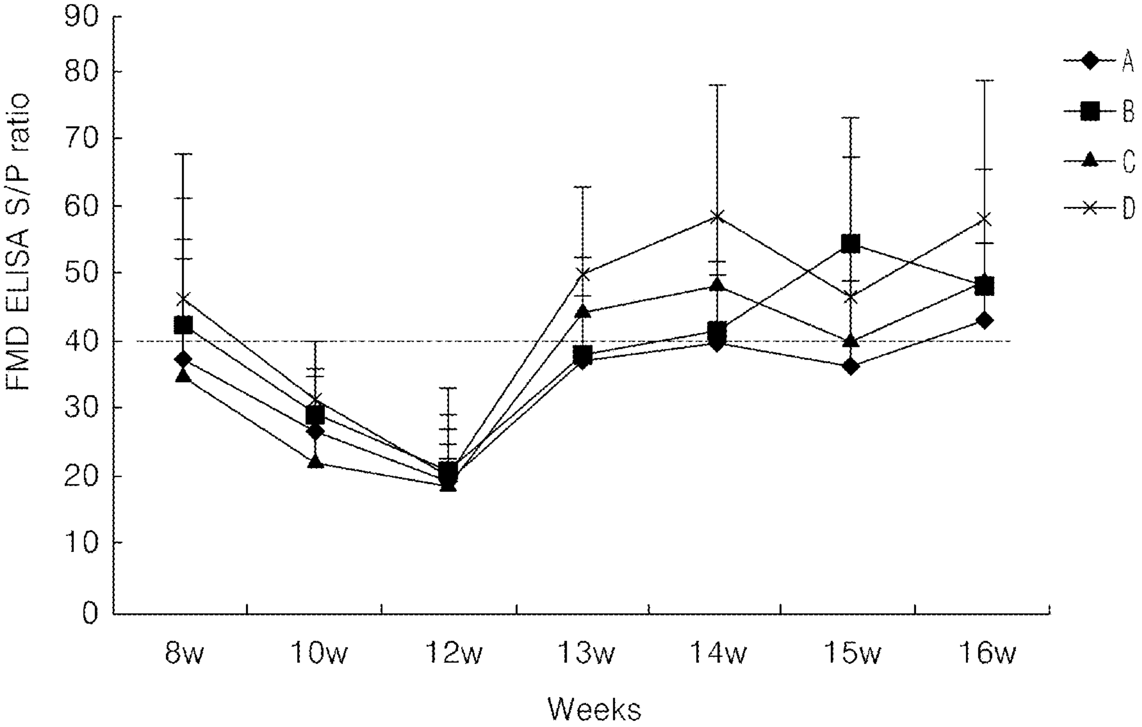
FIG. 25 is a graph of antibody titers in swine after injection with FMD vaccine.

B. The average antibody titer of the experiment swine that were 8 weeks old was measured to approximate have an antibody titer of approximate 40, a criterion for seroprevalence. Since the primary vaccination, the antibody titer continued to decrease. Secondary vaccination at 12 weeks after birth increased the antibody titer, and to more than 40, a criterion for seroprevalence, at 15-16 weeks after birth. The BARODON-fed groups exhibited more potent antibody reactions from post-birth week 12 at which secondary vaccination was performed, and maintained higher antibody titers than did the test group A until 16 weeks after birth. Prevalence at post-birth week 16 was measured to be 20% for test group A, 40% for test group B, and 60% for both test groups C and D, indicating that the dietary supplementation of BARODON increased prevalence (Table 16, FIG. 25).

TABLE 16

Antibody titer(S/P ratio) of pigs after FMD vaccine inoculation.

| Group | FMD-specific antibody titer according to vaccine inoculation | | | | | | |
|---|---|---|---|---|---|---|---|
| | 8 w | 10 w | 12 w | 13 w | 14 w | 15 w | 16 w |
| A | 37.0 ± 18.1 (1/5)* | 26.8 ± 8.2 | 19.0 ± 5.5 | 36.9 ± 6.8 | 39.9 ± 12.1 | 36.6 ± 12.5 | 43.4 ± 11.4 (1/5) |
| B | 42.8 ± 18.5 (1/5) | 29.0 ± 11.0 | 21.0 ± 8.0 | 37.5 ± 9.3 | 41.2 ± 8.7 | 54.2 ± 19.1 | 48.6 ± 16.7 (2/5) |
| C | 35.6 ± 16.7 (1/5) | 22.1 ± 7.4 | 18.7 ± 8.5 | 44.4 ± 8.1 | 48.5 ± 9.3 | 39.9 ± 14.8 | 49.3 ± 16.6 (3/5) |
| D | 46.2 ± 21.5 (2/5) | 31.0 ± 5.1 | 19.0 ± 14.2 | 49.9 ± 12.9 | 58.5 ± 19.7 | 46.5 ± 20.9 | 58.3 ± 20.5 (3/5) |

No. of seropositive pigs/No. of pigs inspected

C. Assay for Leukocyte Subpopulation by Flow Cytometry

Figure 26:
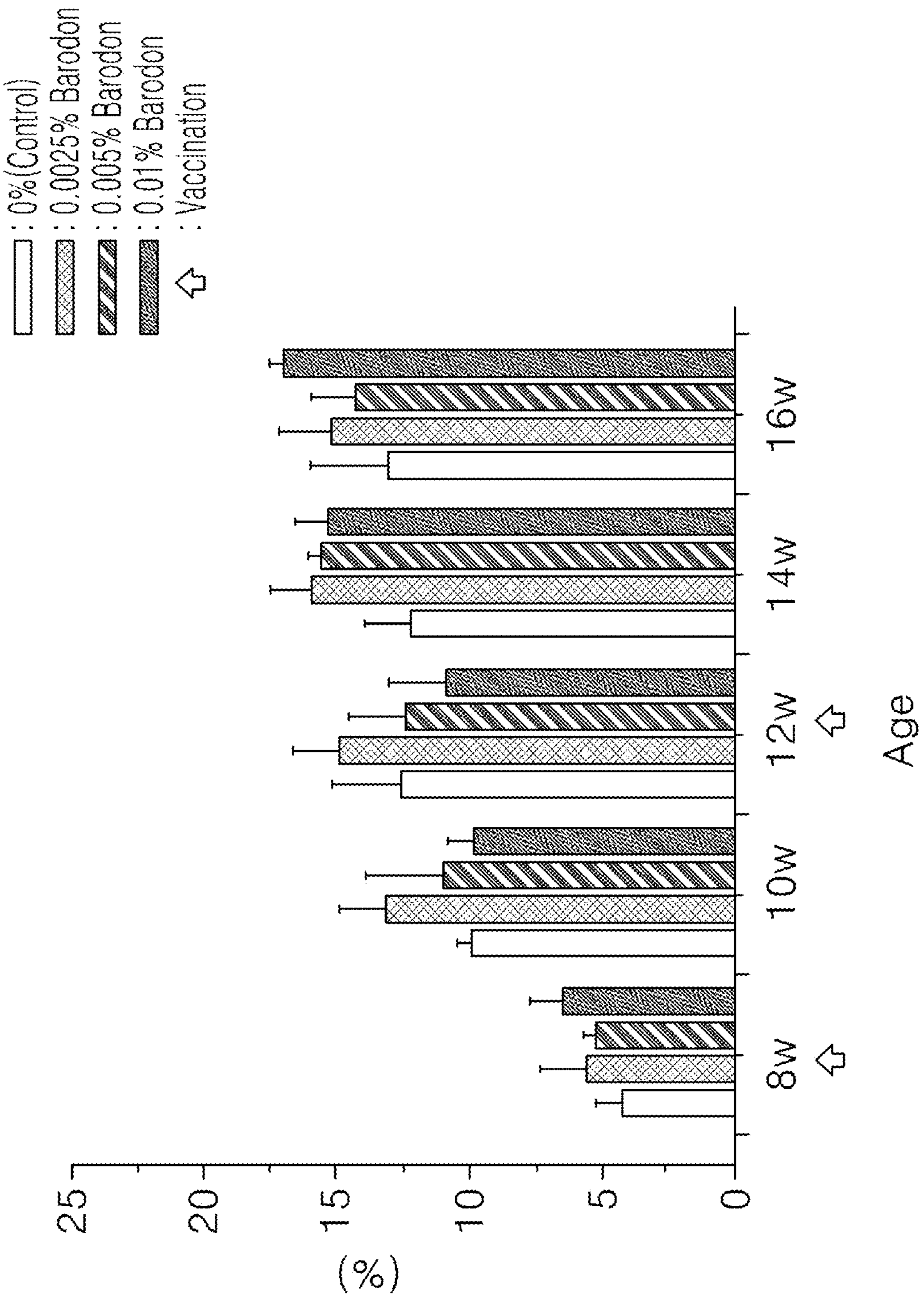
FIG. 26 is a cytotoxic T lymphocyte (CD3+CD4−CD8+) graph.

A gradual increase of leukocyte count was observed in swine from 8 to 12 weeks after birth. Since the secondary vaccination, all of the BARODON-fed groups were found to have higher populations of cytotoxic T lymphocytes, compared to the control (FIG. 26), but without significance.

Figure 27:
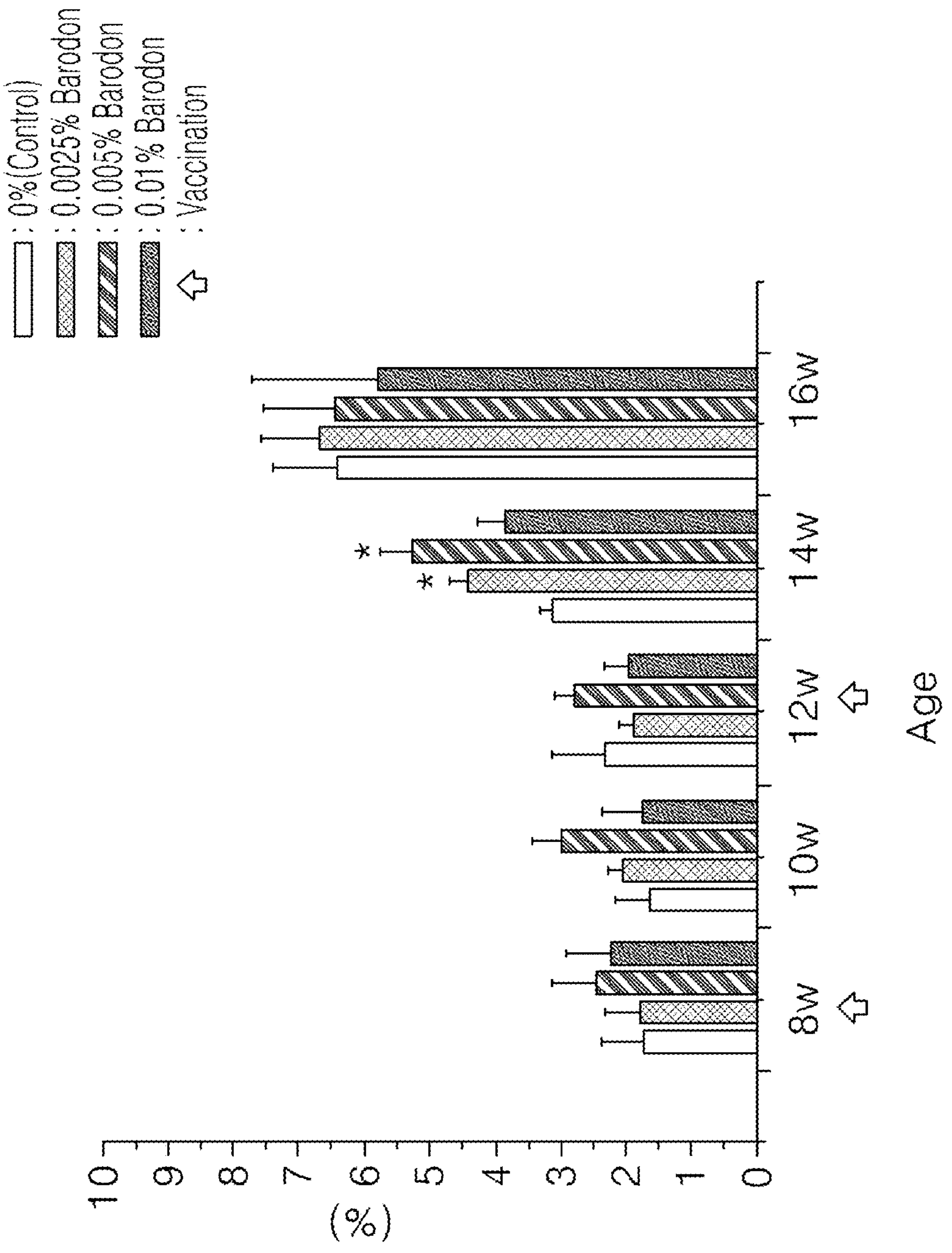
FIG. 27 is a memory T helper cell (CD3+CD4+CD8+) graph.

Two weeks after the secondary vaccination, a higher population of memory T helper cells was detected in the BARODON 0.0025%- and 0.005%-fed groups of 14-week-old swine than the control, with significance (FIG. 27).

Figure 28:
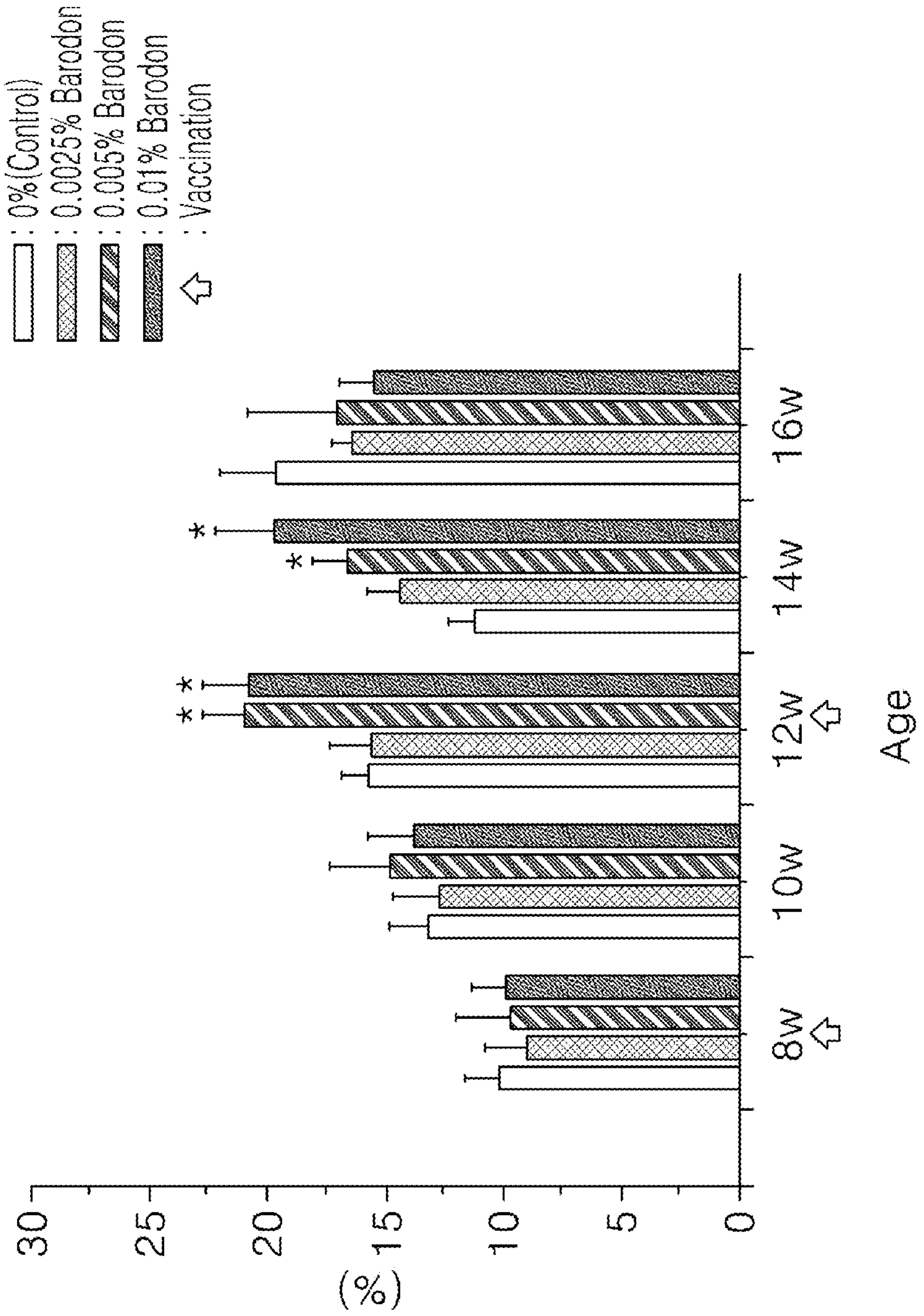
FIG. 28 is a naive T helper cell (CD3+CD4+CD8−) graph.

BARODON 0.005%- and 0.01%-fed groups exhibited a higher population of naive T helper cells than did the control at 12 and 14 weeks after birth, which corresponded to 4 weeks after the primary vaccination and 2 weeks after the secondary vaccination, respectively (FIG. 28).

Figure 29:
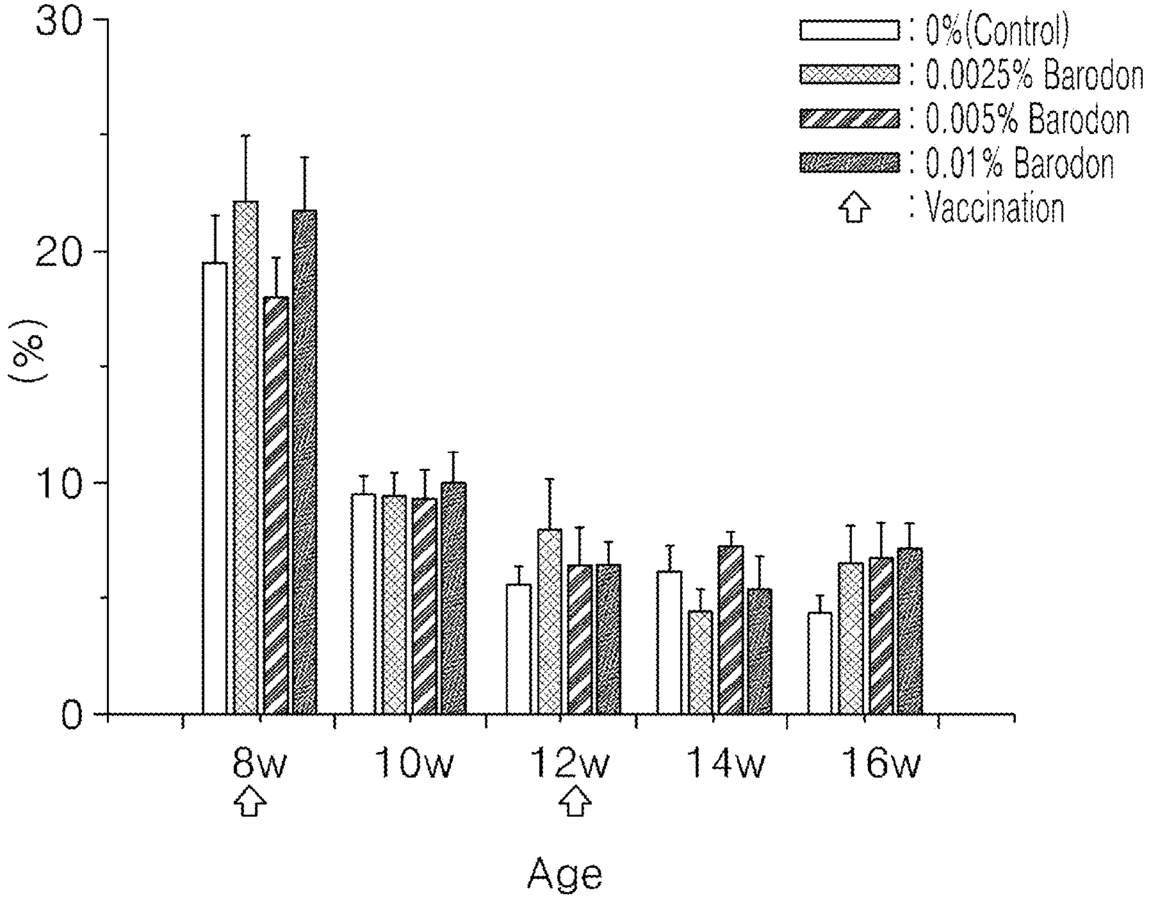
FIG. 29 is a B cell (CD3−CD21+) graph.

In all of the groups, a population of B cells was gradually decreased since the vaccination, which was not observed in a PRRS vaccination test, indicating that the vaccine itself did not bring about an increase in B cell population (FIG. 29).

Figure 30:
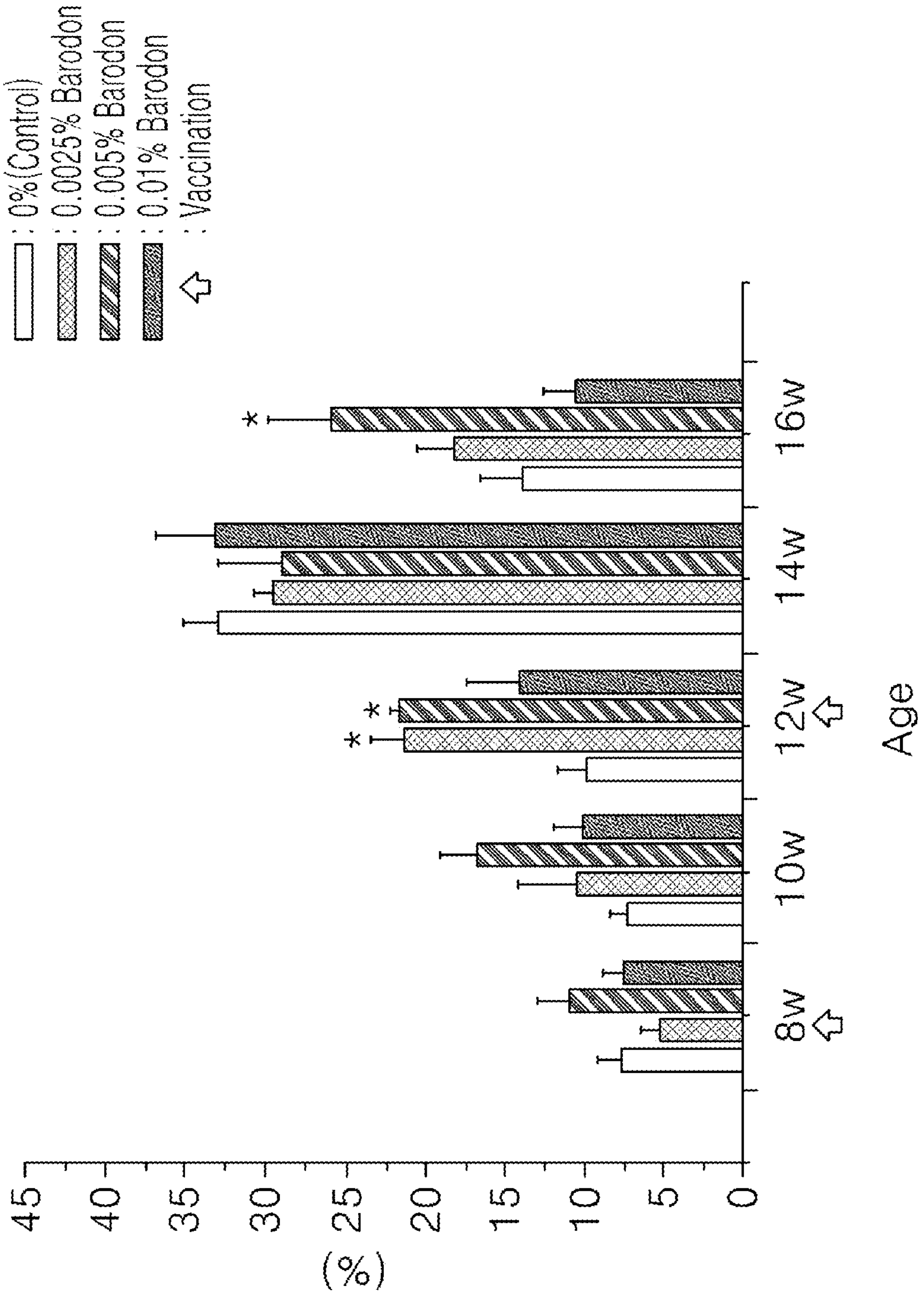
FIG. 30 is a γδ T lymphocyte (CD3+γδ+CD8−) graph.

As for γδ T lymphocyte, their population was observed to be a significantly high level in BARODON 0.0025%- and 0.0050-fed groups of the swine at the age of 12 weeks, which corresponded to 4 weeks after the primary vaccination, compared to the control. The population was elevated in all of the groups at 2 weeks after the secondary vaccination. A significantly elevated level of γδ T lymphocytes (CD3+γδ+CD8−) was maintained in the BARODON 0.005%-fed group of the swine at the age of 16 weeks, which corresponded to 4 weeks after the secondary vaccination (FIG. 30).

Figure 31:
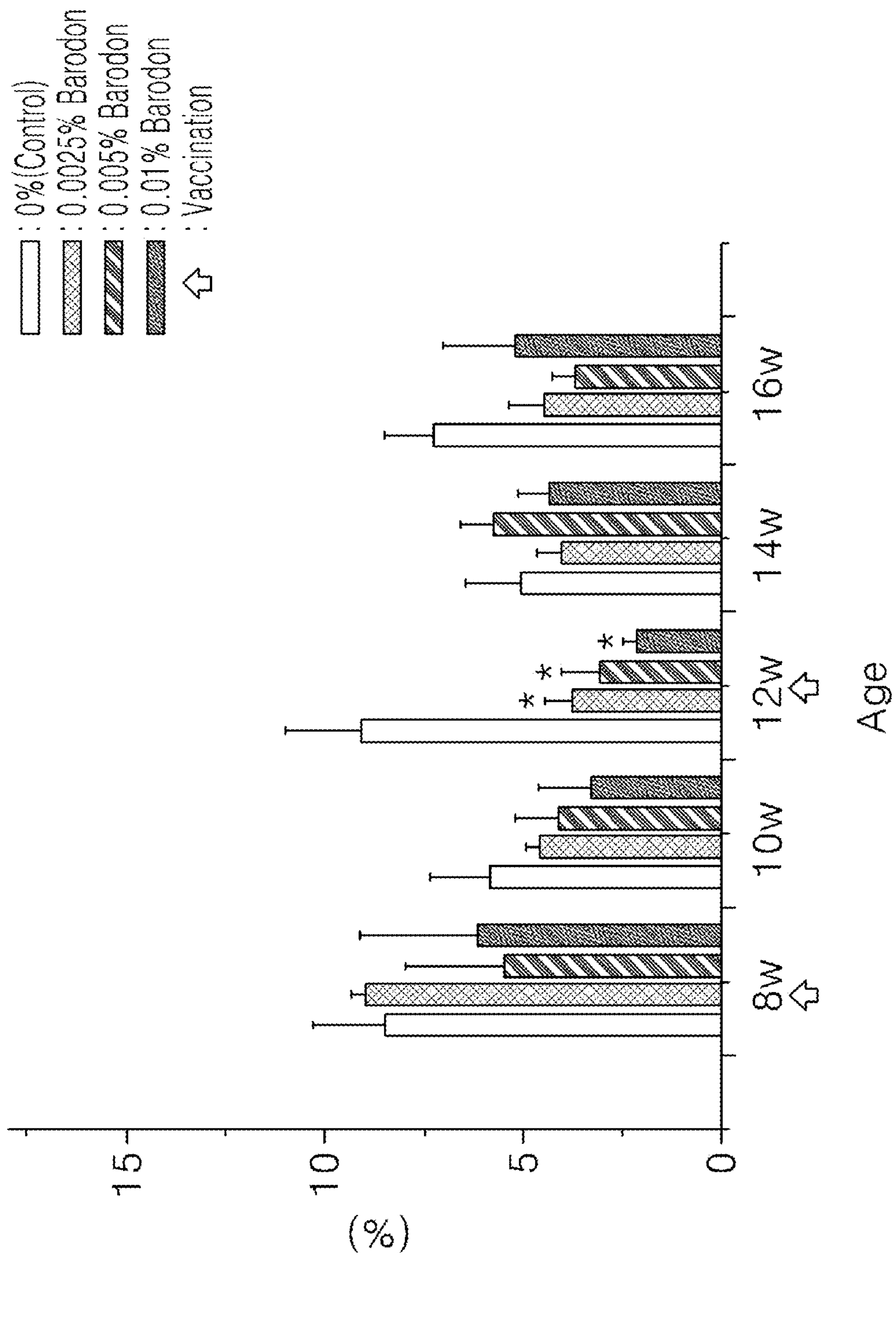
FIG. 31 is a NK cell (CD3−CD4−CD8+) graph.

At the age of 12 weeks, which corresponded to 4 weeks of the primary vaccination, the BARODON-fed groups were significantly low in NK cell population, compared to the control (FIG. 31).

Figure 32:
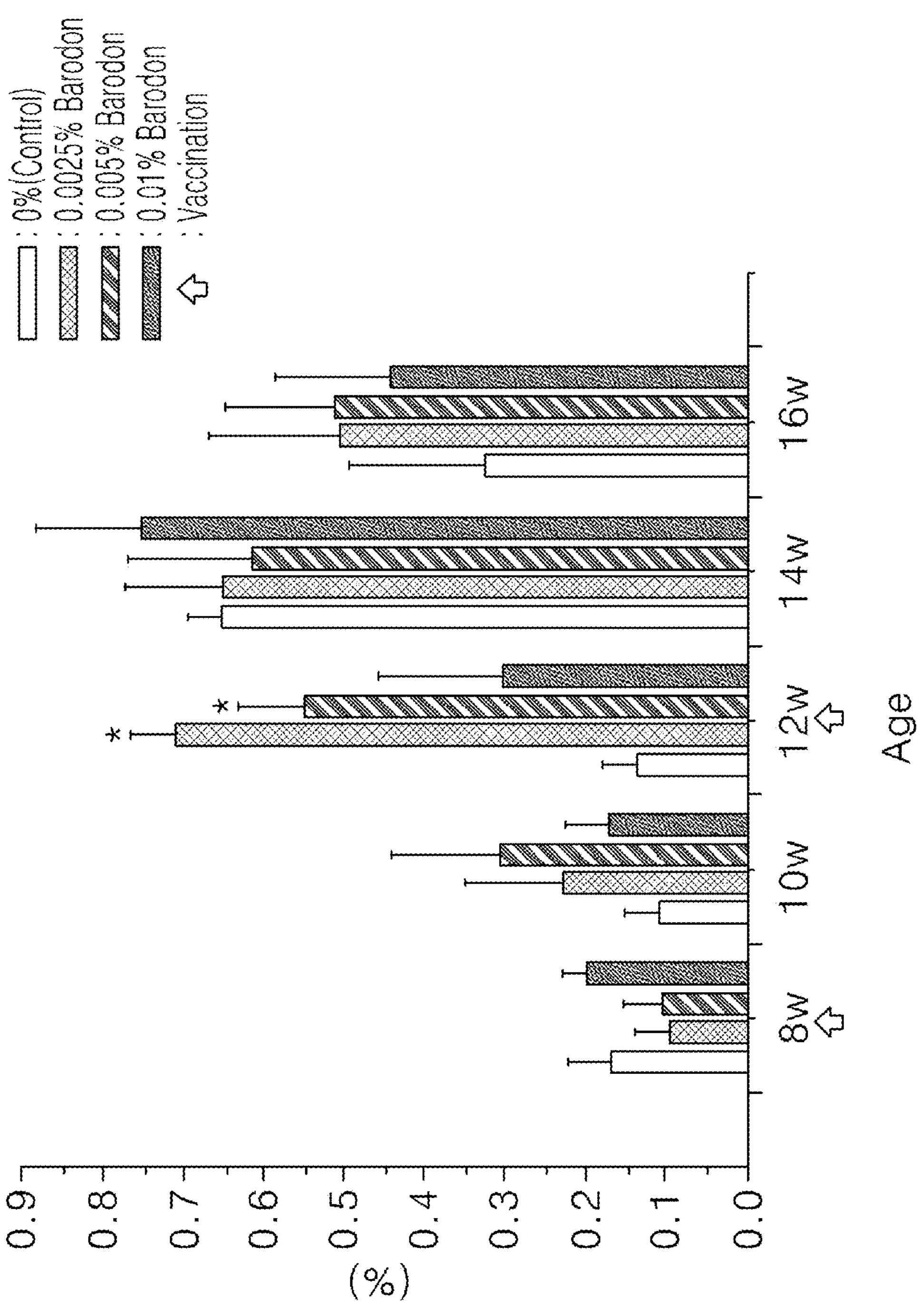
FIG. 32 is a CD8+ γδ T lymphocyte (CD3+γδ+CD8+) graph.

At the age of 12 weeks, which corresponded to 4 weeks of the primary vaccination, BARODON 0.0025%- and 0.005%-fed groups were significantly in CD8+ γδ T lymphocyte (CD3+γδ+CD8+) population, compared to the control. The population was elevated in all of the groups at the age of 14 weeks, which corresponded to 2 weeks after the secondary vaccination. A relatively high level of CD8+ γδ T lymphocytes (CD3+γδ+CD8−) was maintained in the BARODON-fed groups of the swine at the age of 16 weeks, which corresponded to 4 weeks after the secondary vaccination (FIG. 32), but without significance (FIG. 32).

Example 5

Assay for Immunostimulatory Effect in Cattle (Holstein)

BARODON Chois Gold, prepared in Preparation Example 1, was assayed for immunostimulation in cattle (Holstein).

A. Test Design

Twenty Holstein calves, weighing 77.41±14.41 kg, at the age of 3 months were used as test animals.

B. Test Period and Spot

Tests were performed in a research farm of Cargill Agri Purina, Inc., located at Bakchon-dong, Kyeyang-gu, Inchon city, Korea, for 98 days inclusive of the pre-raising period of 14 days, from Jun. 19, 2012 to Sep. 25, 2012.

C. Test Design and Method

The 20 Holstein calves were randomly divided into 4 groups of 5. Among 5 calves of each group, three were shunt up in a pen while the other two calves were confined to a different pen. As shown in Table 17, weights at the start and end of the test, and diet uptake were measured for control (BARODON 0%), test group 1 (BARODON 0.0025%), test group 2 (BARODON 0.005%), and test group 3 (BARODON 0.01%) to examine productivity.

D. Antibody Titration

Figure 33:
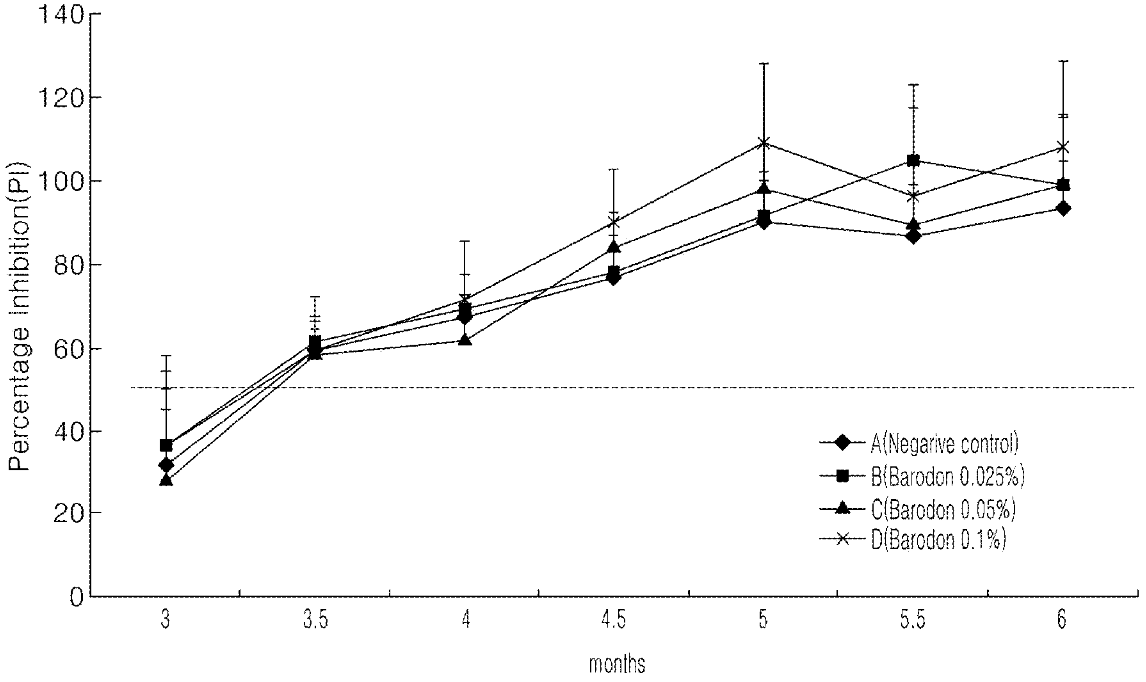
FIG. 33 is a graph of antibody titers (S/P ratio) in Holstein cattle.

Before vaccination, the calves at the age of 3 months maintained an antibody titer of less than 50, a criterion for seroprevalence. Since primary vaccination, the antibody titer gradually increased and finally over 50. After secondary vaccination at the age of 4 months, the increase of antibody titer was also continued. The primary vaccination increased antibody titers at similar rates over the groups whereas a rapid increase of antibody titer was observed to the age of five months in test group D (Table 17, FIG. 33).

TABLE 17

Antibody titer(S/P ratio) of Holstein

| Group | FMD-specific antibody titer | | | | | | |
|---|---|---|---|---|---|---|---|
| | 3 mon | 3.5 mon | 4 mon | 4.5 mon | 5 mon | 5.5 mon | 6 mon |
| A(0%) | 31.6 ± 18.1 | 59.0 ± 5.2 | 66.8 ± 5.5 | 76.9 ± 6.8 | 89.9 ± 12.1 | 86.6 ± 12.5 | 93.4 ± 11.4 |
| B(0.0025%) | 35.8 ± 18.5 | 61.0 ± 11.0 | 69.0 ± 8.0 | 77.5 ± 9.3 | 91.2 ± 8.7 | 104.2 ± 19.1 | 98.6 ± 16.7 |
| C(0.005%) | 28.3 ± 16.7 | 58.7 ± 7.4 | 62.1 ± 8.5 | 84.4 ± 8.1 | 98.5 ± 9.3 | 89.9 ± 14.8 | 99.3 ± 16.6 |
| D(0.01%) | 36.2 ± 21.5 | 59.0 ± 5.1 | 71.0 ± 14.2 | 89.9 ± 12.9 | 108.5 ± 19.7 | 96.5 ± 20.9 | 108.3 ± 20.5 |

E. Assay for Leukocyte Subpopulation by Flow Cytometry

Figure 34:
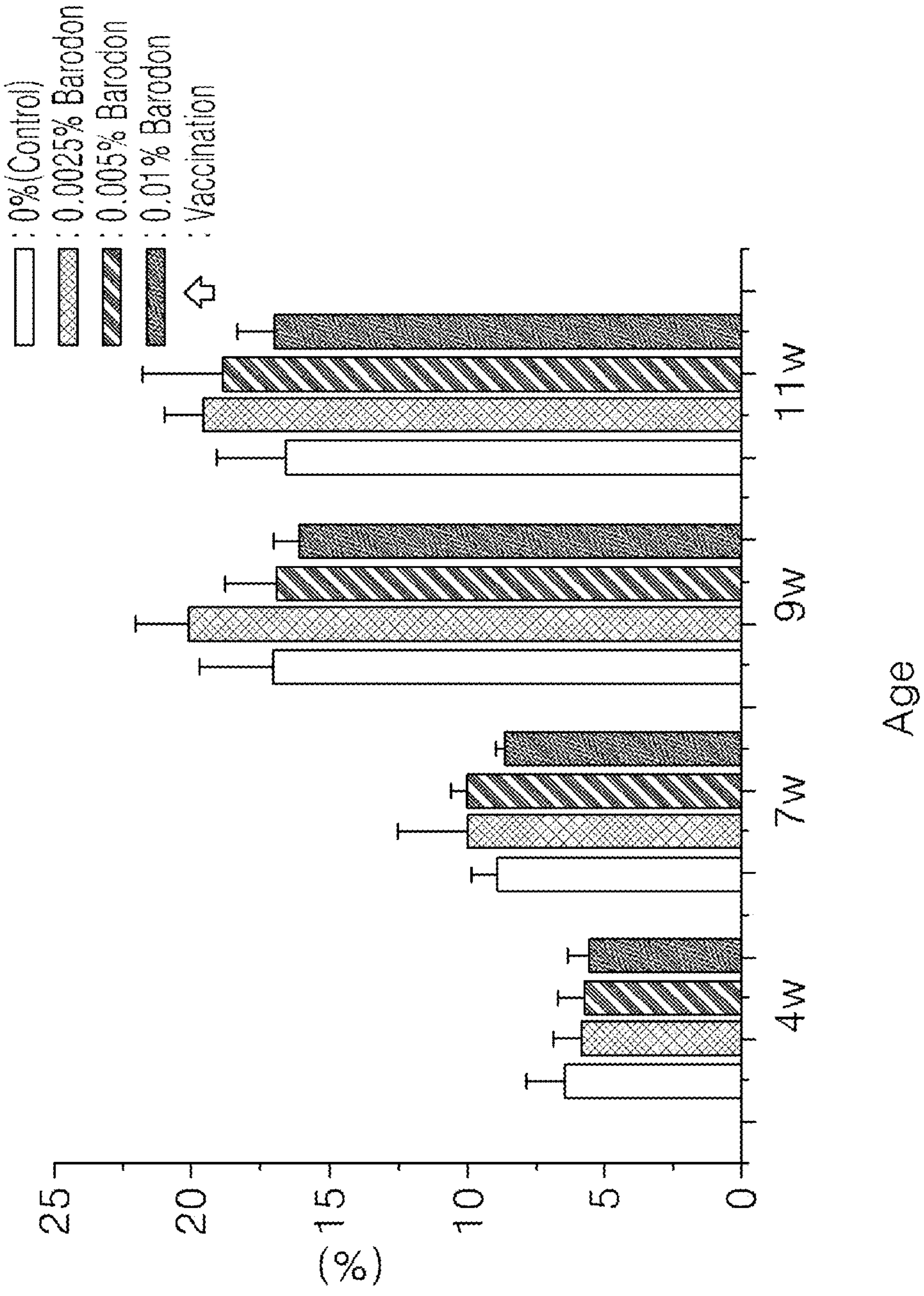
FIG. 34 is a cytotoxic T lymphocyte (CD3+CD4−CD8+) graph.

At an age of 7 weeks, which corresponded to 3 weeks after vaccination, a significantly higher population of memory T cells was detected in all of the BARODON-fed groups than the control group, indicating that the feeding of BARODON-containing diet contributed to the amplification of memory T cells after vaccination (FIG. 34).

Figure 35:
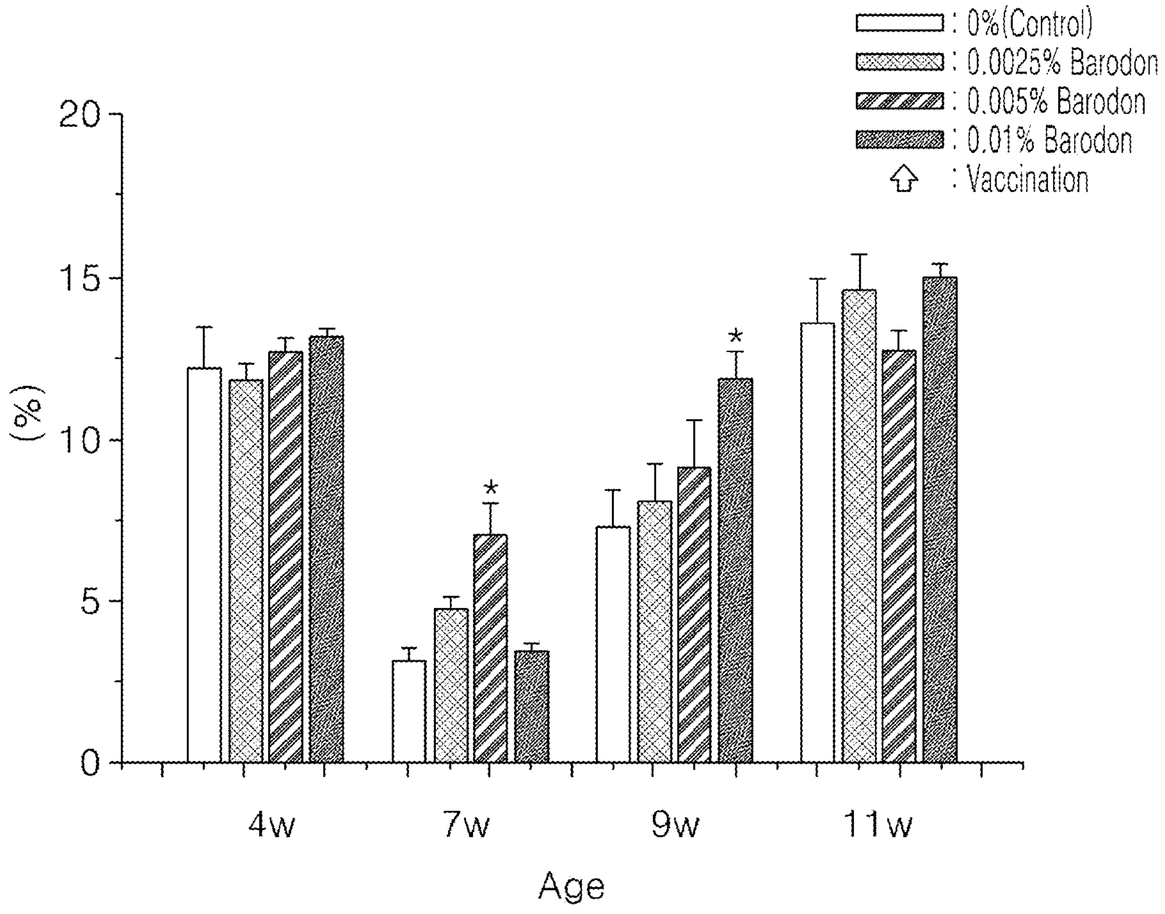
FIG. 35 is a naive T helper cell (CD3+CD4+CD8−) graph.

A population of memory T cells was observed to gradually decrease in all of the groups at the age of from 4 weeks to 7 weeks, but to increase at the age of 10 weeks. A significant high population of naïve T helper cells were found in BARODON 0.005%- and 0.01%-fed groups at the age of 7 weeks and 9 weeks, respectively (FIG. 35).

Figure 36:
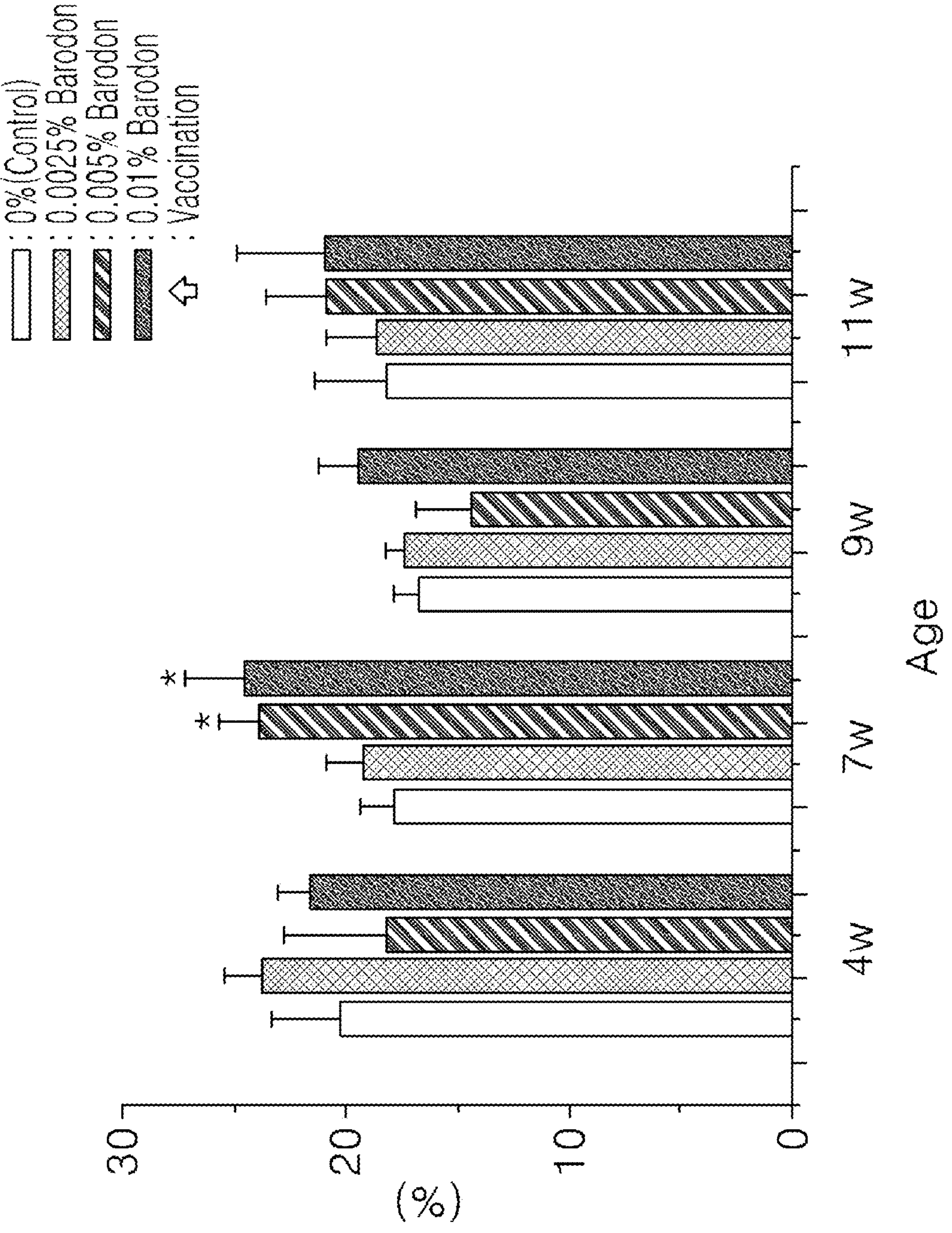
FIG. 36 is a B cell (CD3−CD21+) graph.

In contrast to the challenge test that was not vaccinated, all of the group that were vaccinated at the age of 4 weeks underwent a relatively small decrease of B cell populations when they grew to 9 weeks and 11 weeks. A significantly high population of B cells was observed in BARODON 0.005%- and 0.01%-fed groups at the age of 7 weeks (FIG. 36).

Figure 37:
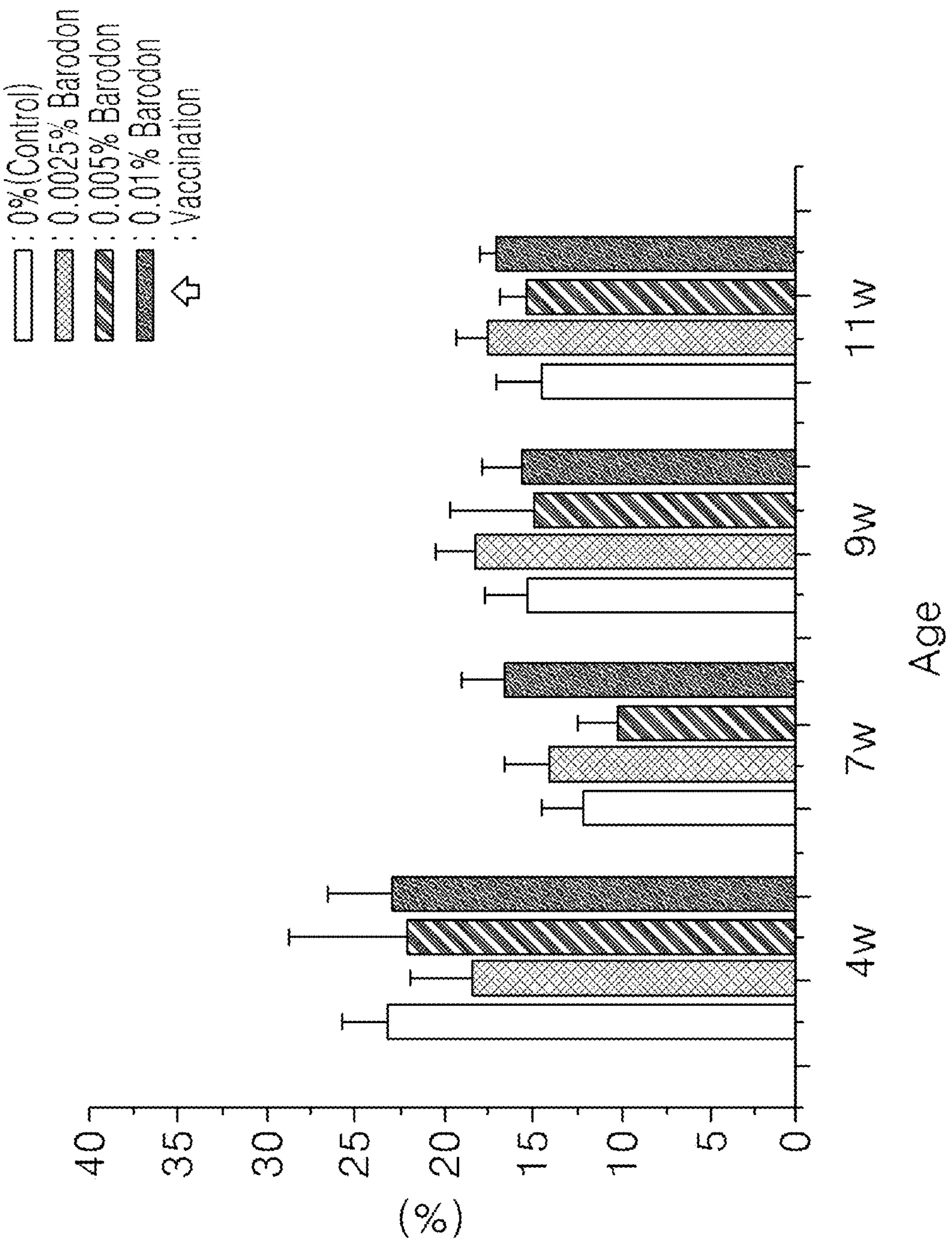
FIG. 37 is a γ δ T lymphocyte (CD3+γδ+CD8−) graph.

No significant difference was observed in γδ T lymphocyte population between BARODON-fed groups and the control over the test duration (FIG. 37).

Figure 38:
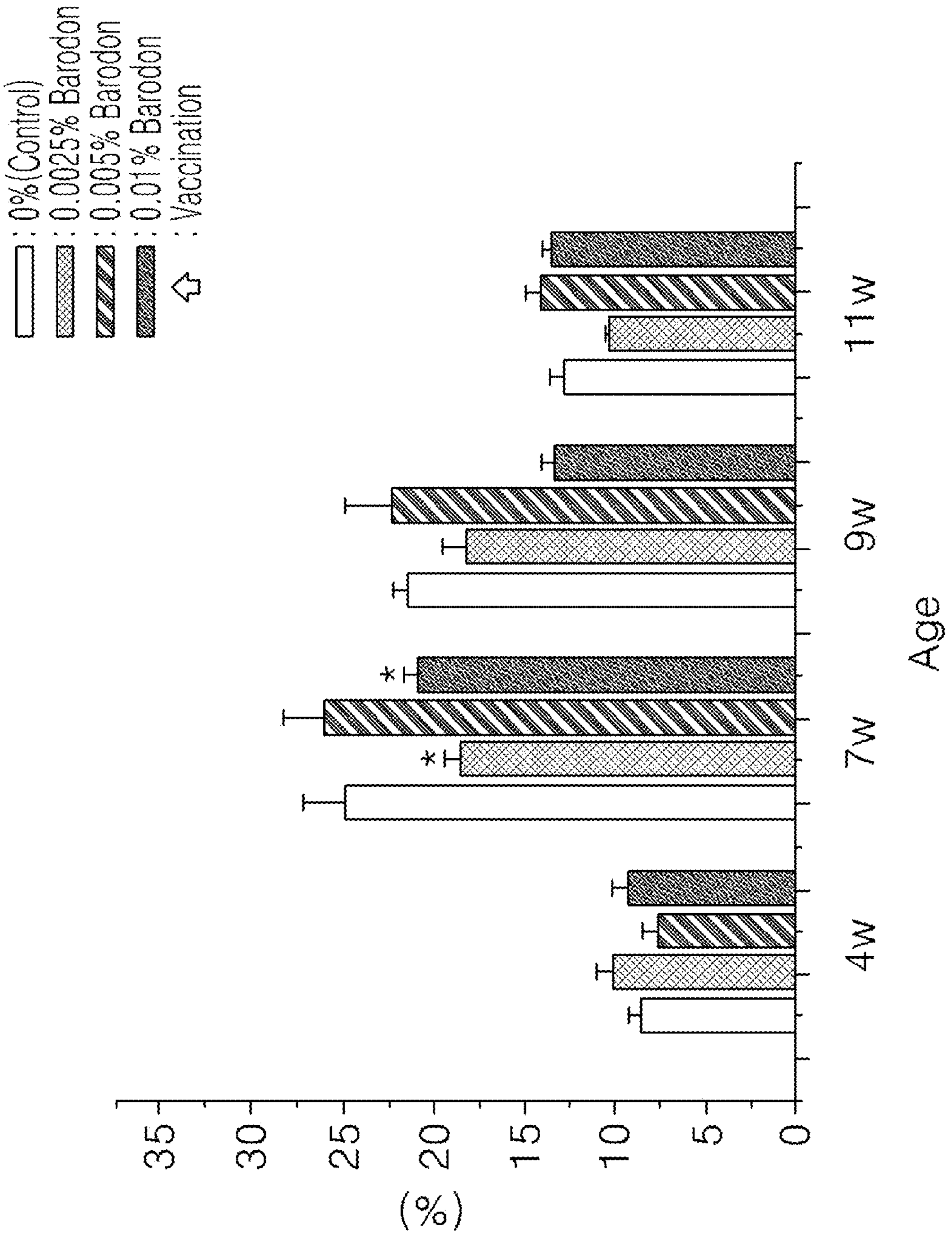
FIG. 38 is a NK cell (CD3−CD4−CD8+) graph.

At the age of 7 weeks, BARODON 0.0025%- and 0.01%-fed groups were considerably lower in NK cell population than were the other groups. This tendency was continuously observed in the pigs with ages of 9 weeks to 11 weeks, but with no significance (FIG. 38)

Example 6

The nonspecific immunostimulant complex mineral solution ("BARODON mineral solution"), prepared in Preparation Example 3, was assayed for sterile effect in the Korean Chemical Test Institute, located at Aegibong-ro 196, Wolgot-myon, Kimpo city, Korea.

1. Test Method

Test bacteria were cultured in broth, and diluted to a density of 1~9×$10^5$ CFU/ml before use in testing.

The test bacterial dilution was added to 20 mL of the test solution, and incubated at room temperature (5 min±10 sec), followed by counting viable cells to calculate % cell-reduction-by-sterilization against the initial cell count that was measured in saline.

In the initial dilution stage for all experiments, the test bacteria were allowed to undergo a neutralizing process in D/E Neutralizing Broth (DIFCO) before use in testing. When the bacteria did not proliferate in the medium, the cell count was multiplied with the dilution factor used in the neutralization stage and expressed as "less than 10 (<10)". Cell counting in all stages was conducted using TSA (see item 2.2). Viable cells were calculated according to Formula 1 of item 3.2 while % reduction was determined according to Formula 2.

2. Result Calculation

Viable cell count: N=C×D (Formula 1)

N: No. of viable cells

C: No. of colonies (average value of colonies on two plates)

D: Dilution factor (in dilution)

% cell reduction: R(%)=[(A−B)/A]×100 (Formula 2)

R: cell reduction

A: initial cell count

B: cell counts after a predetermined time

3. Result of Sterilization Test

TABLE 18

Sterility against *E. coli*

| Item | Initial Stage | After 5 min ± 10 sec |
|---|---|---|
| BARODON MINERAL SOLUTION | 7.6 × $10^5$ | <10 (99.9%) |

*( ): cell reduction (%) × 100

Wherein

A: Initial no. of cells

B: No. of cells after a predetermined time.

TABLE 19

Sterility against *S. aureus*

| Item | Initial Stage | After 5 min ± 10 sec |
|---|---|---|
| BARODON MINERAL SOLUTION | 1.3 × 105 | <10 (99.9%) |

TABLE 20

| Sterility against *S. typhimurium* | | |
|---|---|---|
| Item | Initial Stage | After 5 min ± 10 sec |
| BARODON MINERAL SOLUTION | $2.0 \times 10^5$ | <10 (99.9%) |

TABLE 21

| Sterility against *S. aureus* (MRSA) | | |
|---|---|---|
| Item | Initial Stage | After 5 min ± 10 sec |
| BARODON MINERAL SOLUTION | $2.7 \times 10^5$ | <10 (99.9%) |

Example 7

Assay for Efficacy of BARODON-EX (Preparation Example 2)

The functional fermented product BARODON-EX dietary supplement of Preparation Example 2 was added to the Cargill Purina diet manufactured by the Jia Xing plant, China.

Effects of the dietary supplementation of the nonspecific immunostimulant BARODON were examined in hog-raising farms, China, and the results are given in Tables 22 and 23.

TABLE 22

Effect of dietary supplementation of BARODON in Swine-Raising Farm, China Consumer Comment

| Farmer | Location | No. of Mother Pig | BARODON-Supplemented Diet | Competitor's diet | Consumer comment |
|---|---|---|---|---|---|
| Jiang youyi | Huzhou Zhejiang | 120 | 852780B 852880B | Vs. primix | The dietary supplementation of BARODON has prevented piglets from having diarrhea whereas the use of the competitor's diet free of BARODON caused very serious diarrhea in piglets |
| Jiang keman | Zhendahongcecun Shangyu | 100 | 852100B | Vs. primix | As much as 40% of the pigs had diarrhea when they were fed the competitor's diet, but BARODON-supplemented diet reduced the diarrhea rate to 10%. |
| Zhou xingshang | Leyicun Puhu Jiangshan | 40 | 85100B | Vs. competitor's complete | When BARODON-supplemented diet was compared with the control of the competitor's diet free of BARODON, none of the pigs fed with the BARODON-supplemented diet underwent diarrhea whereas 12 pigs of the control group died due to diarrhea. |
| Zhu tuanyuan | dahantancun Shangyu Jiangshan | 40 | 852100B | Vs. competitor's complete | Severe foot-and-mouth disease occurred in competitor's diet-fed pigs, but from the time of the dietary supplementation of BARODON, none had been attacked by the disease. |
| Zhang pengfei | Guzhen Anwei | 80 | 852780B 852880B | — | The steady feeding of BARODON has protected pigs from being attacked by diarrhea or foot-and-mouth disease. |
| Xu fayou | Fenglinmaofucun Jiangshan | 80 | 852100B+ 852288/852488 | | From the time of the dietary supplementation of BARODON, the pigs have not been caught by respiratory diseases, but were so when other diets free of BARODON was fed thereto. |

Contents of Table 22 are rewritten in Table 23, except for farmer names and farm locations.

TABLE 23

Effect of dietary supplementation of BARODON in Swine-Raising Farm, China Consumer Comment

| No. of Mother Pig | BARODON-Supplemented Diet | Competitor's diet | Consumer comment |
|---|---|---|---|
| 120 | 852780B 852880B | Vs. primix | The dietary supplementation of BARODON has prevented piglets from having diarrhea whereas the use of the competitor's diet free of BARODON caused very serious diarrhea in piglets |

TABLE 23-continued

Effect of dietary supplementation of BARODON in Swine-Raising Farm, China
Consumer Comment

| No. of Mother Pig | BARODON-Supplemented Diet | Competitor's diet | Consumer comment |
|---|---|---|---|
| 100 | 852100B | Vs. primix | As much as 40% of the pigs had diarrhea when they were fed the competitor's diet, but BARODON-supplemented diet reduced the diarrhea rate to 10%. |
| 40 | 85100B | Vs. competitor's complete | When BARODON-supplemented diet was compared with the control of the competitor's diet free of BARODON, none of the pigs fed with the BARODON-supplemented diet underwent diarrhea whereas 12 pigs of the control group died due to diarrhea. |
| 40 | 852100B | Vs. competitor's complete | Severe foot-and-mouth disease occurred in competitor's diet-fed pigs, but from the time of the dietary supplementation of BARODON, none had been attacked by the disease. |
| 80 | 852780B<br>852880B | — | The steady feeding of BARODON has protected pigs from<br>being attacked by diarrhea or foot-and-mouth disease. |
| 80 | 852100B+<br>852288/852488 | | From the time of the dietary supplementation of BARODON, the pigs have not been caught by respiratory diseases, but were so when other diets free of BARO-DON<br>was fed thereto. |

1. The farmer of the first farm, which raised a total of 120 mother pigs, said "the dietary supplementation of BARODON has prevented piglets from having diarrhea whereas the use of the competitor's diet free of BARODON caused very serious diarrhea in piglets."

2. The farmer of the second farm, which raised a total of 100 mother pigs, said "as much as 40% of the pigs had diarrhea when they were fed the competitor's diet, but BARODON-supplemented diet reduced the diarrhea rate to 10%."

3. The farmer of the third farm, which raised a total of 40 mother pigs, said "when BARODON-supplemented diet was compared with the control of the competitor's diet free of BARODON, none of the pigs fed with the BARODON-supplemented diet underwent diarrhea whereas 12 pigs of the control group died due to diarrhea."

4. The farmer of the third farm, which raised a total of 40 mother pigs, said "severe foot-and-mouth disease occurred in competitor's diet-fed pigs, but from the time of the dietary supplementation of BARODON, none had been attacked by the disease." (FIG. 39, Table 22).

Figure 39:
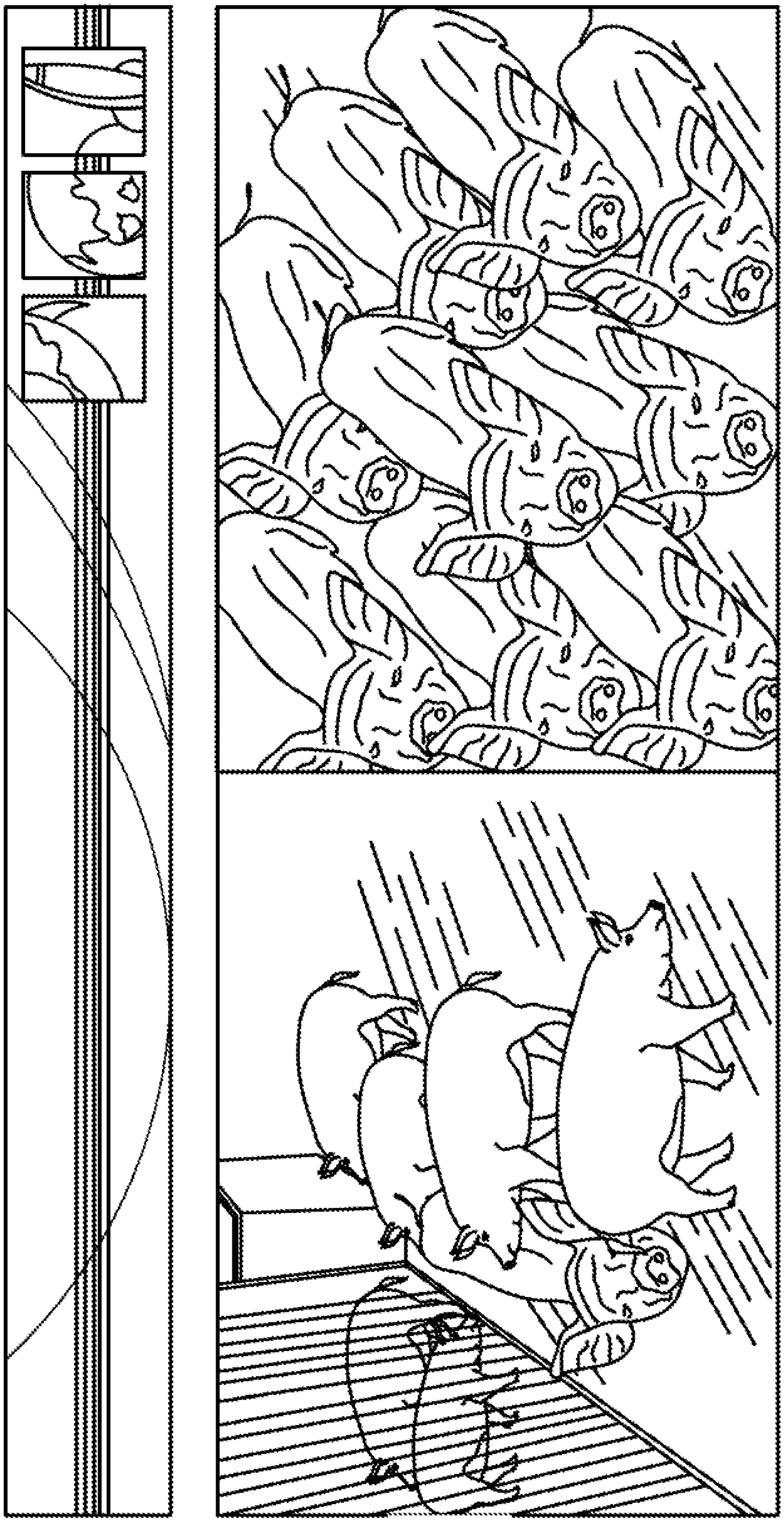
FIG. 39 shows photographs illustrating effects of the dietary supplementation of BARODON in hog-raising farms, China.

As can be seen in FIG. 39, the pig group raised with BARODON-supplemented Purina diet (right panel) seemed to be more vital and healthier than the BARODON-free diet (left panel).

5. The farmer of the fourth farm, which raised a total of 80 mother pigs, said "the steady feeding of BARODON has protected pigs from being attacked by diarrhea or foot-and-mouth disease."

6. The farmer of the fourth farm, which raised a total of 80 mother pigs, said "from the time of the dietary supplementation of BARODON, the pigs have not been caught by respiratory diseases, but were so when other diets free of BARODON was fed thereto."

When a total of 37 piglets were fed BARODON from at the age of 33 weeks to 55 days in a farm located at Jiang Su Province, China, their weight increased from 8.25 kg to 17.55 kg. For this experimental data, the BARODON-supplemented Purina diet was evaluated to help piglets effectively grow (Table 24).

TABLE 24

Effect of Dietary Supplementation of BARODON in Swine-Raising Farm, Jiang Su Province, China (Weight Gain)
Use State of BARODON-supplemented Diet (852100B)

| | Farm' Name | | Tel052786449655 |
|---|---|---|---|
| Swine Species | Wài sān yuến | Order of Delivery | 3 |
| Feeing Type | Free access | Wt. at Birth | 1.92 kg |
| Time to Weaning | 21 days | Wt. at Weaning | 6.06 kg |
| Date of Starting Dietary supplementation | 2012 Mar. 31 | Date of Ending Dietary spplementation | 2012/0819 |
| No. of Pig at Start | 37 | No. of Pig at end | 37 |
| Avg. Wt. at Start | 8.25 kg | Avg. Wt. at end | 17.55 kg |
| Record of diet use | Diet type | Diet Intake (kg) | |
| Diet before delivery | — | — | |
| Diet in weaning stage | 852100B | 440 | |
| Diet in sucking stage | — | — | |
| Diet for growing pig | | | |
| Diet for fattening pig | | | |
| Total amount of diet | | 440 | |
| Amount of diet per head | | 11.89 | |
| Daily weight gain (kg/head) | | 0.28 | |
| Feed conversion ratio | | 1.28 | |
| Farmer's comment | "The Purina diet was very good. It highlypromoted the growth of pigs." | | |

Compared to BARODON-free diets, BARODON-supplemented Purina diets were found to decrease the occurrence of diarrhea by 20.3%, and mortality by 11.42%, increase daily body gain by 0.15 kg, with the reduction of a diet amount per kg of pork by 0.42 kg (Table 25).

TABLE 25

Effect of Dietary Supplementation of BARODON in Swine-Raising Farm, China (Diarrhea, Mortality)

| Item | Competitor's diet | BARODON-Supplemented diet | Difference in effect |
|---|---|---|---|
| No. of Pig at start | 378 | 423 | |
| No. of Pig at end | 325 | 412 | |
| No. of Pig in diarrhea | 115 | 43 | |
| Diarrhea incidence (%) | 30.42 | 10.12 | −20.30 |
| No of dead pig | 53 | 11 | |
| Mortality (%) | 14.02 | 2.60 | −11.42 |
| Wt. per head at start (kg/pig) | 10.14 | 9.72 | |
| Wt. per heat at end (kg/pig) | 16.52 | 17.55 | |
| Wt. gain per head (kg/pig) | 6.38 | 7.83 | |
| Test period (day) | 22 | 18 | |
| Daily Wt. gain (kg/day) | 0.29 | 0.44 | 0.15 |
| Avg. diet intake per head (kg/pig) | 11.30 | 13.86 | |
| Feed conversion rate | 1.77:1 | 1.35:1 | −0.42 |

*This table compares data obtained from farms using BARODON-supplemented diet and not using the diet.

As proven by various long-term experiments, the nonspecific immunostimulant composition of the present invention exhibits excellent defense against the mortality caused by highly pathogenic avian influenza virus (AIV) H5N1, thus improving the survival of animals infected by the AIV H5N1. When used as a supplement of a formulated feed mixture for farmed aquatic organisms (flatfish, shrimp, etc.), the nonspecific immunostimulant composition provides excellent immunostimulation and disease resistance for the farmed aquatic organisms to decrease the mass mortality of aquatic organisms and to increase productivity. Particularly, when raised with a food in mixture with the nonspecific immunostimulant composition, livestock and farmed aquatic organisms are immunologically improved so that they can endure and are protected against epidemic diseases caused by highly pathogenic viruses and bacteria. Further, the nonspecific immunostimulant composition is highly fatal to various bacteria, whether Gram positive or negative, including multiple drug resistant bacteria, such as *S. aureus* (MRSA), *E. coli, S. typhimurium, Streptococcus iniae, Vibrio harveyi*, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A nonspecific immunostimulant composition free of boron, the nonspecific immunostimulant composition comprising, based on 100 parts by weight of potassium carbonate:
- 150 to 300 parts by weight of sodium silicate;
- 2 to 8 parts by weight of sodium thiosulfate; 0.5 to 2 parts by weight of sodium carbonate;
- 0.5 to 2 parts by weight of potassium chloride; 200 to 400 parts by weight of white sugar;
- 300 to 400 parts by weight of water
- 0.1 to 0.3 parts by weight of magnesium sulfate; and
- $1\times10^{-3}$ to $8\times10^{-3}$ parts by weight of silver thiosulfate.

2. A method for preparing a nonspecific immunostimulant composition free of boron, the method comprising:
- mixing in 150 to 300 parts by weight of sodium silicate, 2 to 8 parts by weight of sodium thiosulfate, 0.5 to 2 parts by weight of sodium carbonate, 0.5 to 2 parts by weight of potassium chloride, 300 to 400 parts by weight of water, 0.1 to 0.3 parts by weight of magnesium sulfate, and $1\times10^{-3}$ to $8\times10^{-3}$ parts by weight of silver thiosulfate based on 100 parts by weight of potassium carbonate, while stirring to complete dissolution; and
- dissolving 200 to 400 parts by weight of white sugar in the mixture.

3. A functional fermented product, prepared by fermenting a mixture of 100 parts by weight of the composition of claim 1 and 500 to 2000 parts by weight of feed and drying the fermented mixture into a powder.

* * * * *